(12) United States Patent
Yu et al.

(10) Patent No.: US 11,643,456 B2
(45) Date of Patent: May 9, 2023

(54) HUMAN ANTIBODIES, PHARMACEUTICAL COMPOSITIONS AND METHODS

(71) Applicant: OBI PHARMA, INC., Taipei (TW)

(72) Inventors: Cheng-Der Tony Yu, San Diego, CA (US); Woan Eng Chan, Taipei (TW); Shu-Yu Lee, Taipei (TW); Jiann-Shiun Lai, Taipei (TW); I-Ju Chen, Taipei (TW)

(73) Assignee: OBI PHARMA, INC., Taipei (TW)

( * ) Notice: Subject to any disclaimer, the term of this patent is extended or adjusted under 35 U.S.C. 154(b) by 351 days.

(21) Appl. No.: 16/321,417

(22) PCT Filed: Jul. 31, 2017

(86) PCT No.: PCT/US2017/044713
§ 371 (c)(1),
(2) Date: Jan. 28, 2019

(87) PCT Pub. No.: WO2018/023121
PCT Pub. Date: Feb. 1, 2018

(65) Prior Publication Data
US 2021/0284719 A1  Sep. 16, 2021

Related U.S. Application Data

(60) Provisional application No. 62/368,407, filed on Jul. 29, 2016.

(51) Int. Cl.
| | | |
|---|---|---|
| C07K 16/18 | (2006.01) | |
| A61K 47/68 | (2017.01) | |
| A61K 45/06 | (2006.01) | |
| A61K 49/16 | (2006.01) | |
| G01N 33/574 | (2006.01) | |
| C07K 16/44 | (2006.01) | |
| A61K 39/395 | (2006.01) | |

(52) U.S. Cl.
CPC ........ *C07K 16/18* (2013.01); *A61K 39/39583* (2013.01); *A61K 39/39591* (2013.01); *A61K 45/06* (2013.01); *A61K 47/6851* (2017.08); *A61K 49/16* (2013.01); *C07K 16/44* (2013.01); *G01N 33/574* (2013.01); *C07K 2317/21* (2013.01); *C07K 2317/54* (2013.01); *C07K 2317/55* (2013.01); *C07K 2317/565* (2013.01); *C07K 2317/622* (2013.01); *C07K 2317/73* (2013.01); *G01N 2400/02* (2013.01)

(58) Field of Classification Search
CPC .... C07K 16/18; C07K 16/44; C07K 2317/21; C07K 2317/54; C07K 2317/55; C07K 2317/565; C07K 2317/622; C07K 2317/73; A61K 39/39583; A61K 39/39591; A61K 45/06; A61K 47/6851; A61K 49/16; G01N 33/574; G01N 2400/02
See application file for complete search history.

(56) References Cited

U.S. PATENT DOCUMENTS

| | | |
|---|---|---|
| 3,773,919 A | 11/1973 | Boswell et al. |
| 4,203,975 A | 5/1980 | Greven |
| RE30,985 E | 6/1982 | Cartaya |
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |

(Continued)

FOREIGN PATENT DOCUMENTS

| | | |
|---|---|---|
| CN | 1871025 A | 11/2006 |
| CN | 103108654 A | 5/2013 |

(Continued)

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Büll, Christian, et al. "Sialic acid blockade suppresses tumor growth by enhancing T-cell-mediated tumor immunity." Cancer Research 78.13 (2018): 3574-3588.
Chuang, Po-Kai, et al. "Signaling pathway of globo-series glycosphingolipids and β1, 3-galactosyltransferase V (β3GalT5) in breast cancer." Proceedings of the National Academy of Sciences 116.9 (2019): 3518-3523.

(Continued)

*Primary Examiner* — Nelson B Moseley, II
(74) *Attorney, Agent, or Firm* — Prosyla Group PC

(57) ABSTRACT

Pharmaceutical composition comprising antibodies or antigen binding fragments thereof that bind to Globo H, stage-specific embryonic antigen 3 (SSEA-3) and stage-specific embryonic antigen 4 (SSEA-4) are disclosed herein, as well as methods of use thereof. Methods of use include, without limitation, cancer therapies and diagnostics. The antibodies of the disclosure can bind to certain cancer cell surfaces. Exemplary targets of the antibodies disclosed herein can include carcinomas, such as sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

32 Claims, 6 Drawing Sheets
Specification includes a Sequence Listing.

(56) References Cited

U.S. PATENT DOCUMENTS

| | | |
|---|---|---|
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Mather et al. |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |
| 5,580,717 A | 12/1996 | Dower et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,686,416 A | 11/1997 | Kozarich et al. |
| 5,733,743 A | 3/1998 | Johnson et al. |
| 5,804,396 A | 9/1998 | Plowman |
| 5,814,344 A | 9/1998 | Tice et al. |
| 5,821,337 A | 10/1998 | Carter et al. |
| 5,840,523 A | 11/1998 | Simmons et al. |
| 5,869,046 A | 2/1999 | Presta et al. |
| 5,891,996 A | 4/1999 | Mateo de Acosta del Rio et al. |
| 6,004,940 A | 12/1999 | Marasco et al. |
| 6,027,888 A | 2/2000 | Georgiou et al. |
| 6,083,715 A | 7/2000 | Georgiou et al. |
| 6,265,150 B1 | 7/2001 | Terstappen et al. |
| 6,329,173 B1 | 12/2001 | Marasco et al. |
| 6,524,584 B2 | 2/2003 | Kensil |
| 6,544,952 B1 | 4/2003 | Danishefsky et al. |
| 6,703,019 B1 | 3/2004 | Malfroy-Camine |
| 7,595,292 B2 | 9/2009 | Brocchini et al. |
| 8,268,969 B2 | 9/2012 | Wong et al. |
| 9,850,473 B2 | 12/2017 | Wang |
| 10,815,307 B2 | 10/2020 | Yu et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0129186 A1 | 7/2003 | Beliveau et al. |
| 2003/0153492 A1 | 8/2003 | Danishefsky et al. |
| 2003/0162695 A1 | 8/2003 | Schatzberg et al. |
| 2004/0018194 A1 | 1/2004 | Francisco et al. |
| 2004/0131692 A1 | 7/2004 | Kreuter et al. |
| 2004/0204354 A1 | 10/2004 | Nelson et al. |
| 2004/0208884 A1 | 10/2004 | Danishefsky et al. |
| 2004/0229310 A1 | 11/2004 | Simmons |
| 2004/0247608 A1 | 12/2004 | Krantz et al. |
| 2005/0048572 A1 | 3/2005 | Reilly et al. |
| 2005/0089473 A1 | 4/2005 | Black et al. |
| 2005/0124533 A1 | 6/2005 | Schatzberg et al. |
| 2006/0035267 A1 | 2/2006 | Livingston et al. |
| 2007/0059769 A1 | 3/2007 | Blixt et al. |
| 2009/0317411 A1 | 12/2009 | Wong et al. |
| 2010/0136042 A1* | 6/2010 | Wong ............ A61K 39/001173 424/193.1 |
| 2010/0166790 A1 | 7/2010 | Agadjanyan et al. |
| 2010/0286035 A1 | 11/2010 | Ohtaki et al. |
| 2011/0117009 A1 | 5/2011 | Kratz et al. |
| 2012/0237532 A1 | 9/2012 | Olbrich et al. |
| 2012/0294859 A1 | 11/2012 | Goletz et al. |
| 2012/0321583 A1 | 12/2012 | Yurkovetskiy et al. |
| 2012/0328646 A1 | 12/2012 | Wong et al. |
| 2013/0095173 A1 | 4/2013 | Danishefsky et al. |
| 2013/0232589 A1 | 9/2013 | Papkoff et al. |
| 2014/0363455 A1 | 12/2014 | Stull et al. |
| 2015/0030669 A1 | 1/2015 | Platscher et al. |
| 2015/0087814 A1 | 3/2015 | Wang et al. |
| 2015/0297696 A1 | 10/2015 | Yu et al. |
| 2015/0316556 A1 | 11/2015 | Hardt et al. |
| 2015/0344551 A1 | 12/2015 | Wong et al. |
| 2016/0051672 A1 | 2/2016 | Stewart et al. |
| 2016/0074522 A1 | 3/2016 | Okuda et al. |
| 2016/0102151 A1 | 4/2016 | Wong et al. |
| 2016/0339089 A1 | 11/2016 | Yu et al. |
| 2017/0067885 A1 | 3/2017 | Yu et al. |
| 2017/0101462 A1 | 4/2017 | Yu et al. |
| 2017/0283488 A1 | 10/2017 | Yu et al. |
| 2017/0283489 A1 | 10/2017 | Bosio et al. |
| 2017/0304419 A1 | 10/2017 | Yu et al. |
| 2017/0335281 A1 | 11/2017 | Loew et al. |
| 2018/0028629 A1 | 2/2018 | Yu et al. |
| 2018/0193481 A1 | 7/2018 | Chang et al. |
| 2018/0208915 A1 | 7/2018 | Kawaguchi et al. |
| 2018/0291109 A1 | 10/2018 | Lin et al. |
| 2018/0339061 A1 | 11/2018 | Yu et al. |

FOREIGN PATENT DOCUMENTS

| | | |
|---|---|---|
| EP | 0404097 A2 | 12/1990 |
| EP | 1391213 A1 | 2/2004 |
| EP | 2993182 A1 | 3/2016 |
| JP | 2006-507233 A | 3/2006 |
| JP | 2011524375 A | 9/2011 |
| JP | 2011524417 A | 9/2011 |
| JP | 2016500256 A | 1/2016 |
| KR | 10-2012-0014238 A | 2/2012 |
| WO | WO 87/00195 A1 | 1/1987 |
| WO | WO 90/03184 A1 | 4/1990 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/09690 A2 | 6/1992 |
| WO | WO 93/01161 A1 | 1/1993 |
| WO | WO 93/06213 A1 | 4/1993 |
| WO | WO 93/007861 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 94/011026 A2 | 5/1994 |
| WO | WO 95/011010 A1 | 4/1995 |
| WO | WO 96/07754 A1 | 3/1996 |
| WO | WO 96/11711 A1 | 4/1996 |
| WO | WO 96/30347 A1 | 10/1996 |
| WO | WO 96/33735 A1 | 10/1996 |
| WO | WO 96/33978 A1 | 10/1996 |
| WO | WO 96/33980 A1 | 10/1996 |
| WO | WO 96/34096 A1 | 10/1996 |
| WO | WO 96/40210 A1 | 12/1996 |
| WO | WO 97/38983 A1 | 10/1997 |
| WO | WO 98/24893 A2 | 6/1998 |
| WO | WO 98/36772 A1 | 8/1998 |
| WO | WO 98/43960 A1 | 10/1998 |
| WO | WO 99/06378 A1 | 2/1999 |
| WO | WO 99/06396 A1 | 2/1999 |
| WO | WO 99/09016 A1 | 2/1999 |
| WO | WO 99/042130 A1 | 8/1999 |
| WO | WO 2000/41720 A1 | 7/2000 |
| WO | WO 2000/48630 A1 | 8/2000 |
| WO | WO-2000/49412 A1 | 8/2000 |
| WO | WO 2003/015796 A1 | 2/2003 |
| WO | WO 2003/043583 A2 | 5/2003 |
| WO | WO 2003/077945 A1 | 9/2003 |
| WO | WO 2004/011476 A1 | 2/2004 |
| WO | WO 2004/032828 A2 | 4/2004 |
| WO | WO 2005/007197 A2 | 1/2005 |
| WO | WO 2006/105152 A2 | 10/2006 |
| WO | WO 2006/134423 A2 | 12/2006 |
| WO | WO 2007/026190 A2 | 3/2007 |
| WO | 2007047764 A2 | 4/2007 |

(56) References Cited

FOREIGN PATENT DOCUMENTS

| | | |
|---|---|---|
| WO | WO 2007/044515 A1 | 4/2007 |
| WO | WO 2009/035494 A2 | 3/2009 |
| WO | WO 2009/126737 A2 | 10/2009 |
| WO | 2010005735 A3 | 3/2010 |
| WO | WO-2011/156774 A2 | 12/2011 |
| WO | WO 2014/107652 A2 | 7/2014 |
| WO | WO 2014/178195 A1 | 11/2014 |
| WO | WO 2015/143123 A2 | 9/2015 |
| WO | WO 2015/157629 A2 | 10/2015 |
| WO | WO 2015/159118 A2 | 10/2015 |
| WO | 2015157629 A3 | 12/2015 |
| WO | WO 2016/026742 A1 | 2/2016 |
| WO | WO 2016/044326 A1 | 3/2016 |
| WO | 2016118961 A1 | 7/2016 |
| WO | WO 2016/118961 A1 | 7/2016 |
| WO | WO 2016/123593 A1 | 8/2016 |
| WO | 2017004150 A1 | 1/2017 |
| WO | WO 2017/041027 A1 | 3/2017 |
| WO | 2017062792 A1 | 4/2017 |
| WO | WO 2017/062792 A1 | 4/2017 |
| WO | 2016044326 A9 | 5/2017 |
| WO | 2017185089 A2 | 10/2017 |
| WO | WO 2017/172990 A1 | 10/2017 |
| WO | WO 2018/002640 A2 | 1/2018 |
| WO | 2018022933 A1 | 2/2018 |
| WO | WO 2018/022933 A1 | 2/2018 |
| WO | WO 2018/023121 A1 | 2/2018 |
| WO | WO 2018/094414 A1 | 5/2018 |

OTHER PUBLICATIONS

International Search Report/Written Opinion dated Oct. 18, 2019 in counterpart application PCT/US2019/035168, 13 pages.
International Search Report dated Dec. 3, 2019 in counterpart application PCT/US2019/039414, 5 pages.
Ragupathi, Govindaswami, et al. "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm." Glycoconjugate Journal 15.3 (1998): 217-221.
Final Office Action issued in U.S. Appl. No. 16/454,750 dated May 27, 2021.
Substantive Examination Report, Office Paper No. 7, issued in Philippines Application No. 1-2017-500478 dated Oct. 21, 2020.
Substantive Examination Report, Office Paper No. 9, issued in Philippines Application No. 1-2017-500478 dated Jun. 10, 2021.
Abrahmsén et al, "Analysis of signals for secretion in the staphylococcal protein A gene," EMBO J., Dec. 30, 1985, 4(13B):3901-3906.
Allen, P. Z. et al., Immunochemical Studies on a Sophorosyl-Azoprotein Conjugate, Biochemistry, 1967, 6(10), 3029-3036.
Arié et al., "Chaperone function of FkpA, a heat shock prolyl isomerase, in the periplasm of *Escherichia coli*," Mol. Microbiol., Jan. 2001, 39(1):199-210.
Arigi, Emma, et al. "Design of a covalently bonded glycosphingolipid microarray." Glycoconjugate Journal 29.1 (2012): 1-12.
Avery, Oswald et al., Chemo-Immunological Studies on Conjugated Carbohydrate-Proteins, J. Exp. Med., 1929, 50, 533-550.
Bachmann, Cellular and Molecular Biology, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.
Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.
Barbas, C.F. et al., "Semisynthetic combinatorial antibody libraries: a chemical solution to the diversity problem" Proc. Natl. Acad. Sci. USA, May 15, 1992, 89(10): 4457-4461.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Berenbaum, M. C., What is Synergy?, Pharmacol. Rev. 41(2) :93-141, 1989.
Bergman, Jan, and Lennart Venemalm. "Efficient synthesis of 2-chloro-, 2-bromo-, and 2-iodoindole." The Journal of Organic Chemistry 57.8 (1992): 2495-2497.
Bertozzi, CR et al., Glycans in Cancer and Inflammation—Potential for Therapeutics and Diagnostics, Nat Rev Drug Discovery, 2005, 4, 477-488.
Bhaskar, Vinay, et al. "E-selectin up-regulation allows for targeted drug delivery in prostate cancer." Cancer Research 63.19 (2003): 6387-6394.
Bird, R.E., et al., "Single-chain antigen-binding proteins" Science Oct. 21, 1988; 242(4877):423-426.
Bliss, C.I., The Calculation of Microbial Assays, Bacterial. Rev. 20:243-258, 1956.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Borisy, Alexis et al., Systematic Discovery of Multicomponent Therapeutics, Proc. Natl. Acad. Sci. 100(13):7977-7982, 2003.
Bosse, Folkert et al., Linear Synthesis of the Tumor-Associated Carbohydrate Antigens Globo-H, SSEA-3, and Gb3, J Org Chem. 67(19):6659-70, 2002.
Bothmann et al., "The periplasmic *Escherichia coli* peptidylprolyl cis,trans-isomerase FkpA. I. Increased functional expression of antibody fragments with and without cis-prolines," J. Biol. Chem., Jun. 2, 2000, 275(22):17100-17105.
Bowie, Ju et al., Deciphering the Message in Protein Sequences: Tolerance to Amino Acid Substitutions, Science, 247: 1306-1310 (1990).
Bremer, E. G., et al. "Characterization of a glycosphingolipid antigen defined by the monoclonal antibody MBr1 expressed in normal and neoplastic epithelial cells of human mammary gland." Journal of Biological Chemistry 259.23 (1984): 14773-14777.
Brennan et al., "Preparation of bispecific antibodies by chemical recombination of monoclonal immunoglobulin G1 fragments," Science, Jul. 5, 1985, 229(4708):81-83.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," Year in Immunol., 1993, 7:33-40.
Carter et al., "High level *Escherichia coli* expression and production of a bivalent humanized antibody fragment," Nature Biotechnology, Feb. 1992, 10(2):163-167.
Carter et al., "Humanization of an anti-p185HER2 antibody for human cancer therapy," Proc. Natl. Acad. Sci. U.S.A., May 15, 1992, 89(10):4285-4289.
Casset, Florence, et al. "A peptide mimetic of an anti-CD4 monoclonal antibody by rational design." Biochemical and Biophysical Research Communications 307.1 (2003): 198-205.
Chang et al., "Potent immune-modulating and anticancer effects of NKT cell stimulatory glycolipids," Proc. Natl. Acad. Sci. USA, Jun. 19, 2007, 104(25):10299-10304.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.

(56) References Cited

OTHER PUBLICATIONS

Chen et al., "Chaperone activity of DsbC," J. Bio. Chem., July 9. 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.
Cheung, Sarah et al., Stage-Specific Embryonic Antigen-3 (SSEA-3) and β3GalT5 are cancer specific and Significant Markers for Breast Cancer Stem Cells, PNAS, Jan. 26, 2016, vol. 113, No. 4, pp. 960-965.
Chothia et al., "Canonical structures for the hypervariable regions of immunoglobulins," J. Mol. Biol., Aug. 20, 1987, 196(4):901-917.
Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.
Chou, T. C. and Talalay, P., Quantitative Analysis of Dose-Effect Relationships: The Combined Effects of Multiple Drugs or Enzyme Inhibitors. Adv. Enzyme Regul. 22:27-55, 1984.
Clackson et al., "Making antibody fragments using phage display libraries," Nature, Aug. 15, 1991, 352(6336):624-628.
ClinicalTrials.gov [Internet]. Bethesda (MD): National Library of Medicine (US). Jan. 24, 2012—Trial of Active Imunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.
Clynes, Raphael, et al. "Fc receptors are required in passive and active immunity to melanoma." Proceedings of the National Academy of Sciences 95.2 (1998): 652-656.
Colman, P.M., "Effects of amino acid sequence changes on antibody-antigen interactions," Research in Immunology 145:33-36, 1994.
Cunningham et al., "High-resolution epitope mapping of hGH-receptor interactions by alanine-scanning mutagenesis," Science, Jun. 2, 1989, 244(4908):1081-1085.
Cuzick, J., et al. "Overview of the main outcomes in breast-cancer prevention trials." The Lancet 361.9354 (2003): 296-300.
Danishefsky, Samuel J., et al. "Development of Globo-H cancer vaccine." Accounts of Chemical Research 48.3 (2015): 643-652.
De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Doronina, Svetlana O., et al. "Development of potent monoclonal antibody auristatin conjugates for cancer therapy." Nature Biotechnology 21.7 (2003): 778-784.
Eller, Chelcie et al., Human Cancer Antigen Globo H Is a Cell-Surface Ligand for Human Ribonuclease 1, ACS Central Science. vol. 1, p. 181-90, Jul. 13, 2015.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Evans, T. R. J., and S. B. Kaye. "Vaccine therapy for cancer—fact or fiction?" Q J Med 92.6 (1999): 299-307.
Extended European Search Report, Application No. 15842660.1, dated Mar. 12, 2018, 9 pages.
Extended European Search Report from corresponding European App. No. 16843131.0, dated Feb. 14, 2019, 13 Pages.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.

Feng, Li. "Probing lipid-protein interactions using lipid microarrays." Prostaglandins & other lipid mediators 77.1-4 (2005): 158-167.
Fielder, R. J. et al., An Immunogenic Polysaccharide-Protein Conjugate, J. Immunol., 1970, 105(1), 265-267.
Fishwild et al., "High-avidity human IgGk monoclonal antibodies from a novel strain of minilocus transgenic mice," Nature Biotechnol., Jul. 1996, 14(7):845-851.
Fitzgerald, Jonathan et al., Systems Biology and Combination Therapy in the Quest for Clinical Efficacy, Nature Chem. Biol. 2(9):458-466, 2006.
Francisco, Joseph A., et al. "cAC10-vcMMAE, an anti-CD30—monomethyl auristatin E conjugate with potent and selective antitumor activity." Blood 102.4 (2003): 1458-1465.
Galfrè et al., "Preparation of monoclonal antibodies: strategies and procedures," Methods Enzymol., 1981, 73(Pt B):3-46.
Gazzano-Santoro, Hélène, et al. "A non-radioactive complement-dependent cytotoxicity assay for anti-CD20 monoclonal antibody." Journal of Immunological Methods 202.2 (1997): 163-171.
Gijsen, H.J. et al., Recent Advances in the Chemoenzymatic Synthesis of Carbohydrates and Carbohydrate Mimetics, Chem. Rev., 96, 443-473, 1996.
Gilewski, Teresa et al., Immunization of Metastatic Breast Cancer Patients with a Fully Synthetic Globo H Conjugate: A Phase I Trial, Proc Natl Acad Sci USA 98:3270-3275, 2001.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice 2nd ed., Chapter 3: Production of Monoclonal Antibodies, 1986, pp. 59-103, Academic Press, London.
Goebel, Walther et al., Chemo-immunological Studies on Conjugated Carbohydrate-Proteins, J. Exp. Med., 1929, 50, 521-531.
Gonnet, GH et al., Exhaustive Matching of the Entire Protein Sequence Database, Science 256: 1443-1445 (1992).
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Grant, Oliver C., et al. "Presentation, presentation, presentation! Molecular-level insight into linker effects on glycan array screening data." Glycobiology 24.1 (2014): 17-25.
Greco, William et al., The Search for Synergy: A Critical Review From a Response Surface Perspective, Pharmacol. Rev. 47(2) :331-385, 1995.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in Escherichia coli," J. Immunol., Jun. 1, 1994, 152(11):5368-5374.
Guss et al., "Structure of the IgG-binding regions of streptococcal protein G," EMBO J., Jul. 1986, 5(7):1567-1575.
Hakomori et al., "Glycosphingolipid antigens and cancer therapy," Chem. & Biol., Feb. 1997, 4(2):97-104.
Hakomori, Sen-Itiroh, Tumor-associated carbohydrate antigens defining tumor malignancy: Basis for development of and-cancer vaccines, 2001, Advances in Experimental Medicine and Biology. 491 :369-402.
Ham, Richard et al., Media and Growth Requirements, Meth. Enz 58, 44-93 (1979).
Hammerling et al., "Production of antibody-producing hybridomas in the rodent systems." in: Monoclonal Antibodies and T-Cell Hybridomas, 563-587, 1981, Elsevier North-Holland.
Hara et al., "Overproduction of penicillin-binding protein 7 suppresses thermosensitive growth defect at low osmolarity due to an spr mutation of Escherichia coli," Microbial Drug Resistance, Spring 1996, 2(1):63-72.
Harris, "Production of humanized monoclonal antibodies for in vivo imaging and therapy," Biochem. Soc. Transactions, Nov. 1995, 23(4):1035-1038.

(56) References Cited

OTHER PUBLICATIONS

Harris, J. Robin, et al. "Keyhole limpet hemocyanin (KLH), II: Characteristic reassociation properties of purified KLH1 and KLH2." Micron 28.1 (1997): 43-56.
Harris, J. R., and J. Mark 1. "Keyhole limpet hemocyanin (KLH): a biomedical review." Micron 30.6 (1999): 597-623.
Hawkins et al., "Selection of phage antibodies by binding affinity. Mimicking affinity maturation," J. Mol. Biol., 1992, 226(3):889-896.
Heffernan, Michael J., et al. "In vivo efficacy of a chitosan/IL-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hirano, Fumiya, et al. "Blockade of B7-H1 and PD-1 by monoclonal antibodies potentiates cancer therapeutic immunity." Cancer Research 65.3 (2005): 1089-1096.
Hogrefe, H.H. et al., "A bacteriophage lambda vector for the cloning and expression of immunoglobulin Fab fragments on the surface of filamentous phage" Gene, 1993, 128(1): 119-126.
Holliger et al., "'Diabodies': small bivalent and bispecific antibody fragments," Proc. Natl. Acad. Sci. U.S.A., Jul. 15, 1993, 90(14):6444-6448.
Holm, Patrik, Rozbeh Jafari, and Birgitta E. Sundström. "Functional mapping and single chain construction of the anti-cytokeratin 8 monoclonal antibody TS1." Molecular Immunology 44.6 (2007): 1075-1084.
Hoogenboom et al., "By-passing immunisation: Human antibodies from synthetic repertoires of germline VH gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Huang, Cheng-Yuan et al., Carbohydrate Microarray for Profiling the Antibodies Interacting with Globo H Tumor Antigen, Proc Natl Acad Sci, 103:15-20, 2006.
Huang, Yen-Lin, and Chung-Yi Wu. "Carbohydrate-based vaccines: challenges and opportunities." Expert Review of Vaccines 9.11 (2010): 1257-1274.
Huang, Yen-Lin, et al. "Carbohydrate-based vaccines with a glycolipid adjuvant for breast cancer." Proceedings of the National Academy of Sciences 110.7 (2013): 2517-2522.
Hurle et al., "Protein engineering techniques for antibody humanization," Curr. Opin. Biotechnol., Aug. 1994, 5(4):428-433.
Huston, James et al., "Protein Engineering of Antibody Binding Sites: Recovery of Specific Activity in an Anti-Digoxin Single-Chain Fv Analogue Produced in *Escherichia coli*" Proc. Natl. Acad. Sci. USA, 1988, 85:5879-5883.
International Search Report dated Jan. 8, 2016 in counterpart application PCT/IB2014/002744, 3 pages.
International Search Report and Written Opinion of the International Searching Authority, from corresponding International Patent Application No. PCT/US2015/050270, dated Dec. 15, 2015, 14 Pages.
International Search Report and Written Opinion of the International Searching Authority, from corresponding International Patent Application No. PCT/US16/50252, dated Nov. 17, 2016, 12 Pages.
International Search Report and Written Opinion dated Jul. 7, 2017, from corresponding International Patent Application No. PCT/US2017/024853, by Yu, Cheng-Der Tony et al., "Antibodies, Pharmaceutical Compositions and Methods", filed Mar. 29, 2017, 21 pages.
International Search Report/Written Opinion dated Oct. 31, 2017 in counterpart PCT Application No. PCT/US2017/044244, 13 pages.
International Search Report dated Nov. 28, 2017 in counterpart application PCT/US2017/044713, 6 pages.
International Search Report/Written Opinion dated Mar. 12, 2018 in counterpart PCT Application No. PCT/US17/062886, 22 pages.
Jackson et al., "In vitro antibody maturation: Improvement of a high affinity, neutralizing antibody against IL-1β," J. Immunol., Apr. 1, 1995, 154(7):3310-3319.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Jeon, Insik et al., A Practical Total Synthesis of Globo-H for Use in Anticancer Vaccines, J. Org. Chem., 2009, 74(21), pp. 8452-8455.
Jones et al., "Rapid PCR-cloning of full-length mouse immunoglobulin variable regions," Nature Biotechnol., Jan. 1991, 9(1):88-89.
Jones et al., "Replacing the complementarity-determining regions in a human antibody with those from a mouse," Nature, May 29-Jun. 4, 1986, 321(6069):522-525.
Jones, "Analysis of polypeptides and proteins," Adv. Drug Delivery Rev., Jan.-Apr. 1993, 10(1):29-90.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kannagi, Reiji, et al. "Stage-specific embryonic antigens (SSEA-3 and -4) are epitopes of a unique globo-series ganglioside isolated from human teratocarcinoma cells." EMBO Journal 2.12 (1983): 2355-2361.
Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.
Klussman, Kerry, et al. "Secondary mAh-vcMMAE conjugates are highly sensitive reporters of antibody internalization via the lysosome pathway." Bioconjugate chemistry 15.4 (2004): 765-773.
Koeller, Kathryn et al., Enzymes for Chemical Synthesis, Nature, 409, 232-240, 2001.
Köhler et al., "Continuous cultures of fused cells secreting antibody of predefined specificity," Nature, Aug. 7, 1975, 256(5517):495-497.
Komenaka, Ian, Heidi Hoerig, and Howard L. Kaufman. "Immunotherapy for melanoma." Clinics in Dermatology 22.3 (2004): 251-265.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Kontermann, "Intrabodies as therapeutic agents," Methods, Oct. 2004, 34(2):163-170.
Kostelny et al., "Formation of a bispecific antibody by the use of leucine zippers," J. Immunol., Mar. 1, 1992, 148(5):1547-1553.
Kozbor, "A human hybrid myeloma for production of human monoclonal antibodies," J. Immunol., Dec. 1984, 133(6):3001-3005.
Krainer, Florian et al., An Updated View on Horseradish Peroxidases: Recombinant Production and Biotechnological Applications, Applied Microbiology and Biotechnology, vol. 99, p. 1611-1625, Jan. 11, 2015.
Kufer, Peter, et al. "A revival of bispecific antibodies." Trends in biotechnology 22.5 (2004): 238-244.
Lee et al., "Bivalent antibody phage display mimics natural immunoglobulin," J. Immunol. Methods, Jan. 2004, 284(1-2):119-132.

(56) References Cited

OTHER PUBLICATIONS

Lee et al., "High-affinity human antibodies from phage-displayed synthetic Fab libraries with a single framework scaffold," J. Mol. Biol., Jul. 23, 2004, 340(5):1073- 1093.
Lee et al. "Immunogenicity study of Globo H analogues with modification at the reducing or nonreducing end of the tumor antigen" Journal of the American Chemical Society, (2014) 136(48), 16844-16853.
Lehninger, Biochemistry: The Molecular Basis of Cell Structure and Function, 2nd ed., 1975, pp. 73-75, Worth Publishers, New York.
Leung et al., "A method for random mutagenesis of a defined DNA segment using a modified polymerase chain reaction," Technique—A Journal of Methods in Cell and Molecular Biology, Aug. 1989, 1(1):11-15.
Liang, Pi-Hui, et al. "Quantitative Microarray Analysis of Intact Glycolipid-CD1d Interaction and Correlation with Cell-Based Cytokine Production." Journal of the American Chemical Society 130.37 (2008): 12348-12354.
Lindmark et al., "Binding of immunoglobulins to protein A and immunoglobulin levels in mammalian sera," J. Immunol. Meth., Aug. 12, 1983, 62(1):1-13.
Liu et al., "Eradication of large colon tumor xenografts by targeted delivery of maytansinoids," Proc. Natl., Acad. Sci. U.S.A., Aug. 6, 1996, 93(16):8618-8623.
Liu, Gui, et al. "QS-21 structure/function studies: effect of acylation on adjuvant activity." Vaccine 20.21-22 (2002): 2808-2815.
Livingston, Philip, "Augmenting the immunogenicity of carbohydrate tunor antigens" Seminars in Cancer Biology, Cancer Biol, 6(6):357-366, 1995.
Lloyd, Kenneth, "Tumor Antigens Known to be Immunogenic in Man" in Specific Immunotherapy of Cancer with Vaccines, 1993, 690, 50-58.
Lode et al., "Targeted therapy with a novel enediyene antibiotic calicheamicin θI1 effectively suppresses growth and dissemination of liver metastases in a syngeneic model of murine neuroblastoma," Cancer Res., Jul. 15, 1998, 58(14):2925-2928.
Lonberg et al., "Antigen-specific human antibodies from mice comprising four distinct genetic modifications," Nature, Apr. 28, 1994, 368(6474):856-859.
Lonberg et al., "Human antibodies from transgenic mice," Int. Rev. Immunol., 1995, 13(1):65-93.
Lou, et al., Stage-specific embryonic antigent-4 as a potential therapeutic target in glioblastoma multiforms and other cancers. Proc Natl Acad Sci USA 2014, 111(7):2482-7.
Lucas, A.H. et al., Carbohydrate Moieties as Vaccine Candidates: Meeting Summary, Vaccine, vol. 28(4), Jan. 2010, pp. 1121-1131.
Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.
Mandler et al., "Modifications in synthesis strategy improve the yield and efficacy of geldanamycin-herceptin immunoconjugates," Bioconjugate Chem., Jul.-Aug. 2002, 13(4):786-791.
Mandler et al., "Synthesis and evaluation of antiproliferative activity of a geldanamycin-Herceptin™ immunoconjugate," Bioorganic & Med. Chem. Letters, May 15, 2000, 10(10):1025-1028.
Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999): 6953-6958.
Mao, Weiguang, et al. "EphB2 as a therapeutic antibody drug target for the treatment of colorectal cancer." Cancer Research 64.3 (2004): 781-788.
Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.
Marasco, "Intrabodies: turning the humoral immune system outside in for intracellular immunization," Gene Therapy, Jan. 1997, 4(1):11-15.
Marks et al., "By-passing immunization. Human antibodies from V-gene libraries displayed on phage," J. Mol. Biol., Dec. 5, 1991, 222(3):581-597.
Marks et al., "By-passing immunization: Building high affinity human antibodies by chain shuffling," Nature Biotechnology, Jul. 1992, 10(7):779-783.
Martineau, R.S. et al., Immunochemical Studies on a Panosyl-Azoprotein conjugate, Immunochemistry, vol. 8, 705-718, 1971.
Mather et al., "Culture of testicular cells in hormone-supplemented serum-free medium," Annals N.Y. Acad. Sci., 1982, 383:44-68.
Mather, "Establishment and characterization of two distinct mouse testicular epithelial cell lines," Biol. Reprod., Aug. 1980, 23(1):243-252.
Matsuda, F. et al., "Structure and physical map of 64 variable segments in the 3' 0.8-megabase region of the human immunoglobulin heavy-chain locus." Nature Genet., 1993, 3: 88-94.
McCafferty et al., "Phage antibodies: Filamentous phage displaying antibody variable domains," Nature, Dec. 6, 1990, 348:552-554.
Menard S et al., Generation of Monoclonal Antibodies Reacting with Normal and Cancer Cells of Human Breast, Cancer Res 43: 1295-1300, 1983.
Miller, Kathy, et al. "Design, construction, and in vitro analyses of multivalent antibodies." The Journal of Immunology 170.9 (2003): 4854-4861.
Milstein, C & Cuello, AC, Hybrid Hydridomas and their use in immunohistochemistry, Nature 305, 537-540, Oct. 1993.
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.
Morrison et al., "Chimeric human antibody molecules: mouse antigen-binding domains with human constant region domains," Proc. Natl. Acad. Sci. U.S.A., Nov. 1984, 81(21):6851-6855.
Morrison, "Immunology. Success in specification," Nature, Apr. 28, 1994, 368(6474):812-813.
Munson et al., "Ligand: a versatile computerized approach for characterization of ligand-binding systems," Anal. Biochem., Sep. 1, 1980, 107(1):220-239.
Neuberger et al., "Recombinant antibodies possessing novel effector functions," Nature, Dec. 13-19, 1984, 312(5995):604-608.
Neuberger, "Generating high-avidity human Mabs in mice," Nature Biotechnol., Jul. 1996, 14(7):826.
Nicolaou, K.C. et al., "Calicheamicin θI1: A rationally designed molecule with extremely potent and selective DNA cleaving properties and apoptosis inducing activity." Angew. Chem. Intl. Ed. Engl., Feb. 1, 1994, 33(2):183-186.
Niculescu-Duvaz et al., "Antibody-directed enzyme prodrug therapy (Adept): A review," Adv. Drg. Del. Rev., Jul. 7, 1997, 26(2-3):151-172.
Nikula, Kristen et al., Animal Models of Chronic Bronchitis and Their Relevance to Studies of Particle-Induced Disease, Inhal. Toxicol. 4(12): 123-153, 2000.
Office Action issued in corresponding Taiwan patent application No. 103131876, dated Dec. 26, 2016, 7 pages.
Orlandi et al., "Cloning immunoglobulin variable domains for expression by the polymerase chain reaction," Proc. Natl. Acad. Sci. U.S.A., May 1989, 86(10):3833-3837.
Ørum et al., "Efficient method for constructing comprehensive murine Fab antibody libraries displayed on phage." Nucleic Acids Res., Sep. 25, 1993, 21(19):4491-4498.
Oxenius, Annette, et al. "CpG-containing oligonucleotides are efficient adjuvants for induction of protective antiviral immune responses with T-cell peptide vaccines." Journal of Virology 73.5 (1999): 4120-4126.
Papanastassiou et al., "The potential for efficacy of the modified (ICP 34.5−) herpes simplex virus HSV1716 following intratumoural injection into human malignant glioma: a proof of principle study," Gene Therapy, Mar. 2002, 9(6):398-406.

(56) References Cited

OTHER PUBLICATIONS

Paul, William E. "Structure and Function of Immunoglobulins, Fundamental Immunology." Chapter 9 (1993), 3rd Edition: 292-295.
Pearson, William, Using the FASTA Program to Search Protein and DNA Sequence Databases, Methods Mol. Biol. 243:307-331, 1994.
Pegram, Mark et al., Inhibitory Effects of Combinations of HER-2/neu Antibody and Chemotherapeutic Agents Used for Treatment of Human Breast Cancers, Oncogene 18:2241-2251, 1999.
Pegram, Mark et al., Rational Combinations of Trastuzumab With Chemotherapeutic Drugs Used in the Treatment of Breast Cancer, J. of the Nat. Cancer Inst. 96(10):739-749, 2004.
Plückthun, "Mono- and bivalent antibody fragments produced in *Escherichia coli*: Engineering, folding and antigen binding," Immunol. Rev., Dec. 1992, 130:151-188.
Plückthun, Handbook of Experimental Pharmacology, vol. 113: The Pharmacology of Monoclonal Antibodies, Chapter 11: Antibodies from *Escherichia coli*, Rosenberg et al., eds., 1994, pp. 269-315, Springer-Verlag, Berlin.
Presta et al., "Humanization of an antibody directed against IgE," J. Immunol., Sep. 1, 1993, 151(5):2623-2632.
Presta et al., "Humanization of an anti-vascular endothelial growth factor monoclonal antibody for the therapy of solid tumors and other disorders," Cancer Res., Oct. 15, 1997, 57(20):4593-4599.
Presta, Leonard G. "Antibody engineering." Current Opinion in Biotechnology 3.4 (1992): 394-398.
Presta, "Antibody engineering," Curr. Opin. Str. Biol., Aug. 1992, 2(4):593-596.
Proba et al., "Functional antibody single-chain fragments from the cytoplasm of *Escherichia coli*: influence of thioredoxin reductase (TrxB)," Gene, Jul. 4, 1995, 159(2):203-207.
Queen, Cary et al, A Humanized Antibody that Binds to the Interleukin 2 Receptor, Proc Natl Acad Sci., 86: 10029-10033 (1989).
Ragupathi, Govindaswami et al., Immunization of Mice with a Fully Synthetic Globo H Antigen Results in Antibodies against Human Cancer Cells: A Combined Chemical—Immunological Approach to the Fashioning of an Anticancer Vaccine, Angew Chem Int, 36(1-2), 125-128, Feb. 1997.
Ragupathi, Govindaswami, et al. "Constructing an adenocarcinoma vaccine: Immunization of mice with synthetic KH-1 nonasaccharide stimulates anti-KH-1 and anti-Ley antibodies." International Journal of Cancer 99.2 (2002): 207-212.
Ramm et al., "The periplasmic *Escherichia coli* peptidylprolyl cis,trans-isomerase FkpA. II. Isomerase-independent chaperone activity in vitro," J. Biol. Chem., Jun. 2, 2000, 275(22):17106-17113.
Ravetch et al., "Fc receptors," Annu. Rev. Immunol., 1991, 9:457-492.
Reyes et al., "Expression of human β-interferon cDNA under the control of a thymidine kinase promoter from herpes simplex virus," Nature, Jun. 17, 1982, 297(5867):598-601.
Riechmann et al., "Reshaping human antibodies for therapy," Nature, Mar. 24, 1988, 332(6162):323-327.
Rowland et al., "Drug localisation and growth inhibition studies of vindesine-monoclonal anti-CEA conjugates in a human tumour xenograft," Cancer Immunol. Immunother., 1986, 21(3):183-187.
Rüde, Erwin et al., Synthesis of the N-carboxy-α-amino Acid Anhydrides of Several O-acetylated Serine Glycosides, Carbohydr. Research, 1968, 8(2), 219-232.
Rudikoff, Stuart, et al. "Single amino acid substitution altering antigen-binding specificity." Proceedings of the National Academy of Sciences 79.6 (1982): 1979-1983.
Sastry et al., "Cloning of the immunological repertoire in *Escherichia coli* for generation of monoclonal catalytic antibodies: construction of a heavy chain variable region-specific cDNA library," Proc. Natl. Acad. Sci. U.S.A., Aug. 1989, 86(15):5728-5732.
Schier et al., "Identification of functional and structural amino-acid residues by parsimonious mutagenesis," Gene, Mar. 9, 1996, 169(2):147-155.

Schiffman, Mark, and Philip E. Castle. "The promise of global cervical-cancer prevention." New England Journal of Medicine 353.20 (2005): 2101-2104.
Schwarz, Mikael, et al. "A new kind of carbohydrate array, its use for profiling antiglycan antibodies, and the discovery of a novel human cellulose-binding antibody." Glycobiology 13.11 (2003): 749-754.
Search Report issued in corresponding Taiwan patent application No. 103131876, prepared Dec. 20, 2016, 1 page.
Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Sidhu et al., "Phage-displayed antibody libraries of synthetic heavy chain complementarity determining regions," J. Mol. Biol., Apr. 23, 2004, 338(2):299-310.
Siebenlist et al., "*E. coli* RNA polymerase interacts homologously with two different promoters," Cell, Jun. 1980, 20(2):269-281.
Sigma-Aldrich, Product Information for Hemocyanin From Megathura Crenulata, Catalog No. H7017, 1 Page, 2016.
Simmons et al., "Expression of full-length immunoglobulins in *Escherichia coli*: Rapid and efficient production of aglycosylated antibodies," J. Immunol. Methods, May 1, 2002, 263(1-2):133-147.
Sims et al., "A humanized CD18 antibody can block function without cell destruction," J. Immunol., Aug. 15, 1993, 151(4):2296-2308.
Sjölander, A., et al. "ISCOMs: an adjuvant with multiple functions." J. Leukocyte Biol. 64.6 (1998): 713-723.
Skerra, "Bacterial expression of immunoglobulin fragments," Curr. Opinion in Immunol., Apr. 1993, 5(2):256-262.
Slovin, S.F. et al., Carbohydrate Vaccines in Cancer: Immunogenicity of a Fully Synthetic Globo H Hexasaccharide Conjugate in Man, Proc Natl Acad Sci, 96:5710-5715, May 1999.
Sonderstrup, Grete, Development of Humanized Mice as a Model of Inflammatory Arthritis, Springer Sem. Immunopathol. 25: 35-45, 2003.
Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Suresh et al., "Bispecific monoclonal antibodies from hybrid hybridomas," Methods in Enzymology, 1986, 121:210-228.
Syrigos et al., "Antibody directed enzyme prodrug therapy (ADEPT): a review of the experimental and clinical considerations," Anticancer Research, Jan.-Feb. 1999, 19(1A):605-614.
Takeda et al., "Construction of chimaeric processed immunoglobulin genes containing mouse variable and human constant region sequences," Nature, Apr. 4-10, 1985, 314(6010):452-454.
Thorpe, (1985) "Antibody Carriers of Cytotoxic Agents in Cancer Therapy: A Review," in Monoclonal Antibodies '84: Biological and Clinical Applications, A. Pinchera et al. (Ed.s), pp. 475-506.
Tomlinson, I.M. et al., "The repertoire of human germline VH sequences reveals about fifty groups of VH segments with different hypervariable loops" J. Mol. Biol., Oct. 5, 1992, 227(3): 776-798.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Traunecker et al., "Bispecific single chain molecules (Janusins) target cytotoxic lymphocytes on HIV infected cells," EMBO J., Dec. 1991, 10(12):3655-3659.
Tutt et al., "Trispecific F(ab')3 derivatives that use cooperative signaling via the TCR/CD3 complex and CD2 to activate and redirect resting cytotoxic T cells," J. Immunol., Jul. 1, 1991, 147(1):60-69.

(56) References Cited

OTHER PUBLICATIONS

Urlaub et al., "Isolation of Chinese hamster cell mutants deficient in dihydrofolate reductase activity." Proc. Natl. Acad. Sci. U.S.A., Jul. 1980, 77(7):4216-4220.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.
Vaswani et al., "Humanized antibodies as potential therapeutic drugs," Ann. Allergy, Asthma Immunol., Aug. 1998, 81(2):105-116, 119.
Verhoeyen et al., "Reshaping human antibodies: grafting an antilysozyme activity," Science, Mar. 25, 1988, 239(4847):1534-1536.
Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Wallner, Fredrik K., et al. "Solid-phase synthesis of serine-based glycosphingolipid analogues for preparation of glycoconjugate arrays." Organic & Biomolecular Chemistry 3.2 (2005): 309-315.
Wang et al., "Glycan microarray of Globo H and related structures for quantitative analysis of breast cancer," Proc. Natl. Acad. Sci. U.S.A., Aug. 19, 2008, 105(33):11661-11666.
Ward et al., "Binding activities of a repertoire of single immunoglobulin variable domains secreted from *Escherichia coli*," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Wilen et al., "Strategies in optical resolutions," Tetrahedron, 1977, 33(21):2725-2736.
Williams, S.C. and Winter, G. "Cloning and sequencing of human immunoglobulin Vλ gene segments " Eur. J. Immunol., 1993, 23: 1456-1461.
Wilman, "Prodrugs in Cancer Chemotherapy" Biochemical Society Transactions, 14, pp. 375-382, 615th Meeting Belfast, 1986.
Winter et al., "Making antibodies by phage display technology," Annu. Rev. Immunol., 1994, 12:433-455.
Wymer, Nathan et al., Enzyme-Catalyzed Synthesis of Carbohydrates, Curr. Opin. Chem. Biol., 4, 110-119, 2000.
Yaniv, Moshe, Enhancing Elements for Activation of Eukaryotic Promoters, Nature 297: 17-18, 1982.
Yansura et al., "Nucleotide sequence selection for increased expression of heterologous genes in *Escherichia coli*," Methods: A Companion to Methods in Enzymol., Aug. 1992, 4(2):151-158.
Yelton et al., "Affinity maturation of the BR96 anti-carcinoma antibody by codon-based mutagenesis." J. Immunol., Aug. 15, 1995, 155(4):1994-2004.
Zhang et al., "Selection of tumor antigens as targets for immune attack using immunohistochemistry: I. Focus on gangliosides," Int. J. Cancer, Sep. 26, 1997,73(1):42-49.
Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.
Zhu, Jianglong et al., From Synthesis to Biologies: Preclinical Data on a Chemistry Derived Anticancer Vaccine, J. Am. Chem. Soc. 131(26):9298-9303, 2009.
Eller, Chelcie et al., "Affinity of monoclonal antibodies for Globo-series glycans," Carbohydrate Research, (2014), 397, 1-6.
Lou, Yi-Wei et al., "Stage-specific embryonic antigen-4 as a potential therapeutic target in glioblastoma multiforme and other cancers," PNAS, (2014), 111(7): 2482-2487.
Gebauer, J Structrual Biology, vol. 128, p. 280-286, 1999.
Gilewski, T et al., "Immunization of of metastatic breast cancer patients with a fully synthetic globo H conjugate: A phase I trial," PNAS, 98(6), pp. 3270-3275, Mar. 13, 2001.
Sasikumar et al., "Small-Molecule Immune Checkpoint INhibitors Targeting PD-1/PD-L1 and Other Emerging Checkpoint Pathways," BioDrugs, 2018, 32:481-497.
BLAST alignment of GenBank AN126084.1 and SEQ ID No. 1 (downloaded Nov. 20, 2020). (Year: 2020).
First Examination Report dated Jul. 5, 2021 in India Patent Application No. 201717013151.
NCBI GenBank: AN126084.1 (submitted Jun. 8, 2016). (Year: 2016).
Non-Final Office Action issued in U.S. Appl. No. 14/855,260 dated Jul. 27, 2021.
Chang, W.W. et al., "Expression of Globo H and SSEA3 in breast cancer stem cells and the involvement of fucosyl transferases 1 and 2 in Globo H synthesis," PNAS, Aug. 19, 2008, vol. 105 No. 33, pp. 11667-11672.
GenBank: CAG28308.1, May 13, 2004.
GenBank: CAG28309.2, Nov. 26, 2013.
Pravetoni, M et al. "Structurally distinct nicotine immunogens elicit antibodies with non-overlapping specificities," Biochem Pharmacol, Feb. 15, 2012, vol. 83. No. 4, 543-550. 19 pages.
Sledzinska, Anna et al. "Negative immune checkpoints on T lymphocytes and their relevance to cancer immunotherapy," Molecular Oncology, 2015, vol. 9, pp. 1936-1965 (30 pages).
International Search Report dated Mar. 24, 2022, in International Patent Publication No. WO 2022/072513.
NCT01516307—Trial of Active Immunotherapy with Globo H-KLH (OPT-822) in Metastatic Breast Cancer Subjects. Full Text Review. ClinicalTrials.gov. Jan. 2012. (https://clinicaltrials.gov/ct2/show/NCT01516307).
Ragupathi, G., et al., "A fully synthetic globo H carbohydrate vaccine induces a focused humoral response in prostate cancer patients: a proof of principle," Angewandte Chemie International Edition 38.4 (1999): 569-566. Feb. 22, 1999.
Wang, Z.-G. et al., "Polyclonal antibodies from patients immunized with a globo H-keyhole limpet hemocyanin vaccine: Isolation, quantification, and characterization of immune responses by using totally synthetic immobilized tumor antigens," PNAS, Mar. 14, 2000, vol. 97, No. 6, pp. 2719-2724.

* cited by examiner

SEQUENCE LISTING

<160> NUMBER OF SEQ ID NOS: 270

<210> SEQ ID NO 1
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
cagctgcagt tgcaggagtc gggcccagga ctggtgaagc ctgcggagac cctgtccctc      60
acctgctctg tctccggtgg ctacgtcacc atcaaggata attattgggt ctggttccgc     120
cagtccccag ggaaggagcc ggagtggatt gggagtatgt cttatagtgg aatgcctac      180 tacaacccgt ccctcaagag tcgagccagc atttccatag accgtacag gaaccagttc     240 tccctgaggt tgacttctgt gaccgccgca gacacgtcca tgtactactg tgcgagacga    300
tcagcagcag ctggtggggg gaatgaatgg ttcgacccct ggggccaagg agcccttgtc    360
accgtctcct ca                                                         372
```

<210> SEQ ID NO 2
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
cagtctgctt tgacgcagcc gccctcagtg tctgcggccc caggacggaa ggtcgacatc      60
tcctgctctg gaagcacctt caatattggg aacaattatg tgtcgtggta ccggcagttc     120
ccaggaacag cccccaaact cctcatttat gacaatgata gcgaccctc aggcattcct     180 gaccgattct ctggctccag gttcggcacg tcagccaccc tgggcatcac cggactccag    240
actgacgacg aggccattta ttactgcgca acatgggata cagactgga tgctgtggtt    300 ttcggcgggg ggaccgagtt gatcgtcctt                                      330
```

<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Leu Gln Leu Gln Glu Ser Gly Pro Gly Leu Val Lys Pro Ala Glu
 1               5                  10                  15

Thr Leu Ser Leu Thr Cys Ser Val Ser Gly Gly Tyr Val Thr Ile Lys
            20                  25                  30

Asp Asn Tyr Trp Val Trp Phe Arg Gln Ser Pro Gly Lys Glu Pro Glu
        35                  40                  45

Trp Ile Gly Ser Met Ser Tyr Ser Gly Asn Ala Tyr Tyr Asn Pro Ser
    50                  55                  60

Leu Lys Ser Arg Ala Ser Ile Ser Ile Asp Arg Tyr Arg Asn Gln Phe
65                  70                  75                  80

Ser Leu Arg Leu Thr Ser Val Thr Ala Ala Asp Thr Ser Met Tyr Tyr
                85                  90                  95
```

Cys Ala Arg Arg Ser Ala Ala Ala Gly Gly Asn Glu Trp Phe Asp
            100                 105                 110

Pro Trp Gly Gln Gly Ala Leu Val Thr Val Ser Ser
        115                 120

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Ala Leu Thr Gln Pro Pro Ser Val Ser Ala Ala Pro Gly Arg
1               5                   10                  15

Lys Val Asp Ile Ser Cys Ser Gly Ser Thr Phe Asn Ile Gly Asn Asn
            20                  25                  30

Tyr Val Ser Trp Tyr Arg Gln Phe Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Arg Phe Gly Thr Ser Ala Thr Leu Gly Ile Thr Gly Leu Gln
65                  70                  75                  80

Thr Asp Asp Glu Ala Ile Tyr Tyr Cys Ala Thr Trp Asp Asn Arg Leu
                85                  90                  95

Asp Ala Val Val Phe Gly Gly Gly Thr Glu Leu Ile Val Leu
            100                 105                 110

<210> SEQ ID NO 5
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaggtgcacc tggtggagtc tgggggaggc ctggtaaacc cggggggtc ccttagactc      60 tcctgttcag cctctggctt cgctttcact accgcctgga tgacctgggc ccgccaggct    120
ccagggaagg gactggaatg gattggcctt attaaaagca caaatgatgg tgggtctata    180
gactacgctg cacccgtgca aggcagattc accatctcaa gagatgattc aaagaacacg    240
atttacctcc aaatgagcag cctcaaagcc gaggactcag ccgtctacta ttgtgccaca    300
aacgatgttg ttcggcttcg aggggttacc cccccatac ttctgtgggg ccaggggacc    360
ctgatcaccg tctcctca                                                  378

<210> SEQ ID NO 6
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cagcttgtac tgactcaatc gccctcaacc tctgcctccc tgggagcccc ggtcacactc     60
acctgcactc tgagcagtgg gcaccacagc taccccgtcg catggcatca gaagcaccca    120
gagaagggcc ctcgatactt gatgaagatt aacggagatg gcagccacac caaggggac    180

```
ggtatccctg atcgcttctc aggctccagc tctgggactg ggcgctatct caccatctcc      240
agcctccagt ctgaggatga ggctgactat tactgtcaga cctgggccac tggatgggtg      300
ttcggcggag ggaccaaact gaccgtccta                                        330
```

<210> SEQ ID NO 7
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Glu Val His Leu Val Glu Ser Gly Gly Gly Leu Val Asn Pro Gly Gly
1               5                   10                  15

Ser Leu Arg Leu Ser Cys Ser Ala Ser Gly Phe Ala Phe Thr Thr Ala
            20                  25                  30

Trp Met Thr Trp Ala Arg Gln Ala Pro Gly Lys Gly Leu Glu Trp Ile
        35                  40                  45

Gly Leu Ile Lys Ser Thr Asn Asp Gly Gly Ser Ile Asp Tyr Ala Ala
    50                  55                  60

Pro Val Gln Gly Arg Phe Thr Ile Ser Arg Asp Asp Ser Lys Asn Thr
65                  70                  75                  80

Ile Tyr Leu Gln Met Ser Ser Leu Lys Ala Glu Asp Ser Ala Val Tyr
                85                  90                  95

Tyr Cys Ala Thr Asn Asp Val Val Arg Leu Arg Gly Val Thr Pro Pro
            100                 105                 110

Ile Leu Leu Trp Gly Gln Gly Thr Leu Ile Thr Val Ser Ser
        115                 120                 125
```

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gln Leu Val Leu Thr Gln Ser Pro Ser Thr Ser Ala Ser Leu Gly Ala
1               5                   10                  15

Pro Val Thr Leu Thr Cys Thr Leu Ser Ser Gly His His Ser Tyr Pro
            20                  25                  30

Val Ala Trp His Gln Lys His Pro Glu Lys Gly Pro Arg Tyr Leu Met
        35                  40                  45

Lys Ile Asn Gly Asp Gly Ser His Thr Lys Gly Asp Gly Ile Pro Asp
    50                  55                  60

Arg Phe Ser Gly Ser Ser Ser Gly Thr Gly Arg Tyr Leu Thr Ile Ser
65                  70                  75                  80

Ser Leu Gln Ser Glu Asp Glu Ala Asp Tyr Tyr Cys Gln Thr Trp Ala
                85                  90                  95

Thr Gly Trp Val Phe Gly Gly Gly Thr Lys Leu Thr Val Leu
            100                 105                 110
```

<210> SEQ ID NO 9
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gagttgcagt tggtggagtc tgggggaaag ttggtaaatc cggggggtc cctgagactc     60 tcatgtgcag cctctggatt cactttccct aacgcctggt ttaactgggt ccgccagact    120
ccagggaggg ggctggagtg ggttgcccgt attaaaagtc attctgacgg tgggacagcc    180
gactacgctg cacccgtgaa aggcagattc accgtctcaa gggatgattc agagaacatg    240
gtgtttctgc aaatgaaccg cctgcgtgcc gaggacacag ccgttttatta ttgtactacc    300 ttggagattt atcaccctgt ggacgtctgg ggccagggga ccacggtcgc cgtctcctca    360

<210> SEQ ID NO 10
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gatgttgtgc tgactcagtc tccactctcc ctgtccgtca cccttggaca gccggcctcc     60
atctcctgca ggtccagtca cagcctccca gagatgatg aatactccta cctgaattgg    120
tttcagcaga ggccaggcca gtctccaagg cgcctaattt atagggtttc taagcgggac    180
tctggggtcc cagacagatt cagcggcagt gggtcagaca cttatttcac actgacaatc    240
agcagggtgg aggctgagga tgttggagtt tattactgca tgcaaggtac atactggccc    300
gggacgttcg gccaagggac gaagttggaa atcgagcga                           339

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Leu Gln Leu Val Glu Ser Gly Gly Lys Leu Val Asn Pro Gly Gly
1               5                   10                  15

Ser Leu Arg Leu Ser Cys Ala Ala Ser Gly Phe Thr Phe Pro Asn Ala
            20                  25                  30

Trp Phe Asn Trp Val Arg Gln Thr Pro Gly Arg Gly Leu Glu Trp Val
        35                  40                  45

Ala Arg Ile Lys Ser His Ser Asp Gly Gly Thr Ala Asp Tyr Ala Ala
    50                  55                  60

Pro Val Lys Gly Arg Phe Thr Val Ser Arg Asp Asp Ser Glu Asn Met
65                  70                  75                  80

Val Phe Leu Gln Met Asn Arg Leu Arg Ala Glu Asp Thr Ala Val Tyr
                85                  90                  95

Tyr Cys Thr Thr Leu Glu Ile Tyr His Pro Val Asp Val Trp Gly Gln
            100                 105                 110

Gly Thr Thr Val Ala Val Ser Ser
        115                 120

<210> SEQ ID NO 12
<211> LENGTH: 113

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Val Val Leu Thr Gln Ser Pro Leu Ser Leu Ser Val Thr Leu Gly
1               5                   10                  15

Gln Pro Ala Ser Ile Ser Cys Arg Ser Ser His Ser Leu Pro Arg Asp
            20                  25                  30

Asp Glu Tyr Ser Tyr Leu Asn Trp Phe Gln Gln Arg Pro Gly Gln Ser
        35                  40                  45

Pro Arg Arg Leu Ile Tyr Arg Val Ser Lys Arg Asp Ser Gly Val Pro
    50                  55                  60

Asp Arg Phe Ser Gly Ser Gly Ser Asp Thr Tyr Phe Thr Leu Thr Ile
65                  70                  75                  80

Ser Arg Val Glu Ala Glu Asp Val Gly Val Tyr Tyr Cys Met Gln Gly
                85                  90                  95

Thr Tyr Trp Pro Gly Thr Phe Gly Gln Gly Thr Lys Leu Glu Ile Glu
            100                 105                 110

Arg

<210> SEQ ID NO 13
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaggtgcacc tggtggagtc tgggggaggc ctcgtaaacc cggggggggtc ccttagactc      60 tcctgtacag cctctggatt cactttcatc accgcctgga tgacctgggc ccgccaggct     120
ccagggaggg ggctggagtg gattggactt attaaaagcg gaaatgatgg tggggctata     180
gagtacgctg cacccgtgaa aggcagattc accatctcaa gagatgattc aaggaatatg     240
atttatctac aaatgaataa tgtcaaagcc gaggacgcag ccgtctacta ttgtgccaca     300
aacgatgttg ctttggtttg gggagttacc ccccccttgc ttctctgggg ccaggggacc     360
cgggtcaccg tctcttca                                                    378

<210> SEQ ID NO 14
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
caacttgtgg tgactcaatc gccctctgcc tctgcctccc tgggaggctc ggtcaagctc      60
acctgcactc tgagcagtgg gcacggcaac taccccgtcg catggcatca gctccaccca     120
gcgaagggcc ctcgatactt gatgaagctt aatgcagatg cagccacat caaggggggcc     180 gggatcactg atcgcttctc aggcttcagg tctgggctg agcgctacct caccatctcc     240
agcctccagt ctgaagatga ggctgattat tactgtcaga cctgggcccc tggatgggtg     300
ctcggcggag ggaccaagct gaccgtccta                                       330
```

<210> SEQ ID NO 15
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val His Leu Val Glu Ser Gly Gly Gly Leu Val Asn Pro Gly Gly
1               5                   10                  15

Ser Leu Arg Leu Ser Cys Thr Ala Ser Gly Phe Thr Phe Ile Thr Ala
            20                  25                  30

Trp Met Thr Trp Ala Arg Gln Ala Pro Gly Arg Gly Leu Glu Trp Ile
        35                  40                  45

Gly Leu Ile Lys Ser Gly Asn Asp Gly Gly Ala Ile Glu Tyr Ala Ala
    50                  55                  60

Pro Val Lys Gly Arg Phe Thr Ile Ser Arg Asp Asp Ser Arg Asn Met
65                  70                  75                  80

Ile Tyr Leu Gln Met Asn Asn Val Lys Ala Glu Asp Ala Ala Val Tyr
                85                  90                  95

Tyr Cys Ala Thr Asn Asp Val Ala Leu Val Trp Gly Val Thr Pro Pro
            100                 105                 110

Leu Leu Leu Trp Gly Gln Gly Thr Arg Val Thr Val Ser Ser
        115                 120                 125

<210> SEQ ID NO 16
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Leu Val Val Thr Gln Ser Pro Ser Ala Ser Ala Ser Leu Gly Gly
1               5                   10                  15

Ser Val Lys Leu Thr Cys Thr Leu Ser Ser Gly His Gly Asn Tyr Pro
            20                  25                  30

Val Ala Trp His Gln Leu His Pro Ala Lys Gly Pro Arg Tyr Leu Met
        35                  40                  45

Lys Leu Asn Ala Asp Gly Ser His Ile Lys Gly Ala Gly Ile Thr Asp
    50                  55                  60

Arg Phe Ser Gly Phe Arg Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Ala
                85                  90                  95

Pro Gly Trp Val Leu Gly Gly Gly Thr Lys Leu Thr Val Leu
            100                 105                 110

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
caggtgcaac tggtggagtg ggggggaggc gtggcccagc ctgggacgtc cctgaggctc      60
acctgtgatg cgtctggatt cagcttcaga cattatggca tgcactgggt ccgccaggct    120
ccaggcaagg ggctggagtg ggtggcagtt atctggcata atggaagaga cagagagtat    180
gcagactccg tgaagggccg cttcaccatc tccagagaca attccaagta caccctgtct    240
ttacaaatga acagcctgac agtcgaagac acggcattat attactgcgg gagagatcga    300
ggtgaagacg agccgattga cttttggggc cagggaaccc tggtcaccgt ctcttca       357
```

<210> SEQ ID NO 18
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
caggctgtgc tgactcaacc gtcttccctc tctgcatctc ctggagcatc agccagtctc     60
acctgcacct gcgcagtgg cctcagtgct ggtcccaagt ggatatactg gtaccagcag    120
agggcaggga gtcctcccca atttctcctg acatacaaat cagactcaga gagcggcgg    180
agctctggac tccccagccg cttctctgga tccaaggatg gctcggccaa tgcagggatt    240
ttactcatct ctgggctcca atctgaagat gaggcagact attactgtgc gatttggcac    300
agcaacgttg tctttttcgg cgcagggacc aggttgaccg tcctg                    345
```

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Gln Val Gln Leu Val Glu Trp Gly Gly Gly Val Ala Gln Pro Gly Thr
  1               5                  10                  15
Ser Leu Arg Leu Thr Cys Asp Ala Ser Gly Phe Ser Phe Arg His Tyr
             20                  25                  30
Gly Met His Trp Val Arg Gln Ala Pro Gly Lys Gly Leu Glu Trp Val
         35                  40                  45
Ala Val Ile Trp His Asn Gly Arg Asp Arg Glu Tyr Ala Asp Ser Val
     50                  55                  60
Lys Gly Arg Phe Thr Ile Ser Arg Asp Asn Ser Lys Tyr Thr Leu Ser
 65                  70                  75                  80
Leu Gln Met Asn Ser Leu Thr Val Glu Asp Thr Ala Leu Tyr Tyr Cys
                 85                  90                  95
Gly Arg Asp Arg Gly Glu Asp Glu Pro Ile Asp Phe Trp Gly Gln Gly
            100                 105                 110
Thr Leu Val Thr Val Ser Ser
        115
```

<210> SEQ ID NO 20
<211> LENGTH: 115
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 20

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Leu Ser Ala Gly Pro
            20                  25                  30

Lys Trp Ile Tyr Trp Tyr Gln Gln Arg Ala Gly Ser Pro Pro Gln Phe
        35                  40                  45

Leu Leu Thr Tyr Lys Ser Asp Ser Glu Glu Arg Arg Ser Ser Gly Leu
    50                  55                  60

Pro Ser Arg Phe Ser Gly Ser Lys Asp Gly Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Ala Ile Trp His Ser Asn Val Val Phe Phe Gly Ala Gly Thr Arg Leu
            100                 105                 110

Thr Val Leu
        115

<210> SEQ ID NO 21
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gaggtgcgcc tggtggagtc tgggggaggc ttaatagagc cggggggggtc tcttagactc      60 tcatgtgaag cctctggatt cgttttcact accgcctgga tgaattgggt ccgccaggct     120
ccagggaagg ggctggagtg ggttggccgt attaagagca aaaatgaggc tgagacaaca     180
gactacgctg cacccgtgaa aggcagattc accatctcaa gagatgattc aaaggacaca     240
ttgtatctgc aaatgaacaa cctgaaaacc gaagacacag ccgtctatta ttgtaccaca     300
cttgagacgt attacgagtc cgacttctgg ggccagggag tcctggtcgc cgtctcctca     360

<210> SEQ ID NO 22
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gatgttgtga tgactcagtc tccactctcc ctgaccgtca ctcttggaca gccggcctcc      60
atctcctgca ggtctagtca agcctcgcga gagagaaag aggacatctt gttaaactgg     120
tatcaccagg ggccaggcca atctcccagg cgcctaattt atagagtttc taagcgtgag     180
tctggggtcc caaataaatt cagcggcagt gtgtcaggca ctgatttcac cctgagaatc     240
agcagggtgg aggctgagga tgttggggtt tattactgca tgcaacgaac acactggcct     300
cagacttttg gccaggggac caagctggag atcagacga                           339

<210> SEQ ID NO 23
<211> LENGTH: 120
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 23

Glu Val Arg Leu Val Glu Ser Gly Gly Gly Leu Ile Glu Pro Gly Gly
1               5                   10                  15

Ser Leu Arg Leu Ser Cys Glu Ala Ser Gly Phe Val Phe Thr Thr Ala
            20                  25                  30

Trp Met Asn Trp Val Arg Gln Ala Pro Gly Lys Gly Leu Glu Trp Val
        35                  40                  45

Gly Arg Ile Lys Ser Lys Asn Glu Ala Glu Thr Thr Asp Tyr Ala Ala
    50                  55                  60

Pro Val Lys Gly Arg Phe Thr Ile Ser Arg Asp Asp Ser Lys Asp Thr
65                  70                  75                  80

Leu Tyr Leu Gln Met Asn Asn Leu Lys Thr Glu Asp Thr Ala Val Tyr
                85                  90                  95

Tyr Cys Thr Thr Leu Glu Thr Tyr Tyr Glu Ser Asp Phe Trp Gly Gln
            100                 105                 110

Gly Val Leu Val Ala Val Ser Ser
        115                 120

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Val Val Met Thr Gln Ser Pro Leu Ser Leu Thr Val Thr Leu Gly
1               5                   10                  15

Gln Pro Ala Ser Ile Ser Cys Arg Ser Ser Gln Ser Leu Ala Glu Arg
            20                  25                  30

Glu Glu Asp Ile Leu Leu Asn Trp Tyr His Gln Gly Pro Gly Gln Ser
        35                  40                  45

Pro Arg Arg Leu Ile Tyr Arg Val Ser Lys Arg Glu Ser Gly Val Pro
    50                  55                  60

Asn Lys Phe Ser Gly Ser Val Ser Gly Thr Asp Phe Thr Leu Arg Ile
65                  70                  75                  80

Ser Arg Val Glu Ala Glu Asp Val Gly Val Tyr Tyr Cys Met Gln Arg
                85                  90                  95

Thr His Trp Pro Gln Thr Phe Gly Gln Gly Thr Lys Leu Glu Ile Arg
            100                 105                 110

Arg

<210> SEQ ID NO 25
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
caggtgcagc tggtggagtg ggggggaggc gtggtccagc ctggggggtc cctgagactt      60
tgctgtgcag cgtctggatt cagtttaagg agttttggca tgcactgggt ccgtcaggct    120
```

```
ccaggcaagg ggctggaatg ggtggcagtt atttggcccc gacgaagtca aatacaatat      180
gcagactccg tgaagggccg agtcaccatc tccagagacg actctaggag tacggtatgt      240
ctgcagatga acagcctgag agtcgaggac acggctctct atcgctgtgc gagagacccc      300
ggtgaggaca atcccataga ttactggggc cagggaaccc tggtcatcgt ctcctca        357
```

<210> SEQ ID NO 26
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
caggctgtgc tgactcagcc gtcttccctc tctgcatctc ctggagcatc agccagtctc       60
acctgcacct tcctcagcgg catcaatgtt ggtccctact ggatatactg gtaccagcaa      120
aagccaggga gtcctcccca gtttctcctg aggtacaagt cagactcaga taagcaccag      180
ggctctgaag tccccagccg cttctctgga tccaaagatg cttcggccaa tgcagggatt      240
ttactcatct ctgggctcca gtctgaagat gaggctgact attactgtat gatctggcac      300
gtcagcggtg tgattttcgg cggagggacc aagctgaccg tccta                     345
```

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Val Gln Leu Val Glu Trp Gly Gly Gly Val Val Gln Pro Gly Gly
1               5                   10                  15

Ser Leu Arg Leu Cys Cys Ala Ala Ser Gly Phe Ser Leu Arg Ser Phe
            20                  25                  30

Gly Met His Trp Val Arg Gln Ala Pro Gly Lys Gly Leu Glu Trp Val
        35                  40                  45

Ala Val Ile Trp Pro Arg Arg Ser Gln Ile Gln Tyr Ala Asp Ser Val
    50                  55                  60

Lys Gly Arg Val Thr Ile Ser Arg Asp Asp Ser Arg Ser Thr Val Cys
65                  70                  75                  80

Leu Gln Met Asn Ser Leu Arg Val Glu Asp Thr Ala Leu Tyr Arg Cys
                85                  90                  95

Ala Arg Asp Pro Gly Glu Asp Asn Pro Ile Asp Tyr Trp Gly Gln Gly
            100                 105                 110

Thr Leu Val Ile Val Ser Ser
        115
```

<210> SEQ ID NO 28
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ala Val Leu Thr Gln Pro Ser Ser Leu Ser Ala Ser Pro Gly Ala
1               5                   10                  15

Ser Ala Ser Leu Thr Cys Thr Phe Leu Ser Gly Ile Asn Val Gly Pro
            20                  25                  30

Tyr Trp Ile Tyr Trp Tyr Gln Gln Lys Pro Gly Ser Pro Pro Gln Phe
        35                  40                  45

Leu Leu Arg Tyr Lys Ser Asp Ser Asp Lys His Gln Gly Ser Glu Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Val Ser Gly Val Ile Phe Gly Gly Gly Thr Lys Leu
            100                 105                 110

Thr Val Leu
        115

<210> SEQ ID NO 29
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caggtgcaac tggtggagtg ggggggaggc gtggtccagc ctgggacgtc cctgagactc     60
acctgtgatg cgtctggatt cagcttcaga cattatggca tgcactgggt ccgccaggct   120
ccaggcaagg ggctggagtg ggtggcagtt atctggcata tggaagaga taaagactat    180 gcagactccg tgaagggccg gttcaccatc tccagagaca attccaagta caccctgtct   240
ttacaaatga acagcctgac agtcgaggac acggcattat attactgtgg gagagatcga   300
ggtgaagacg agccgattga cttttggggc cagggaaccc tggtcaccgt ctcctca      357

<210> SEQ ID NO 30
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
caggctgtgc tgactcaacc gtcttccctc tctgcatctc ctggagcatc agccagtctc     60
acctgcacct tgcgcagtgg cctcaatgtt ggtccctact ggatatactg gtaccagcag   120
aaggcaggga gtcctcccca atttctcctg agatacaaat cagactcaga aaagcggcgg   180
agctctggag tccccagccg cttctctgga tccaaagatg cctcggccaa tgcagggatt   240
ttactcatct ctgggctcca gtctgaagat gaggctgact attattgtgc gatttggcac   300
agcaatgctg tcttttttcgg cgcagggacc aagttgaccg tccta                   345

<210> SEQ ID NO 31
<211> LENGTH: 119
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 31

Gln Val Gln Leu Val Glu Trp Gly Gly Gly Val Val Gln Pro Gly Thr
1               5                   10                  15

Ser Leu Arg Leu Thr Cys Asp Ala Ser Gly Phe Ser Phe Arg His Tyr
            20                  25                  30

Gly Met His Trp Val Arg Gln Ala Pro Gly Lys Gly Leu Glu Trp Val
        35                  40                  45

Ala Val Ile Trp His Asn Gly Arg Asp Lys Asp Tyr Ala Asp Ser Val
    50                  55                  60

Lys Gly Arg Phe Thr Ile Ser Arg Asp Asn Ser Lys Tyr Thr Leu Ser
65                  70                  75                  80

Leu Gln Met Asn Ser Leu Thr Val Glu Asp Thr Ala Leu Tyr Tyr Cys
                85                  90                  95

Gly Arg Asp Arg Gly Glu Asp Glu Pro Ile Asp Phe Trp Gly Gln Gly
            100                 105                 110

Thr Leu Val Thr Val Ser Ser
        115

<210> SEQ ID NO 32
<211> LENGTH: 115
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 32

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Leu Asn Val Gly Pro
            20                  25                  30

Tyr Trp Ile Tyr Trp Tyr Gln Gln Lys Ala Gly Ser Pro Pro Gln Phe
        35                  40                  45

Leu Leu Arg Tyr Lys Ser Asp Ser Glu Lys Arg Arg Ser Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Ala Ile Trp His Ser Asn Ala Val Phe Phe Gly Ala Gly Thr Lys Leu
            100                 105                 110

Thr Val Leu
        115

<210> SEQ ID NO 33
<211> LENGTH: 357
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33
caggtgcaga tggtggagtt tgggggaggc atcttccagc ctgggggtc cctgagactc      60 tcctgtgtcg cgtctggatt ccccttcagg tactatggtt ccactgggt ccgccagact     120

```
ccaggcaagg ggctggagtg gctggcagtt gtatggcaca atggaaggga gacatattat    180
gaagactccg tgaagggcg attcaccatc tccagagaca attacaagaa cacgctgtat    240
ttgcaaatgg acagcctgag agtcgaggac acggctgtct atcactgtgc gagagatcgt    300
ggtagcgacg aaccaattga ctactggggc caggagtttt ggtcaccgt ctcctca       357
```

<210> SEQ ID NO 34
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
caggctgtgc tgactcagcc gtcctccctc tctgcatctc ctggagcatc agccagtatc    60
acctgcacct tacgcagtga cctcactgtt ggtccctact ggatgtactg gtaccaacag    120
aagccaggga gtcctcccca atttctcctg aggtacaagt cagactccga aaagtatcag    180
ggctctggag tccccagccg cttctctgga tccaaagacg cttcggccaa tgcagggact    240
ttgctcatct ctggactcca gtctgaagat gaggctgact attactgtca gacttggcac    300
gccaacactg tggtatttgg cggagggacc aagctgaccg tccta                   345
```

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Met Val Glu Phe Gly Gly Gly Ile Phe Gln Pro Gly Gly
1               5                   10                  15

Ser Leu Arg Leu Ser Cys Val Ala Ser Gly Phe Pro Phe Arg Tyr Tyr
            20                  25                  30

Gly Phe His Trp Val Arg Gln Thr Pro Gly Lys Gly Leu Glu Trp Leu
        35                  40                  45

Ala Val Val Trp His Asn Gly Arg Glu Thr Tyr Tyr Glu Asp Ser Val
    50                  55                  60

Lys Gly Arg Phe Thr Ile Ser Arg Asp Asn Tyr Lys Asn Thr Leu Tyr
65                  70                  75                  80

Leu Gln Met Asp Ser Leu Arg Val Glu Asp Thr Ala Val Tyr His Cys
                85                  90                  95

Ala Arg Asp Arg Gly Ser Asp Glu Pro Ile Asp Tyr Trp Gly Gln Gly
            100                 105                 110

Val Leu Val Thr Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ala Val Leu Thr Gln Pro Ser Ser Leu Ser Ala Ser Pro Gly Ala
1               5                   10                  15

Ser Ala Ser Ile Thr Cys Thr Leu Arg Ser Asp Leu Thr Val Gly Pro
            20                  25                  30

Tyr Trp Met Tyr Trp Tyr Gln Gln Lys Pro Gly Ser Pro Pro Gln Phe
        35                  40                  45

Leu Leu Arg Tyr Lys Ser Asp Ser Glu Lys Tyr Gln Gly Ser Gly Val
50                  55                  60

Pro Ser Arg Phe Ser Gly Ser Lys Asp Ala Ser Ala Asn Ala Gly Thr
65                  70                  75                  80

Leu Leu Ile Ser Gly Leu Gln Ser Glu Asp Glu Ala Asp Tyr Tyr Cys
                85                  90                  95

Gln Thr Trp His Ala Asn Thr Val Val Phe Gly Gly Gly Thr Lys Leu
            100                 105                 110

Thr Val Leu
        115

<210> SEQ ID NO 37
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
caggtgcagc tggtggagtc tgggggaggc gtcttccagc cggggggtc cctgagactc      60 tcctgtgcag cgtctggatt cagtttcagg agatttggta tgcattgggt ccgccaggct    120
ccaggcaagg ggctggagtg gctggcagtt gtttggcatg atggaaggga gacacactat    180
ggagactccg tgaggggccg attcaccatc tccagagaca actccatgca catggtgttt    240
ttggacatgt acagcctgag ggtcgaggac acggctctat atcgctgtgc gagagatcct    300
ggtcaggacg aagccattga ctattgggc cagggagtcc tggtcaccgt ctcgtca       357

<210> SEQ ID NO 38
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
caggctgtgc tgactcagcc gtcttccctc tctgcatctc ctggagcatc agccagtctc      60
acctgcacct tacacagtgg cctcactgtt ggtccctatt ggatatactg gttccggcag    120
aagccaggga gtcccccca gtttctcctc aggtacaaat ccgactcaga ggagtaccgt    180
gcctctggag tccccagccg cttctctgga tccaaagatg cttcggccaa tcaggcatt    240 ttactcatct ctggaccaca gtctgaagac gaggctgact attactgtat gacttggcac    300
accaacaagg tagtcttcgg cggagggacc acactgaccg tccta                    345

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Ser Gly Gly Val Phe Gln Pro Gly Gly
1               5                   10                  15

Ser Leu Arg Leu Ser Cys Ala Ala Ser Gly Phe Ser Phe Arg Arg Phe
            20                  25                  30

Gly Met His Trp Val Arg Gln Ala Pro Gly Lys Gly Leu Glu Trp Leu
        35                  40                  45

Ala Val Val Trp His Asp Gly Arg Glu Thr His Tyr Gly Asp Ser Val
    50                  55                  60

Arg Gly Arg Phe Thr Ile Ser Arg Asp Asn Ser Met His Met Val Phe
65                  70                  75                  80

Leu Asp Met Tyr Ser Leu Arg Val Glu Asp Thr Ala Leu Tyr Arg Cys
                85                  90                  95

Ala Arg Asp Pro Gly Gln Asp Glu Ala Ile Asp Tyr Trp Gly Gln Gly
            100                 105                 110

Val Leu Val Thr Val Ser Ser
        115

<210> SEQ ID NO 40
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ala Val Leu Thr Gln Pro Ser Ser Leu Ser Ala Ser Pro Gly Ala
1               5                   10                  15

Ser Ala Ser Leu Thr Cys Thr Leu His Ser Gly Leu Thr Val Gly Pro
            20                  25                  30

Tyr Trp Ile Tyr Trp Phe Arg Gln Lys Pro Gly Ser Pro Gln Phe
        35                  40                  45

Leu Leu Arg Tyr Lys Ser Asp Ser Glu Glu Tyr Arg Ala Ser Gly Val
    50                  55                  60

Pro Ser Arg Phe Ser Gly Ser Lys Asp Ala Ser Ala Asn Ser Gly Ile
65                  70                  75                  80

Leu Leu Ile Ser Gly Pro Gln Ser Glu Asp Glu Ala Asp Tyr Tyr Cys
                85                  90                  95

Met Thr Trp His Thr Asn Lys Val Val Phe Gly Gly Gly Thr Thr Leu
            100                 105                 110

Thr Val Leu
        115

<210> SEQ ID NO 41
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtgcagc tggtgcagtc tggggctgag gtgaagaagc ctggggcctc agtgaaggtc     60
tcctgccagg cttctggata caccttcacc aactatggtg tcaactgggt gcgacaggcc    120
actggacaag ggcttgagtg gatgggatgg atgaacacta cagtggtga cacgggttat    180

```
gcccagaagt tccagggcag agtcaccatg accagggaca cctccataaa cacagcctac    240
atggagctga gcggactgac atctgaggac acggccgtct attactgtgc gcgagcgtat    300
ttttttgatt cgtggaataa gggcaactgg ttcgacccct ggggccaggg aaccccggtc    360
accgtctcct ca                                                        372
```

<210> SEQ ID NO 42
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
cagtctgtgc tgactcaggc accctcagtg tctgggaccc ccgggcagag ggtcaccatc    60
tcttgttctg gaggcagctc aacctgggga agaagttata tatattggta ccaacagttc    120
ccaggaacgg ccccccagagt cctcatttat aaaaatagtc agcggccctc aggggtccct    180
gaccgattct ccggctccaa gtctggcacc tcagcctccc tggccatcag tgggctccgg    240
tccgaggatg aggctcatta ttactgtgca gcatgggatg acagcctgag tgggtcttgg    300
gtgttcggcg gagggaccaa gctgaccgtc cta                                 333
```

<210> SEQ ID NO 43
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Asn Tyr
            20                  25                  30

Gly Val Asn Trp Val Arg Gln Ala Thr Gly Gln Gly Leu Glu Trp Met
        35                  40                  45

Gly Trp Met Asn Thr Asn Ser Gly Asp Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Gly Leu Thr Ser Glu Asp Thr Ala Val Tyr Tyr Cys
                85                  90                  95

Ala Arg Ala Tyr Phe Phe Asp Ser Trp Asn Lys Gly Asn Trp Phe Asp
            100                 105                 110

Pro Trp Gly Gln Gly Thr Pro Val Thr Val Ser Ser
        115                 120
```

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gln Ser Val Leu Thr Gln Ala Pro Ser Val Ser Gly Thr Pro Gly Gln
1               5                   10                  15
```

```
Arg Val Thr Ile Ser Cys Ser Gly Gly Ser Ser Asn Leu Gly Arg Ser
             20                  25                  30

Tyr Ile Tyr Trp Tyr Gln Gln Phe Pro Gly Thr Ala Pro Arg Val Leu
         35                  40                  45

Ile Tyr Lys Asn Ser Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala His Tyr Tyr Cys Ala Ala Trp Asp Asp Ser Leu
                 85                  90                  95

Ser Gly Ser Trp Val Phe Gly Gly Gly Thr Lys Leu Thr Val Leu
            100                 105                 110
```

<210> SEQ ID NO 45
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

| | | |
|---|---|---|
| caggtgcagt tggtggagtt tgggggaggc attttcgagc ctggggggtc cctgagactc | 60 |
| tcctgtgtcg cgtctggatt ctccttcagg cattatggta tgcactgggt ccgccaggct | 120 |
| ccaggcaagg ggctggagtg gctggcagtt gtatggcatg atggaaggga gacacattat | 180 |
| ggagactccg tgaaggggcg attcaccatc tccagagaca attacaagaa tacgctgttt | 240 |
| ttgcaaatgg acagcctgag agtcgaggac acggctgtct atcactgtgc gagagatcgt | 300 |
| ggtagcgacg aacctattga ctactggggc cagggagttt ggtcaccgt ctcctca | 357 |

<210> SEQ ID NO 46
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

| | | |
|---|---|---|
| caggctgtgc tgactcagcc gtcctccctc tctgcatctc tggagcatc agccagtatc | 60 |
| acctgcacct tacgcagtga cgtcactgtt agtccctgga catactggta ccaacagaag | 120 |
| ccagggagtc ctccccgatt tctcctgaga tacaaatcag actctgataa gtatcagggc | 180 |
| tctggagtcc ccagccgctt ctctggatcc aaaaatgctt cggccaatgc agcgatttta | 240 |
| ctcatctctg ggctccagtc tgaagatgag gctgactatt actgtcagac ttggcacacc | 300 |
| accactgtgg tatttggcgg agggaccaag ctgaccgtcc ta | 342 |

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Val Gln Leu Val Glu Phe Gly Gly Gly Ile Phe Glu Pro Gly Gly
 1               5                  10                  15
```

Ser Leu Arg Leu Ser Cys Val Ala Ser Gly Phe Ser Phe Arg His Tyr
            20                  25                  30

Gly Met His Trp Val Arg Gln Ala Pro Gly Lys Gly Leu Glu Trp Leu
        35                  40                  45

Ala Val Val Trp His Asp Gly Arg Glu Thr His Tyr Gly Asp Ser Val
    50                  55                  60

Lys Gly Arg Phe Thr Ile Ser Arg Asp Asn Tyr Lys Asn Thr Leu Phe
65                  70                  75                  80

Leu Gln Met Asp Ser Leu Arg Val Glu Asp Thr Ala Val Tyr His Cys
                85                  90                  95

Ala Arg Asp Arg Gly Ser Asp Glu Pro Ile Asp Tyr Trp Gly Gln Gly
            100                 105                 110

Val Leu Val Thr Val Ser Ser
        115

<210> SEQ ID NO 48
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ala Val Leu Thr Gln Pro Ser Ser Leu Ser Ala Ser Pro Gly Ala
1               5                   10                  15

Ser Ala Ser Ile Thr Cys Thr Leu Arg Ser Asp Val Thr Val Ser Pro
            20                  25                  30

Trp Thr Tyr Trp Tyr Gln Gln Lys Pro Gly Ser Pro Pro Arg Phe Leu
        35                  40                  45

Leu Arg Tyr Lys Ser Asp Ser Asp Lys Tyr Gln Gly Ser Gly Val Pro
    50                  55                  60

Ser Arg Phe Ser Gly Ser Lys Asn Ala Ser Ala Asn Ala Ala Ile Leu
65                  70                  75                  80

Leu Ile Ser Gly Leu Gln Ser Glu Asp Glu Ala Asp Tyr Tyr Cys Gln
                85                  90                  95

Thr Trp His Thr Thr Val Val Phe Gly Gly Gly Thr Lys Leu Thr
            100                 105                 110

Val Leu

<210> SEQ ID NO 49
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
caggtgcagc tggtgcagtc tggggctgag attaagaggc ctggggcctc agtgaaggtc    60
tcctgcaagg cgtctggata cactttcacc agctttggta tcaactgggt gcgacaggcc   120
cctggacaag gcttgagtg gatgggatgg atgaactcca acagtggtga tcggactct    180 gcacagaagt tccagggcag actcactatg accaccgaca cctccacaag tacagcctac   240
atggagctga ggaatctgag atctgaggac acggccgtat attattgcgc gagaatgaat   300
ttccgtggtt cgaagtggga ggtgaactgg ttcgacccct ggggccaggg aaccctgatc   360
accgtctcct ca                                                       372

```
<210> SEQ ID NO 50
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cagtctgtgg tgactcagcc accctcagcg tctgggaccc ccgggcagag ggtcaccatc    60
tcctgttctg gaagcaggtc caacgtcgaa agaaattttg tttactggta ccagcaactc   120
ccaggaacgg cccccaaact tctcatctat atgaacagta gcggccctc  aggggtccct   180 gaccgattct ctggctctcg ttctggcacc tcagcctccc tggccatcac tgggcttcgg   240
tccgaggatg aggctgacta ttattgtgca acttgggatg acaatctgag aggctgggtg   300
ttcggcggag ggaccaaggt gaccgtccta                                    330

<210> SEQ ID NO 51
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Ile Lys Arg Pro Gly Ala
1               5                   10                  15

Ser Val Lys Val Ser Cys Lys Ala Ser Gly Tyr Thr Phe Thr Ser Phe
            20                  25                  30

Gly Ile Asn Trp Val Arg Gln Ala Pro Gly Gln Gly Leu Glu Trp Met
        35                  40                  45

Gly Trp Met Asn Ser Asn Ser Gly Asp Ala Asp Ser Ala Gln Lys Phe
    50                  55                  60

Gln Gly Arg Leu Thr Met Thr Thr Asp Thr Ser Thr Ser Thr Ala Tyr
65                  70                  75                  80

Met Glu Leu Arg Asn Leu Arg Ser Glu Asp Thr Ala Val Tyr Tyr Cys
                85                  90                  95

Ala Arg Met Asn Phe Arg Gly Ser Lys Trp Glu Val Asn Trp Phe Asp
            100                 105                 110

Pro Trp Gly Gln Gly Thr Leu Ile Thr Val Ser Ser
        115                 120

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Ser Val Val Thr Gln Pro Pro Ser Ala Ser Gly Thr Pro Gly Gln
1               5                   10                  15

Arg Val Thr Ile Ser Cys Ser Gly Ser Arg Ser Asn Val Glu Arg Asn
            20                  25                  30

Phe Val Tyr Trp Tyr Gln Gln Leu Pro Gly Thr Ala Pro Lys Leu Leu
        35                  40                  45
```

```
Ile Tyr Met Asn Ser Gln Arg Pro Ser Gly Val Pro Asp Arg Phe Ser
 50                  55                  60
```

```
Gly Ser Arg Ser Gly Thr Ser Ala Ser Leu Ala Ile Thr Gly Leu Arg
 65                  70                  75                  80
```

```
Ser Glu Asp Glu Ala Asp Tyr Tyr Cys Ala Thr Trp Asp Asp Asn Leu
                 85                  90                  95
```

```
Arg Gly Trp Val Phe Gly Gly Gly Thr Lys Val Thr Val Leu
            100                 105                 110
```

<210> SEQ ID NO 53
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caggtgcagc tggtgcagtc tggggctgag attaagaggc ctggggcctc agtgaaggtc    60
tcctgcaagg cgtctggata caccttcacc aggttcggca tcaactgggt gcgacaggcc   120
cctggacaag gcttgagtg gatgggatgg atgaactcca acagtggtaa tgcggactct   180
gcacagaagt tccagggcag actcactatg accaccgaca cctccacaag tacagcctac   240
atggagctga ggaatctaag atctgaggac acggccgtat attattgcgc gagaatgaat   300
taccgtggtt cgaagtggga aataaactgg ttcgacccct ggggccaggg aaccctgatc   360
accgtctcct ca                                                       372

<210> SEQ ID NO 54
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
cagtctgtgg tgactcagcc accctcagcg tctgggaccc ccgggcagag ggtcaccatt    60
tcctgttctg gtagcaggtc caacgtccaa agaaattttg tttactggta ccagcagctc   120
ccaggaacgg ccccccaaact tctcatctat atgaacaata accgcccctc aggggtccct   180
gaccgattct ctggctctca ttctggcacc tcagcctccc tggccatcac tgggcttcgg   240
tccgaggatg aggctgatta ttattgtgct acttgggatg acaatctgag aggctgggtg   300
ttcggcggag ggaccaaggt gaccgtccta                                    330

<210> SEQ ID NO 55
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Val Gln Ser Gly Ala Glu Ile Lys Arg Pro Gly Ala
 1               5                  10                  15
```

```
Ser Val Lys Val Ser Cys Lys Ala Ser Gly Tyr Thr Phe Thr Arg Phe
             20                  25                  30
```

```
Gly Ile Asn Trp Val Arg Gln Ala Pro Gly Gln Gly Leu Glu Trp Met
         35                  40                  45
```

Gly Trp Met Asn Ser Asn Ser Gly Asn Ala Asp Ser Ala Gln Lys Phe
            50                  55                  60

Gln Gly Arg Leu Thr Met Thr Thr Asp Thr Ser Ser Thr Ala Tyr
 65                  70                  75                  80

Met Glu Leu Arg Asn Leu Arg Ser Glu Asp Thr Ala Val Tyr Tyr Cys
                 85                  90                  95

Ala Arg Met Asn Tyr Arg Gly Ser Lys Trp Glu Ile Asn Trp Phe Asp
            100                 105                 110

Pro Trp Gly Gln Gly Thr Leu Ile Thr Val Ser Ser
            115                 120

<210> SEQ ID NO 56
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Ser Val Val Thr Gln Pro Pro Ser Ala Ser Gly Thr Pro Gly Gln
 1               5                  10                  15

Arg Val Thr Ile Ser Cys Ser Gly Ser Arg Ser Asn Val Gln Arg Asn
             20                  25                  30

Phe Val Tyr Trp Tyr Gln Gln Leu Pro Gly Thr Ala Pro Lys Leu Leu
         35                  40                  45

Ile Tyr Met Asn Asn Asn Arg Pro Ser Gly Val Pro Asp Arg Phe Ser
     50                  55                  60

Gly Ser His Ser Gly Thr Ser Ala Ser Leu Ala Ile Thr Gly Leu Arg
 65                  70                  75                  80

Ser Glu Asp Glu Ala Asp Tyr Tyr Cys Ala Thr Trp Asp Asp Asn Leu
                 85                  90                  95

Arg Gly Trp Val Phe Gly Gly Gly Thr Lys Val Thr Val Leu
            100                 105                 110

<210> SEQ ID NO 57
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcacc tggtggagtc tgggggagac ctggtccagc ctggggaggtc cctgagactc      60 tcctgtgcag cgtctggatt taccctcaaa cgttatggca ttcactgggt ccgccaggcg     120
ccaggcaagg ggctggagtg ggtggcagtt acttggcatg atggaaatat atactatgca     180
gactccgtga agggccgact caccgtctcc agagacagtt acaagaacac ggtgatcta      240 caaatgaaca gcctgaaagt cgaggacacg gctctatatt actgtgcgag agatgccggg     300
caaaatgcgc ccattgacct ctggggccac ggaaccctgg tcaccgtctc ctca           354

<210> SEQ ID NO 58
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
caggctgtac tgactcagcc gtcttccctc tctgcatctc ctggagcatc agccagtctc    60
acctgcacct tacccagtgg catcaatgtt gctacccact ggatatactg gtaccagcag   120
aagcctggca gtcctcccca gtttctcctg cggtacaaat cagactcaga tatccaacac   180
ggctctggag tccccagccg cttctctgga tccaagatg cttcggccaa tgccgcgatt   240
ttagtcgtct ctggtctcca gtctgaggat gaggctgact attactgtat gatttggtat   300
tccaccgccg tggttttcgg cggagggacc aagctgaccg tcctg                    345
```

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gln Val His Leu Val Glu Ser Gly Gly Asp Leu Val Gln Pro Gly Arg
1               5                   10                  15

Ser Leu Arg Leu Ser Cys Ala Ala Ser Gly Phe Thr Leu Lys Arg Tyr
            20                  25                  30

Gly Ile His Trp Val Arg Gln Ala Pro Gly Lys Gly Leu Glu Trp Val
        35                  40                  45

Ala Val Thr Trp His Asp Gly Asn Ile Tyr Tyr Ala Asp Ser Val Lys
    50                  55                  60

Gly Arg Leu Thr Val Ser Arg Asp Ser Tyr Lys Asn Thr Val Asp Leu
65                  70                  75                  80

Gln Met Asn Ser Leu Lys Val Glu Asp Thr Ala Leu Tyr Tyr Cys Ala
                85                  90                  95

Arg Asp Ala Gly Gln Asn Ala Pro Ile Asp Leu Trp Gly His Gly Thr
            100                 105                 110

Leu Val Thr Val Ser Ser
        115
```

<210> SEQ ID NO 60
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Gln Ala Val Leu Thr Gln Pro Ser Ser Leu Ser Ala Ser Pro Gly Ala
1               5                   10                  15

Ser Ala Ser Leu Thr Cys Thr Leu Pro Ser Gly Ile Asn Val Ala Thr
            20                  25                  30

His Trp Ile Tyr Trp Tyr Gln Gln Lys Pro Gly Ser Pro Pro Gln Phe
        35                  40                  45

Leu Leu Arg Tyr Lys Ser Asp Ser Asp Ile Gln His Gly Ser Gly Val
    50                  55                  60

Pro Ser Arg Phe Ser Gly Ser Lys Asp Ala Ser Ala Asn Ala Ala Ile
65                  70                  75                  80

Leu Val Val Ser Gly Leu Gln Ser Glu Asp Glu Ala Asp Tyr Tyr Cys
                85                  90                  95
```

Met Ile Trp Tyr Ser Thr Ala Val Val Phe Gly Gly Gly Thr Lys Leu
            100                 105                 110

Thr Val Leu
        115

<210> SEQ ID NO 61
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caggtgcagt tggtggagtt tgggggaggc attttccagc ctgggggtc cctgagactc      60 tcctgtgtcg cgtctggatt ctccttcagg tattatggtt ccactgggt ccgccaggct    120 ccaggcaagg ggctggagtg gctggcagtt gtatggcatg atggaaggga gacacattat    180
ggagactccg tgaggggcg attcaccatc tccagagaca attacaagaa cacggtgttt     240
ttggaaatgg acagcctgag agtcgaggac acggctgtct atcactgtgc gagagatcgt   300
ggtagcgacg aacctattga ctactggggc cagggagttt tggtcaccgt ctcctca      357

<210> SEQ ID NO 62
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
caggctgtgc tgactcagcc gtcctccctc tctgcatctc ctggagcatc agccagtatc     60
acctgcacct tacgcagtga cctcactgtt agtccctgga tatactggta ccaacagaag   120
ccagggagtc ctccccgatt tctcctgaaa tacaaatcag actccaataa ctaccacggc   180
tctggagtcc ccagccgctt ctctggatcc aaagatgctt cggccaatgc agcgatttta   240
ctcatctctg gactccagtc tgaagatgag gctgactatt actgtcagac ttggcacacc   300
accactgtgg tatttggcgg agggaccaag ctgaccgtcc ta                       342

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Glu Phe Gly Gly Gly Ile Phe Gln Pro Gly Gly
1               5                   10                  15

Ser Leu Arg Leu Ser Cys Val Ala Ser Gly Phe Ser Phe Arg Tyr Tyr
            20                  25                  30

Gly Phe His Trp Val Arg Gln Ala Pro Gly Lys Gly Leu Glu Trp Leu
        35                  40                  45

Ala Val Val Trp His Asp Gly Arg Glu Thr His Tyr Gly Asp Ser Val
    50                  55                  60

Arg Gly Arg Phe Thr Ile Ser Arg Asp Asn Tyr Lys Asn Thr Val Phe
65                  70                  75                  80

Leu Glu Met Asp Ser Leu Arg Val Glu Asp Thr Ala Val Tyr His Cys
                85                  90                  95

Ala Arg Asp Arg Gly Ser Asp Glu Pro Ile Asp Tyr Trp Gly Gln Gly
            100                 105                 110

Val Leu Val Thr Val Ser Ser
        115

<210> SEQ ID NO 64
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Ala Val Leu Thr Gln Pro Ser Ser Leu Ser Ala Ser Pro Gly Ala
1               5                   10                  15

Ser Ala Ser Ile Thr Cys Thr Leu Arg Ser Asp Leu Thr Val Ser Pro
            20                  25                  30

Trp Ile Tyr Trp Tyr Gln Gln Lys Pro Gly Ser Pro Pro Arg Phe Leu
        35                  40                  45

Leu Lys Tyr Lys Ser Asp Ser Asn Asn Tyr His Gly Ser Gly Val Pro
    50                  55                  60

Ser Arg Phe Ser Gly Ser Lys Asp Ala Ser Ala Asn Ala Ala Ile Leu
65                  70                  75                  80

Leu Ile Ser Gly Leu Gln Ser Glu Asp Glu Ala Asp Tyr Tyr Cys Gln
                85                  90                  95

Thr Trp His Thr Thr Thr Val Val Phe Gly Gly Gly Thr Lys Leu Thr
            100                 105                 110

Val Leu

<210> SEQ ID NO 65
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caggtgcagt tggtggagtt tgggggaggc attttcgagc tggggggtc cctgagactc      60 tcctgtgtcg cgtctggatt ctccttcagg cattatggta tgcactgggt ccgccaggct    120
ccaggcaagg ggctggagtg gctggcagtt gtatggcatg atggaaggga gacacattat    180
ggagactccg tgaagggggcg attcaccatc tccagagaca attacaagaa tacgctgttt    240
ttgcaaatgg acagcctgag agtcgaggac acggctgtct atcactgtgc gagagatcgt    300
ggtagcgacg aacctattga ctactggggc cagggagttt tggtcaccgt ctcctca       357

<210> SEQ ID NO 66
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 66

```
caggctgtgc tgactcagcc gtcctccctc tctgcatctc ctggagcatc agccagtatc     60
acctgcacct tacgcagtga cgtcactgtt agtccctgga catactggta ccaacagaag    120
ccagggagtc ctcccccaatt tctcctgaga tacaaatcag actctgataa gtatcagggc   180
tctggagtcc ccagccgctt ctctggatcc aaaaatgctt cggccaatgc agcgattta    240
ctcatctctg gctccagtc tgaagatgag gctgactatt actgtcagac ttggcacacc    300
aacaatgtgg tatttggcgg agggaccaag ctgaccgtcc ta                       342
```

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Gln Val Gln Leu Val Glu Phe Gly Gly Gly Ile Phe Glu Pro Gly Gly
1               5                   10                  15

Ser Leu Arg Leu Ser Cys Val Ala Ser Gly Phe Ser Phe Arg His Tyr
            20                  25                  30

Gly Met His Trp Val Arg Gln Ala Pro Gly Lys Gly Leu Glu Trp Leu
        35                  40                  45

Ala Val Val Trp His Asp Gly Arg Glu Thr His Tyr Gly Asp Ser Val
    50                  55                  60

Lys Gly Arg Phe Thr Ile Ser Arg Asp Asn Tyr Lys Asn Thr Leu Phe
65                  70                  75                  80

Leu Gln Met Asp Ser Leu Arg Val Glu Asp Thr Ala Val Tyr His Cys
                85                  90                  95

Ala Arg Asp Arg Gly Ser Asp Glu Pro Ile Asp Tyr Trp Gly Gln Gly
            100                 105                 110

Val Leu Val Thr Val Ser Ser
        115
```

<210> SEQ ID NO 68
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Gln Ala Val Leu Thr Gln Pro Ser Ser Leu Ser Ala Ser Pro Gly Ala
1               5                   10                  15

Ser Ala Ser Ile Thr Cys Thr Leu Arg Ser Asp Val Thr Val Ser Pro
            20                  25                  30

Trp Thr Tyr Trp Tyr Gln Gln Lys Pro Gly Ser Pro Pro Gln Phe Leu
        35                  40                  45

Leu Arg Tyr Lys Ser Asp Ser Asp Lys Tyr Gln Gly Ser Gly Val Pro
    50                  55                  60

Ser Arg Phe Ser Gly Ser Lys Asn Ala Ser Ala Asn Ala Ala Ile Leu
65                  70                  75                  80

Leu Ile Ser Gly Leu Gln Ser Glu Asp Glu Ala Asp Tyr Tyr Cys Gln
                85                  90                  95
```

-continued

```
Thr Trp His Thr Asn Asn Val Val Phe Gly Gly Gly Thr Lys Leu Thr
                100                 105                 110

Val Leu
```

<210> SEQ ID NO 69
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
caggtgcagt tggtggagtt tgggggaggc attttccagc ctggggggtc cctgagactc      60
tcctgtgtcg cgtctggatt ctccttcaga tattatggtt tccactgggt ccgccaggct     120
ccaggcaagg ggctggagtg gctggcagtt gtatggcatg atggaaggga gacacattat     180
ggagactccg tgaaggggcg attcaccatc tccagagaca attacaagaa cacgctgttt     240
ttgcaaatgg acagcctgag agtcgaggac acggctgtct atcactgtgc gagagatcgt     300
ggtagcgacg aacctattga ctactggggc cagggagttt tggtcaccgt ctcctca        357
```

<210> SEQ ID NO 70
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
caggctgtgc tgactcagcc gtcctccctc tctgcatctc ctggagcatc agccagtatc      60
acctgcacct tacgcagtgg cctcactgtt agtccctgga tatactggta ccaacagaag     120
ccagggagtc ctccccaatt tctcctgaga tacaaatcag actccgaaaa ctaccggggc     180
tctggagtcc ccagtcgctt ctctggatcc aaagaggctt cggccaatgc agcgatttta     240
ttcatctctg gactccagtc tgaagatgag gctgactatt actgtcagac ttggcacacc     300
agcacagtgg tatttggcgg agggaccaag ctgaccgtcc ta                        342
```

<210> SEQ ID NO 71
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Gln Val Gln Leu Val Glu Phe Gly Gly Gly Ile Phe Gln Pro Gly Gly
1               5                   10                  15

Ser Leu Arg Leu Ser Cys Val Ala Ser Gly Phe Ser Phe Arg Tyr Tyr
            20                  25                  30

Gly Phe His Trp Val Arg Gln Ala Pro Gly Lys Gly Leu Glu Trp Leu
        35                  40                  45

Ala Val Val Trp His Asp Gly Arg Glu Thr His Tyr Gly Asp Ser Val
    50                  55                  60

Lys Gly Arg Phe Thr Ile Ser Arg Asp Asn Tyr Lys Asn Thr Leu Phe
65                  70                  75                  80

Leu Gln Met Asp Ser Leu Arg Val Glu Asp Thr Ala Val Tyr His Cys
                85                  90                  95
```

Ala Arg Asp Arg Gly Ser Asp Glu Pro Ile Asp Tyr Trp Gly Gln Gly
            100                 105                 110

Val Leu Val Thr Val Ser Ser
        115

<210> SEQ ID NO 72
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ala Val Leu Thr Gln Pro Ser Ser Leu Ser Ala Ser Pro Gly Ala
1               5                   10                  15

Ser Ala Ser Ile Thr Cys Thr Leu Arg Ser Gly Leu Thr Val Ser Pro
            20                  25                  30

Trp Ile Tyr Trp Tyr Gln Gln Lys Pro Gly Ser Pro Pro Gln Phe Leu
        35                  40                  45

Leu Arg Tyr Lys Ser Asp Ser Glu Asn Tyr Arg Gly Ser Gly Val Pro
    50                  55                  60

Ser Arg Phe Ser Gly Ser Lys Glu Ala Ser Ala Asn Ala Ala Ile Leu
65                  70                  75                  80

Phe Ile Ser Gly Leu Gln Ser Glu Asp Glu Ala Asp Tyr Tyr Cys Gln
                85                  90                  95

Thr Trp His Thr Ser Thr Val Val Phe Gly Gly Gly Thr Lys Leu Thr
            100                 105                 110

Val Leu

<210> SEQ ID NO 73
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
caggtgcagc tggtgcagtc tggggctgag attaagaggc ctggggcctc agtgaaggtc     60
tcctgcaagg cgtctggata cattttcacc aactttggca tcaactgggt gcgacaggcc    120
cctggtcaag gcttgagtg gatgggatgg atgaactcca gtatggtaa tgcggactct      180 gcacataagt tccaggacag actcactatg accaccgaca cctccacaag tacagcctac    240
atggagctga gaatctgag atctgaggac acggccgtat attattgcgc gagaatgaat     300
taccgtgatt cgaagtggga cgtgaattgg ttcgacccct ggggccaggg aaccctgatc    360
accgtctcct ca                                                        372

<210> SEQ ID NO 74
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
cagtctgtgg tgactcagcc accctcagcg tctgggaccc ccgggcagag ggtcaccatc    60
tcctgttctg gaagcaggtc aacgtcgaa agaaattttg tttactggta ccagcagctc   120
ccaggaacgg cccccaaact tctcatctat atgaacaatc agcgcccctc aggggtccct   180
gaccgattct ctggctctcg ttctggcacc tcagcctccc tggccatcac tgggcttcgg   240
tccgaggatg aggctgatta ttattgtgca gtttgggatg acaatctcag aggctgggtg   300
ttcggcggag ggaccgaggt gaccgtccta                                    330
```

<210> SEQ ID NO 75
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Gln Val Gln Leu Val Gln Ser Gly Ala Glu Ile Lys Arg Pro Gly Ala
1               5                   10                  15
Ser Val Lys Val Ser Cys Lys Ala Ser Gly Tyr Ile Phe Thr Asn Phe
            20                  25                  30
Gly Ile Asn Trp Val Arg Gln Ala Pro Gly Gln Gly Leu Glu Trp Met
        35                  40                  45
Gly Trp Met Asn Ser Lys Tyr Gly Asn Ala Asp Ser Ala His Lys Phe
    50                  55                  60
Gln Asp Arg Leu Thr Met Thr Thr Asp Thr Ser Thr Ser Thr Ala Tyr
65                  70                  75                  80
Met Glu Leu Arg Asn Leu Arg Ser Glu Asp Thr Ala Val Tyr Tyr Cys
                85                  90                  95
Ala Arg Met Asn Tyr Arg Asp Ser Lys Trp Asp Val Asn Trp Phe Asp
            100                 105                 110
Pro Trp Gly Gln Gly Thr Leu Ile Thr Val Ser Ser
        115                 120
```

<210> SEQ ID NO 76
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Gln Ser Val Val Thr Gln Pro Pro Ser Ala Ser Gly Thr Pro Gly Gln
1               5                   10                  15
Arg Val Thr Ile Ser Cys Ser Gly Ser Arg Ser Asn Val Glu Arg Asn
            20                  25                  30
Phe Val Tyr Trp Tyr Gln Gln Leu Pro Gly Thr Ala Pro Lys Leu Leu
        35                  40                  45
Ile Tyr Met Asn Asn Gln Arg Pro Ser Gly Val Pro Asp Arg Phe Ser
    50                  55                  60
Gly Ser Arg Ser Gly Thr Ser Ala Ser Leu Ala Ile Thr Gly Leu Arg
65                  70                  75                  80
Ser Glu Asp Glu Ala Asp Tyr Tyr Cys Ala Val Trp Asp Asp Asn Leu
                85                  90                  95
```

```
Arg Gly Trp Val Phe Gly Gly Gly Thr Glu Val Thr Val Leu
            100                 105                 110
```

<210> SEQ ID NO 77
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
caggtgcagc tggtgcagtc tggggctgag attaagaggc ctggggcctc agtgaaggtc    60
tcctgcaagg cgtctggata cactttcacc ggctttggta tcaactgggt gcgacaggcc   120
ccaggacagg gcttgagtg gatgggatgg atgaactcca acactggtga tgcggactct   180
gcacagaagt tccagggcag actcactatg accaccgaca cctccacaag tacagcccac   240
atggagctga cgaatctggg atctgaggac acggccgtat actattgcgc gagaatgaat   300
ttccttggtt cgaagtggga ggtgaactgg ttcgacccct ggggccaggg aaccctgatc   360
accgtctcct ca                                                       372
```

<210> SEQ ID NO 78
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
gatgttgtgc tgactcagtc tccactctcc ctgtccgtca cccttggaca gccggcctcc    60
atctcctgca ggtccagtca gagcctccca agagatgatg aatactccta cctgaattgg   120
tttcagcaga ggccaggcca gtctccaagg cgcctaattt atagggtttc taagcgggac   180
tctggggtcc cagacagatt cagcggcagt gggtcagaca cttatttcac actgacaatc   240
agcagggtgg aggctgagga tgttggagtt tattactgca tgcaaggtac atactggccc   300
gggacgttcg gccaagggac gaagttggaa atcgagcga                          339
```

<210> SEQ ID NO 79
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Gln Val Gln Leu Val Gln Ser Gly Ala Glu Ile Lys Arg Pro Gly Ala
1               5                   10                  15

Ser Val Lys Val Ser Cys Lys Ala Ser Gly Tyr Thr Phe Thr Gly Phe
            20                  25                  30

Gly Ile Asn Trp Val Arg Gln Ala Pro Gly Gln Gly Leu Glu Trp Met
        35                  40                  45

Gly Trp Met Asn Ser Asn Thr Gly Asp Ala Asp Ser Ala Gln Lys Phe
    50                  55                  60

Gln Gly Arg Leu Thr Met Thr Thr Asp Thr Ser Thr Ser Thr Ala His
65                  70                  75                  80

Met Glu Leu Thr Asn Leu Gly Ser Glu Asp Thr Ala Val Tyr Tyr Cys
                85                  90                  95
```

Ala Arg Met Asn Phe Leu Gly Ser Lys Trp Glu Val Asn Trp Phe Asp
            100                 105                 110

Pro Trp Gly Gln Gly Thr Leu Ile Thr Val Ser Ser
        115                 120

<210> SEQ ID NO 80
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Val Val Leu Thr Gln Ser Pro Leu Ser Leu Ser Val Thr Leu Gly
1               5                   10                  15

Gln Pro Ala Ser Ile Ser Cys Arg Ser Ser His Ser Leu Pro Arg Asp
            20                  25                  30

Asp Glu Tyr Ser Tyr Leu Asn Trp Phe Gln Gln Arg Pro Gly Gln Ser
        35                  40                  45

Pro Arg Arg Leu Ile Tyr Arg Val Ser Lys Arg Asp Ser Gly Val Pro
    50                  55                  60

Asp Arg Phe Ser Gly Ser Gly Ser Asp Thr Tyr Phe Thr Leu Thr Ile
65                  70                  75                  80

Ser Arg Val Glu Ala Glu Asp Val Gly Val Tyr Tyr Cys Met Gln Gly
                85                  90                  95

Thr Tyr Trp Pro Gly Thr Phe Gly Gln Gly Thr Lys Leu Glu Ile Glu
            100                 105                 110

Arg

<210> SEQ ID NO 81
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtacagc tggtggagtc tgggggaggc ctggtccagc ctgggggtc tctgagactc        60 tcctgtgcag cctctggatt cacctttaat acgattgga tgacttgggt ccgccaggct       120
ccagggaagg gtctggagtg gtggccaac ataatacaag atggaagcga aacatactat       180
gtggactctg tgaagggccg attcaccatc tccagagaca atgccaagaa tttactgtat      240
ctgcagatga acagcctgag agtcgaggac acggctgtgt atttctgtgg ccggagtatg      300
gacgtctggg gccaagggac cacggtcatc gtctcctca                            339

<210> SEQ ID NO 82
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
cagtctgtgc tgactcagcc accctcagcg tctgggaccc ccgggcagag ggtcaccatc       60
tcttgttctg gaagcagctc caacatcgga agtaatactg tgaactggta ccaccaggtc     120

```
ccaggaacgg ccccaaaact cctcatctat actgataatc agcggccctc aggggtccct    180
gaccgattct ctggctccaa gtctggcacc tcagcctccc tggccatcag tgggctccag    240
tctgaggatg aaggtgatta ttactgtgca gcgagggatg gcagcctgga tgtttgggtg    300
ttcggcggag ggaccaaagt gactgtccta                                     330
```

<210> SEQ ID NO 83
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn His Asp
            20                  25                  30

Trp Met Thr Trp Val Arg Gln Ala Pro Gly Lys Gly Leu Glu Trp Val
        35                  40                  45

Ala Asn Ile Ile Gln Asp Gly Ser Glu Thr Tyr Tyr Val Asp Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Val Glu Asp Thr Ala Val Tyr Phe Cys
                85                  90                  95

Gly Arg Ser Met Asp Val Trp Gly Gln Gly Thr Thr Val Ile Val Ser
            100                 105                 110

Ser
```

<210> SEQ ID NO 84
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr His Gln Val Pro Gly Thr Ala Pro Lys Leu Leu
        35                  40                  45

Ile Tyr Thr Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Gly Asp Tyr Tyr Cys Ala Ala Arg Asp Gly Ser Leu
                85                  90                  95

Asp Val Trp Val Phe Gly Gly Gly Thr Lys Val Thr Val Leu
            100                 105                 110
```

<210> SEQ ID NO 85
<211> LENGTH: 372
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 85
caggtgcagc tggtgcagtc tggggctgag attaagaggc ctggggcctc agtgaaggtc      60
tcctgcaagg cgtctggata cactttcacc aactttggaa tcaactgggt gcgacaggcc     120
cctggacaag gcttgagtg gatgggatgg atgaactcca gaactggtga tgcggactct      180
gcacagaact tccagggcag gctcactatg accaccgaca cctccagaag tatagcctac     240
atggagctga cgcacctgac ctctgaggac acggccgtat attattgcgc gagaatgaat     300
ttccttggtt cgaggtggga ggtgaactgg ttcgacccct ggggccaggg aaccctgatc     360
accgtctcct ca                                                        372

<210> SEQ ID NO 86
<211> LENGTH: 330
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 86
cagtctgtgg tgactcagcc accctcagtg tctgggaccc ccgggcagag ggtcaccatc      60
tcctgttctg gaagcaggtc caacgtcgaa agaaattttt tttactggta tcagcaattc     120
ccaggaacgg ccccccaaact tctcatctat atgaacagtc agcggcccgc agggtccct    180 gaccgattct ctggctctcg ttctggcacc tcagtttccc tggccatcac tgggcttcgg    240
tccgaggatg aggctgacta ttattgtgca acttgggatg acaatctgag aggctgggtg    300
ttcggcggag ggaccaaggt gaccgtccta                                     330

<210> SEQ ID NO 87
<211> LENGTH: 124
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 87

Gln Val Gln Leu Val Gln Ser Gly Ala Glu Ile Lys Arg Pro Gly Ala
1               5                   10                  15

Ser Val Lys Val Ser Cys Lys Ala Ser Gly Tyr Thr Phe Thr Asn Phe
            20                  25                  30

Gly Ile Asn Trp Val Arg Gln Ala Pro Gly Gln Gly Leu Glu Trp Met
        35                  40                  45

Gly Trp Met Asn Ser Arg Thr Gly Asp Ala Asp Ser Ala Gln Asn Phe
    50                  55                  60

Gln Gly Arg Leu Thr Met Thr Thr Asp Thr Ser Arg Ser Ile Ala Tyr
65                  70                  75                  80

Met Glu Leu Thr His Leu Thr Ser Glu Asp Thr Ala Val Tyr Tyr Cys
                85                  90                  95

Ala Arg Met Asn Phe Leu Gly Ser Arg Trp Glu Val Asn Trp Phe Asp
            100                 105                 110

Pro Trp Gly Gln Gly Thr Leu Ile Thr Val Ser Ser
        115                 120

<210> SEQ ID NO 88
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Gln Ser Val Val Thr Gln Pro Pro Ser Val Ser Gly Thr Pro Gly Gln
1               5                   10                  15

Arg Val Thr Ile Ser Cys Ser Gly Ser Arg Ser Asn Val Glu Arg Asn
            20                  25                  30

Phe Phe Tyr Trp Tyr Gln Gln Phe Pro Gly Thr Ala Pro Lys Leu Leu
        35                  40                  45

Ile Tyr Met Asn Ser Gln Arg Pro Ala Gly Val Pro Asp Arg Phe Ser
    50                  55                  60

Gly Ser Arg Ser Gly Thr Ser Val Ser Leu Ala Ile Thr Gly Leu Arg
65                  70                  75                  80

Ser Glu Asp Glu Ala Asp Tyr Tyr Cys Ala Thr Trp Asp Asp Asn Leu
                85                  90                  95

Arg Gly Trp Val Phe Gly Gly Gly Thr Lys Val Thr Val Leu
            100                 105                 110
```

<210> SEQ ID NO 89
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

| | |
|---|---|
| caggtgcagc tggtgcagtc tggggctgag attaagcggc ctggggcctc agtgaagatc | 60 |
| tcctgcaagg cgtctggata cattttcacc agctttggta tcaactgggt gcgacaggcc | 120 |
| cctggacaag ggcttgagtg gatgggatgg atgaactcca acactggtga tgcggactct | 180 |
| ctacagaagt tccagggcag actcaccatg accaccgaca cctccacaag cacagcctac | 240 |
| atggaattga gcaatctgag atctgaagac acggccgtat attattgcgc gagaatgaat | 300 |
| ttccatggtt cgaggtggga cgtgaactgg ttcgacccct ggggccaggg aaccctgatc | 360 |
| accgtctcct ca | 372 |

<210> SEQ ID NO 90
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

| | |
|---|---|
| cagtctgtgg tgactcagcc accctcagcg tctgggaccc ccgggcagag ggtcatcatc | 60 |
| tcctgttctg gaagcgggtc caacgtcgaa agaaattctg tttactggta ccaacagttc | 120 |
| ccgggaacgg ccccccaaact tctcatctac atgagcaata gcgcccctc aggggtccct | 180 |
| gaccgattct ttggctctcg ttctggcacc tcagcctccc tggccatcac tgggcttcgg | 240 |
| cccgaggatg aggctgatta ttattgtgca gtttgggatg acagtctgag aggctgggta | 300 |
| ttcggcggag ggaccaaggt gaccgtccta | 330 |

<210> SEQ ID NO 91
<211> LENGTH: 124
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 91

Gln Val Gln Leu Val Gln Ser Gly Ala Glu Ile Lys Arg Pro Gly Ala
1               5                   10                  15

Ser Val Lys Ile Ser Cys Lys Ala Ser Gly Tyr Ile Phe Thr Ser Phe
            20                  25                  30

Gly Ile Asn Trp Val Arg Gln Ala Pro Gly Gln Gly Leu Glu Trp Met
        35                  40                  45

Gly Trp Met Asn Ser Asn Thr Gly Asp Ala Asp Ser Leu Gln Lys Phe
    50                  55                  60

Gln Gly Arg Leu Thr Met Thr Thr Asp Thr Ser Thr Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Met Asn Phe His Gly Ser Arg Trp Asp Val Asn Trp Phe Asp
            100                 105                 110

Pro Trp Gly Gln Gly Thr Leu Ile Thr Val Ser Ser
        115                 120

<210> SEQ ID NO 92
<211> LENGTH: 110
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 92

Gln Ser Val Val Thr Gln Pro Pro Ser Ala Ser Gly Thr Pro Gly Gln
1               5                   10                  15

Arg Val Ile Ile Ser Cys Ser Gly Ser Gly Ser Asn Val Glu Arg Asn
            20                  25                  30

Ser Val Tyr Trp Tyr Gln Gln Phe Pro Gly Thr Ala Pro Lys Leu Leu
        35                  40                  45

Ile Tyr Met Ser Asn Arg Arg Pro Ser Gly Val Pro Asp Arg Phe Phe
    50                  55                  60

Gly Ser Arg Ser Gly Thr Ser Ala Ser Leu Ala Ile Thr Gly Leu Arg
65                  70                  75                  80

Pro Glu Asp Glu Ala Asp Tyr Tyr Cys Ala Val Trp Asp Asp Ser Leu
                85                  90                  95

Arg Gly Trp Val Phe Gly Gly Gly Thr Lys Val Thr Val Leu
            100                 105                 110

<210> SEQ ID NO 93
<211> LENGTH: 354
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 93

```
caggtgcagc tggcggagtc tgggggaggc gtggtccagc ctgggggtc cctgagactt        60 tcctgtgcag cgtctggatt cagtctcaag agttatggca ttcactgggt ccgccaggcc      120
ccaggcaagg ggctggagtg ggtggcagtt atctggcccc gacgagatac acagtatgca      180
gactccgtga agggccgagt caccatgtac agagacgact ataggaatac ggtctatcta      240
cagatgaaca gcctgagatt cgatgacgcg gctctgtatc ggtgtgcgag agatcgcggt      300
gaagacaatc ccatagattt ctggggccag ggaaccctgg tcaccgtctc ctca            354
```

<210> SEQ ID NO 94
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
caggctgtgc tgactcagcc gtcttccctc tctgcatctc ctggagcatc agccagtctc       60
acctgcacct tgctcagcgg catcaatgtt ggtccctact ggatatactg gtatcagcag      120
aaggcaggga gtcctcccca gtttctcctc aggtacaggt cagactcaga tgaggagcag      180
ggctctgagg tccccagccg cttctctgga tccaaagatg cctcggccaa tgcagggatt      240
ttggtcatct ctgggctcca gtctgaagat gaagctgact attactgtat gatctggcac      300
aggaccggtg tgattttcgg cggagggacc aagctgaccg tccta                      345
```

<210> SEQ ID NO 95
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Gln Val Gln Leu Ala Glu Ser Gly Gly Gly Val Val Gln Pro Gly Gly
1               5                   10                  15

Ser Leu Arg Leu Ser Cys Ala Ala Ser Gly Phe Ser Leu Lys Ser Tyr
            20                  25                  30

Gly Ile His Trp Val Arg Gln Ala Pro Gly Lys Gly Leu Glu Trp Val
        35                  40                  45

Ala Val Ile Trp Pro Arg Arg Asp Thr Gln Tyr Ala Asp Ser Val Lys
    50                  55                  60

Gly Arg Val Thr Met Tyr Arg Asp Asp Tyr Arg Asn Thr Val Tyr Leu
65                  70                  75                  80

Gln Met Asn Ser Leu Arg Phe Asp Asp Ala Ala Leu Tyr Arg Cys Ala
                85                  90                  95

Arg Asp Arg Gly Glu Asp Asn Pro Ile Asp Phe Trp Gly Gln Gly Thr
            100                 105                 110

Leu Val Thr Val Ser Ser
        115
```

<210> SEQ ID NO 96
<211> LENGTH: 115
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 96

Gln Ala Val Leu Thr Gln Pro Ser Ser Leu Ser Ala Ser Pro Gly Ala
1               5                   10                  15

Ser Ala Ser Leu Thr Cys Thr Leu Leu Ser Gly Ile Asn Val Gly Pro
                20                  25                  30

Tyr Trp Ile Tyr Trp Tyr Gln Gln Lys Ala Gly Ser Pro Pro Gln Phe
            35                  40                  45

Leu Leu Arg Tyr Arg Ser Asp Ser Asp Glu Glu Gln Gly Ser Glu Val
        50                  55                  60

Pro Ser Arg Phe Ser Gly Ser Lys Asp Ala Ser Ala Asn Ala Gly Ile
65                  70                  75                  80

Leu Val Ile Ser Gly Leu Gln Ser Glu Asp Glu Ala Asp Tyr Tyr Cys
                85                  90                  95

Met Ile Trp His Arg Thr Gly Val Ile Phe Gly Gly Gly Thr Lys Leu
            100                 105                 110

Thr Val Leu
        115

<210> SEQ ID NO 97
<211> LENGTH: 372
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 97
caggtgcagc tggtgcagtc tggggctgag attaagaggc ctggggcctc agtgaaggtc      60
tcctgcaagg cgtctggata cattttcacc agctttggta tcaactgggt gcgacaggcc     120
cctggacaag gcttgagtg gatgggatgg atgaactcca acactggtga tgcggactct     180
gtacagaagt tccagggcag actcaccatg accaccgacc cctccacaag tacagcctat     240
atggaactga ggaatctgag atctgacgac acggccgtat attattgcgc gagaatgaac     300
ttctttggtt cgcagtggga agtgaactgg ttcgacccct ggggccaggg aaccctgatc     360
accgtctcct ca                                                         372

<210> SEQ ID NO 98
<211> LENGTH: 330
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 98
cagtctgtgg tgactcagcc accctcagcg tctgggaccc ccgggcagag gatcaccatc      60
tcctgttctg gaagcaggtc caacgtcgaa agaaattctg tttactggta ccagcagctc     120
cgaggaacgg cccccaaact tctcatctat atgagcaatc agcgcccctc agggtcccct     180
gaccgattct ctggctctcg ttctggcacc tcagcctccc tggccatcac tgggcttcgg     240
tccgaggatg aggctgatta ttattgtgca gtttgggatg acaatctcag aggctgggtg     300
ttcggcggag ggaccgaggt gaccgtccta                                      330

<210> SEQ ID NO 99

<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Val Gln Ser Gly Ala Glu Ile Lys Arg Pro Gly Ala
1               5                   10                  15

Ser Val Lys Val Ser Cys Lys Ala Ser Gly Tyr Ile Phe Thr Ser Phe
            20                  25                  30

Gly Ile Asn Trp Val Arg Gln Ala Pro Gly Gln Gly Leu Glu Trp Met
        35                  40                  45

Gly Trp Met Asn Ser Asn Thr Gly Asp Ala Asp Ser Val Gln Lys Phe
    50                  55                  60

Gln Gly Arg Leu Thr Met Thr Thr Asp Pro Ser Thr Ser Thr Ala Tyr
65                  70                  75                  80

Met Glu Leu Arg Asn Leu Arg Ser Asp Asp Thr Ala Val Tyr Tyr Cys
                85                  90                  95

Ala Arg Met Asn Phe Phe Gly Ser Gln Trp Glu Val Asn Trp Phe Asp
            100                 105                 110

Pro Trp Gly Gln Gly Thr Leu Ile Thr Val Ser Ser
        115                 120

<210> SEQ ID NO 100
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ser Val Val Thr Gln Pro Pro Ser Ala Ser Gly Thr Pro Gly Gln
1               5                   10                  15

Arg Ile Thr Ile Ser Cys Ser Gly Ser Arg Ser Asn Val Glu Arg Asn
            20                  25                  30

Ser Val Tyr Trp Tyr Gln Gln Leu Arg Gly Thr Ala Pro Lys Leu Leu
        35                  40                  45

Ile Tyr Met Ser Asn Gln Arg Pro Ser Gly Val Pro Asp Arg Phe Ser
    50                  55                  60

Gly Ser Arg Ser Gly Thr Ser Ala Ser Leu Ala Ile Thr Gly Leu Arg
65                  70                  75                  80

Ser Glu Asp Glu Ala Asp Tyr Tyr Cys Ala Val Trp Asp Asp Asn Leu
                85                  90                  95

Arg Gly Trp Val Phe Gly Gly Gly Thr Glu Val Thr Val Leu
            100                 105                 110

<210> SEQ ID NO 101
<211> LENGTH: 373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
ccaggtgcac ctggtgcagt ctggggctga gattaagagg cctggggcct cagtgaaggt      60
ctcctgcaag gcgtctggat acactttcac cagctttggt atcaactggg tgcgacaggc     120

```
cc ctggacaa gggcttgagt ggatgggatg gatgaactcc aacagtggtg atgcggactc    180
tgcacagaag ttccagggca gactcactat gaccaccgac acctccacaa gtacagccta    240
catggagctg aggaatctga gatctgagga cacggccgta tattattgcg cgagaatgaa    300
tttccgtggt tcgaagtggg aggtgaactg gttcgacccc tggggccagg gaaccctgat    360
caccgtctcc tca                                                       373
```

<210> SEQ ID NO 102
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
cagtctgtgg tgactcagcc accctcagcg tctgggaccc ccgggcagag ggtcaccatc     60
tcctgttctg gaagcaggtc caacgtcgaa agaaattttg tttactggta ccagcaactc    120
ccaggaacgg ccccccaaact tctcatctat atgaacagtc agcggccctc agggctccct    180
gaccgattct ctggctctcg ttctggcacc tcagcctccc tggccatcac tgggcttcgg    240
tccgaggatg aggctgacta ttattgtgca acttgggatg acaatctgag aggctgggtg    300
ttcggcggag ggaccaaggt gaccgtccta                                     330
```

<210> SEQ ID NO 103
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

```
Gln Val His Leu Val Gln Ser Gly Ala Glu Ile Lys Arg Pro Gly Ala
1               5                   10                  15

Ser Val Lys Val Ser Cys Lys Ala Ser Gly Tyr Thr Phe Thr Ser Phe
            20                  25                  30

Gly Ile Asn Trp Val Arg Gln Ala Pro Gly Gln Gly Leu Glu Trp Met
        35                  40                  45

Gly Trp Met Asn Ser Asn Ser Gly Asp Ala Asp Ser Ala Gln Lys Phe
    50                  55                  60

Gln Gly Arg Leu Thr Met Thr Thr Asp Thr Ser Thr Ser Thr Ala Tyr
65                  70                  75                  80

Met Glu Leu Arg Asn Leu Arg Ser Glu Asp Thr Ala Val Tyr Tyr Cys
                85                  90                  95

Ala Arg Met Asn Phe Arg Gly Ser Lys Trp Glu Val Asn Trp Phe Asp
            100                 105                 110

Pro Trp Gly Gln Gly Thr Leu Ile Thr Val Ser Ser
        115                 120
```

<210> SEQ ID NO 104
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Ser Val Val Thr Gln Pro Pro Ser Ala Ser Gly Thr Pro Gly Gln
1               5                   10                  15

Arg Val Thr Ile Ser Cys Ser Gly Ser Arg Ser Asn Val Glu Arg Asn
            20                  25                  30

Phe Val Tyr Trp Tyr Gln Gln Leu Pro Gly Thr Ala Pro Lys Leu Leu
        35                  40                  45

Ile Tyr Met Asn Ser Gln Arg Pro Ser Gly Val Pro Asp Arg Phe Ser
    50                  55                  60

Gly Ser Arg Ser Gly Thr Ser Ala Ser Leu Ala Ile Thr Gly Leu Arg
65                  70                  75                  80

Ser Glu Asp Glu Ala Asp Tyr Tyr Cys Ala Thr Trp Asp Asp Asn Leu
                85                  90                  95

Arg Gly Trp Val Phe Gly Gly Gly Thr Lys Val Thr Val Leu
            100                 105                 110

<210> SEQ ID NO 105
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
caggtgcagc tggtgcagtc tggggctgag attaagaggc ctggggcctc agtgaaggtc      60
tcctgcaagg cgtctggata caccttcacc agatttggta tcaactgggt gcgacaggcc     120
cctggacaag gcttgagtg gatgggatgg atgaactcca acactggtga tgcggactct     180
gcacagaagt tccagggcag actcagtatg accaccgaca cctccacaag tacagcctac     240
atggagctga gagtctgac atctgacgac acggccgtat attttgcgc gagaatgaat     300 tactggggt cgaagtggga cgtgaactgg ttcgacccct ggggccaggg aaccctgatc     360
accgtctcct ca                                                         372

<210> SEQ ID NO 106
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
cagtctgtgg tgactcagcc accctcagcg tctgggaccc ccgggcagag ggtcaccatc      60
tcctgttctg gaagaaggac caacgtggaa agaaattctg tctactggta ccagcagctc     120
ccaggaacgg cccccaaact tctcatctat atgagcaata gcgcccctc aggggtccct     180 gaccgattct ccggctctcg ttctggcacc tctgcctccc tggccatcac tgggcttcgg     240
tccgaggatg aggctgatta ttattgtgca gtttgggatg acaatctgag aggctgggtg     300
ttcggcggag ggaccaaggt gaccgtccta                                      330

<210> SEQ ID NO 107
<211> LENGTH: 124
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 107

Gln Val Gln Leu Val Gln Ser Gly Ala Glu Ile Lys Arg Pro Gly Ala
1               5                   10                  15

Ser Val Lys Val Ser Cys Lys Ala Ser Gly Tyr Thr Phe Thr Arg Phe
            20                  25                  30

Gly Ile Asn Trp Val Arg Gln Ala Pro Gly Gln Gly Leu Glu Trp Met
        35                  40                  45

Gly Trp Met Asn Ser Asn Thr Gly Asp Ala Asp Ser Ala Gln Lys Phe
    50                  55                  60

Gln Gly Arg Leu Ser Met Thr Thr Asp Thr Ser Thr Ser Thr Ala Tyr
65                  70                  75                  80

Met Glu Leu Lys Ser Leu Thr Ser Asp Asp Thr Ala Val Tyr Phe Cys
                85                  90                  95

Ala Arg Met Asn Tyr Trp Gly Ser Lys Trp Asp Val Asn Trp Phe Asp
            100                 105                 110

Pro Trp Gly Gln Gly Thr Leu Ile Thr Val Ser Ser
        115                 120

<210> SEQ ID NO 108
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Ser Val Val Thr Gln Pro Pro Ser Ala Ser Gly Thr Pro Gly Gln
1               5                   10                  15

Arg Val Thr Ile Ser Cys Ser Gly Arg Arg Thr Asn Val Glu Arg Asn
            20                  25                  30

Ser Val Tyr Trp Tyr Gln Gln Leu Pro Gly Thr Ala Pro Lys Leu Leu
        35                  40                  45

Ile Tyr Met Ser Asn Lys Arg Pro Ser Gly Val Pro Asp Arg Phe Ser
    50                  55                  60

Gly Ser Arg Ser Gly Thr Ser Ala Ser Leu Ala Ile Thr Gly Leu Arg
65                  70                  75                  80

Ser Glu Asp Glu Ala Asp Tyr Tyr Cys Ala Val Trp Asp Asp Asn Leu
                85                  90                  95

Arg Gly Trp Val Phe Gly Gly Gly Thr Lys Val Thr Val Leu
            100                 105                 110

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Phe Ser Phe Arg His Tyr Gly Met His
1               5                   10

<210> SEQ ID NO 110
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 110

Val Val Trp His Asp Gly Arg Glu Thr His Tyr Gly Asp Ser Val
1               5                   10                  15

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Arg Gly Ser Asp Glu Pro Ile Asp Tyr
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Leu Arg Ser Asp Val Thr Val Ser Pro Trp Thr Tyr
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Ser Asp Ser Asp Lys Tyr Gln Gly Ser
1               5                   10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Thr Trp His Thr Thr Thr Val
1               5

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Ser Phe Arg His Tyr Gly Met His
1               5                   10
```

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Val Val Trp His Asp Gly Arg Glu Thr His Tyr Gly Asp Ser Val
1               5                   10                  15

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Arg Gly Ser Asp Glu Pro Ile Asp Tyr
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Leu Arg Ser Asp Val Thr Val Ser Pro Trp Thr Tyr
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Lys Ser Asp Ser Asp Lys Tyr Gln Gly Ser
1               5                   10

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Thr Trp His Thr Ser Thr Val
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 121

Gly Phe Ser Phe Arg Tyr Tyr Gly Phe His
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Val Trp His Asp Gly Arg Glu Thr His Tyr Gly Asp Ser Val
1               5                   10                  15

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Arg Gly Ser Asp Glu Pro Ile Asp Tyr
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Leu Arg Ser Gly Leu Thr Val Ser Pro Trp Ile Tyr
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Ser Asp Ser Glu Asn Tyr Arg Gly Ser
1               5                   10

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Thr Trp His Thr Ser Thr Val
1               5

<210> SEQ ID NO 127
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Phe Ser Phe Arg Tyr Tyr Gly Phe His
1               5                   10

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Val Val Trp His Asp Gly Arg Glu Thr His Tyr Gly Asp Ser Val
1               5                   10                  15

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Arg Gly Ser Asp Glu Pro Ile Asp Tyr
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Thr Leu Arg Ser Asp Leu Thr Val Ser Pro Trp Ile Tyr
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Ser Asp Ser Asn Asn Tyr His Gly Ser
1               5                   10

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 132

Gln Thr Trp His Thr Thr Thr Val
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Phe Pro Phe Arg Tyr Tyr Gly Phe His
1               5                   10

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Val Trp His Asn Gly Arg Glu Thr Tyr Tyr Glu Asp Ser Val
1               5                   10                  15

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Arg Gly Ser Asp Glu Pro Ile Asp Tyr
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Leu Arg Ser Asp Leu Thr Val Gly Pro Tyr Trp Met Tyr
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Ser Asp Ser Glu Lys Tyr Gln Gly Ser
1               5                   10

<210> SEQ ID NO 138
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Thr Trp His Ala Asn Thr Val
1               5

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Phe Ser Phe Arg Arg Phe Gly Met His
1               5                   10

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Val Val Trp His Asp Gly Arg Glu Thr His Tyr Gly Asp Ser Val
1               5                   10                  15

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp Pro Gly Gln Asp Glu Ala Ile Asp Tyr
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Thr Leu His Ser Gly Leu Thr Val Gly Pro Tyr Trp Ile Tyr
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 143

Lys Ser Asp Ser Glu Glu Tyr Arg Ala Ser
1               5                   10

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Thr Trp His Thr Asn Lys Val
1               5

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Phe Ser Leu Arg Ser Phe Gly Met His
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Val Ile Trp Pro Arg Arg Ser Gln Ile Gln Tyr Ala Asp Ser Val
1               5                   10                  15

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Pro Gly Glu Asp Asn Pro Ile Asp Tyr
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Phe Leu Ser Gly Ile Asn Val Gly Pro Tyr Trp Ile Tyr
1               5                   10

<210> SEQ ID NO 149
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Ser Asp Ser Asp Lys His Gln Gly Ser
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Met Ile Trp His Val Ser Gly Val
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Phe Ser Leu Lys Ser Tyr Gly Ile His
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Val Ile Trp Pro Arg Arg Asp Thr Gln Tyr Ala Asp Ser Val
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Arg Gly Glu Asp Asn Pro Ile Asp Phe
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 154

Thr Leu Leu Ser Gly Ile Asn Val Gly Pro Tyr Trp Ile Tyr
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ser Asp Ser Asp Glu Glu Gln Gly Ser
1               5                   10

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Met Ile Trp His Arg Thr Gly Val
1               5

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Phe Ser Phe Arg His Tyr Gly Met His
1               5                   10

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Ile Trp His Asn Gly Arg Asp Arg Glu Tyr Ala Asp Ser Val
1               5                   10                  15

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Arg Gly Glu Asp Glu Pro Ile Asp Phe
1               5                   10

<210> SEQ ID NO 160
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Thr Leu Arg Ser Gly Leu Ser Ala Gly Pro Lys Trp Ile Tyr
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Lys Ser Asp Ser Glu Glu Arg Arg Ser Ser
1               5                   10

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Ile Trp His Ser Asn Val Val
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Phe Ser Phe Arg His Tyr Gly Met His
1               5                   10

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Val Ile Trp His Asn Gly Arg Asp Lys Asp Tyr Ala Asp Ser Val
1               5                   10                  15

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 165

Asp Arg Gly Glu Asp Glu Pro Ile Asp Phe
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Leu Arg Ser Gly Leu Asn Val Gly Pro Tyr Trp Ile Tyr
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Ser Asp Ser Glu Lys Arg Arg Ser Ser
1               5                   10

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Ile Trp His Ser Asn Ala Val
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Phe Thr Leu Lys Arg Tyr Gly Ile His
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Val Thr Trp His Asp Gly Asn Ile Tyr Tyr Ala Asp Ser Val
1               5                   10

<210> SEQ ID NO 171
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Ala Gly Gln Asn Ala Pro Ile Asp Leu
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr Leu Pro Ser Gly Ile Asn Val Ala Thr His Trp Ile Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Lys Ser Asp Ser Asp Ile Gln His Gly Ser
1               5                   10

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Met Ile Trp Tyr Ser Thr Ala Val
1               5

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Phe Thr Phe Pro Asn Ala Trp Phe Asn
1               5                   10

<210> SEQ ID NO 176
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 176

Arg Ile Lys Ser His Ser Asp Gly Gly Thr Ala Asp Tyr Ala Ala Pro
1               5                   10                  15

Val

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Glu Ile Tyr His Pro Val Asp Val
1               5

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Ser Ser His Ser Leu Pro Arg Asp Asp Glu Tyr Ser Tyr Leu Asn
1               5                   10                  15

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Val Ser Lys Arg Asp Ser
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Met Gln Gly Thr Tyr Trp Pro Gly Thr
1               5

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Phe Thr Phe Ile Thr Ala Trp Met Thr
1               5                   10

```
<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Leu Ile Lys Ser Gly Asn Asp Gly Gly Ala Ile Glu Tyr Ala Ala Pro
1               5                   10                  15

Val

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asn Asp Val Ala Leu Val Trp Gly Val Thr Pro Pro Leu Leu Leu
1               5                   10                  15

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Leu Ser Ser Gly His Gly Asn Tyr Pro Val Ala
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn Ala Asp Gly Ser His Ile Lys Gly Ala
1               5                   10

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gln Thr Trp Ala Pro Gly Trp
1               5

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 187

Gly Phe Val Phe Thr Thr Ala Trp Met Asn
1               5                   10

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ile Lys Ser Lys Asn Glu Ala Glu Thr Thr Asp Tyr Ala Ala Pro
1               5                   10                  15

Val

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Leu Glu Thr Tyr Tyr Glu Ser Asp Phe
1               5

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Arg Ser Ser Gln Ser Leu Ala Glu Arg Glu Glu Asp Ile Leu Leu Asn
1               5                   10                  15

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Val Ser Lys Arg Glu Ser
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Met Gln Arg Thr His Trp Pro Gln Thr
1               5

```
<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Phe Thr Phe Asn His Asp Trp Met Thr
1               5                   10

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asn Ile Ile Gln Asp Gly Ser Glu Thr Tyr Tyr Val Asp Ser Val
1               5                   10                  15

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Arg Val Ser Met Asp Val
1               5

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ser Gly Ser Ser Ser Asn Ile Gly Ser Asn Thr Val Asn
1               5                   10

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Thr Asp Asn Gln Arg Pro Ser
1               5

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 198

Ala Ala Arg Asp Gly Ser Leu Asp Val Trp
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Tyr Thr Phe Thr Ser Phe Gly Ile Asn
1               5                   10

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Trp Met Asn Ser Asn Ser Gly Asp Ala Asp Ser Ala Gln Lys Phe
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Met Asn Phe Arg Gly Ser Lys Trp Glu Val Asn Trp Phe Asp Pro
1               5                   10                  15

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Gly Ser Arg Ser Asn Val Glu Arg Asn Phe Val Tyr
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Met Asn Ser Gln Arg Pro Ser
1               5

<210> SEQ ID NO 204
<211> LENGTH: 10
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Thr Trp Asp Asp Asn Leu Arg Gly Trp
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Tyr Thr Phe Thr Ser Phe Gly Ile Asn
1               5                   10

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Met Asn Ser Asn Ser Gly Asp Ala Asp Ser Ala Gln Lys Phe
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Met Asn Phe Arg Gly Ser Lys Trp Glu Val Asn Trp Phe Asp Pro
1               5                   10                  15

<210> SEQ ID NO 208
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Gly Ser Arg Ser Asn Val Glu Arg Asn Phe Val Tyr
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 209

Met Asn Ser Gln Arg Pro Ser
1               5

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Thr Trp Asp Asp Asn Leu Arg Gly Trp
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Tyr Thr Phe Thr Arg Phe Gly Ile Asn
1               5                   10

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Trp Met Asn Ser Asn Ser Gly Asn Ala Asp Ser Ala Gln Lys Phe
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Met Asn Tyr Arg Gly Ser Lys Trp Glu Ile Asn Trp Phe Asp Pro
1               5                   10                  15

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Gly Ser Arg Ser Asn Val Gln Arg Asn Phe Val Tyr
1               5                   10

<210> SEQ ID NO 215
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Met Asn Asn Asn Arg Pro Ser
1               5

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Thr Trp Asp Asp Asn Leu Arg Gly Trp
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Tyr Thr Phe Thr Gly Phe Gly Ile Asn
1               5                   10

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Met Asn Ser Asn Thr Gly Asp Ala Asp Ser Ala Gln Lys Phe
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Met Asn Phe Leu Gly Ser Lys Trp Glu Val Asn Trp Phe Asp Pro
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 220

Arg Ser Ser His Ser Leu Pro Arg Asp Asp Glu Tyr Ser Tyr Leu Asn
1               5                   10                  15

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Val Ser Lys Arg Asp Ser
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Met Gln Gly Thr Tyr Trp Pro Gly Thr
1               5

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Tyr Ile Phe Thr Asn Phe Gly Ile Asn
1               5                   10

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Met Asn Ser Lys Tyr Gly Asn Ala Asp Ser Ala His Lys Phe
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Met Asn Tyr Arg Asp Ser Lys Trp Asp Val Asn Trp Phe Asp Pro
1               5                   10                  15

<210> SEQ ID NO 226
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ser Gly Ser Arg Ser Asn Val Glu Arg Asn Phe Val Tyr
1               5                   10

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Met Asn Asn Gln Arg Pro Ser
1               5

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Val Trp Asp Asp Asn Leu Arg Gly Trp
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Tyr Ile Phe Thr Ser Phe Gly Ile Asn
1               5                   10

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Met Asn Ser Asn Thr Gly Asp Ala Asp Ser Val Gln Lys Phe
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 231

Met Asn Phe Phe Gly Ser Gln Trp Glu Val Asn Trp Phe Asp Pro
1               5                   10                  15

<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Gly Ser Arg Ser Asn Val Glu Arg Asn Ser Val Tyr
1               5                   10

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Met Ser Asn Gln Arg Pro Ser
1               5

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ala Val Trp Asp Asp Asn Leu Arg Gly Trp
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Tyr Thr Phe Thr Arg Phe Gly Ile Asn
1               5                   10

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Trp Met Asn Ser Asn Thr Gly Asp Ala Asp Ser Ala Gln Lys Phe
1               5                   10                  15

<210> SEQ ID NO 237
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Met Asn Tyr Trp Gly Ser Lys Trp Asp Val Asn Trp Phe Asp Pro
1               5                   10                  15

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Gly Arg Arg Thr Asn Val Glu Arg Asn Ser Val Tyr
1               5                   10

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Met Ser Asn Lys Arg Pro Ser
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Val Trp Asp Asp Asn Leu Arg Gly Trp
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Tyr Thr Phe Thr Asn Tyr Gly Val Asn
1               5                   10

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 242

Trp Met Asn Thr Asn Ser Gly Asp Thr Gly Tyr Ala Gln Lys Phe
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Tyr Phe Phe Asp Ser Trp Asn Lys Gly Asn Trp Phe Asp Pro
1               5                   10                  15

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ser Gly Gly Ser Ser Asn Leu Gly Arg Ser Tyr Ile Tyr
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Lys Asn Ser Gln Arg Pro Ser
1               5

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Ala Trp Asp Asp Ser Leu Ser Gly Ser Trp
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gly Tyr Val Thr Ile Lys Asp Asn Tyr Trp Val
1               5                   10

<210> SEQ ID NO 248
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Met Ser Tyr Ser Gly Asn Ala Tyr Tyr Asn Pro Ser Leu
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Arg Ser Ala Ala Ala Gly Gly Gly Asn Glu Trp Phe Asp Pro
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Gly Ser Thr Phe Asn Ile Gly Asn Asn Tyr Val Ser
1               5                   10

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asp Asn Asp Lys Arg Pro Ser
1               5

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Thr Trp Asp Asn Arg Leu Asp Ala Val
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 253

Gly Phe Ala Phe Thr Thr Ala Trp Met Thr
1               5                   10

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Leu Ile Lys Ser Thr Asn Asp Gly Gly Ser Ile Asp Tyr Ala Ala Pro
1               5                   10                  15

Val

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asn Asp Val Val Arg Leu Arg Gly Val Thr Pro Pro Ile Leu Leu
1               5                   10                  15

<210> SEQ ID NO 256
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Thr Leu Ser Ser Gly His His Ser Tyr Pro Val Ala
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Asn Gly Asp Gly Ser His Thr Lys Gly Asp Gly
1               5                   10

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Thr Trp Ala Thr Gly Trp
1               5

```
<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Tyr Ile Phe Thr Asn Phe Gly Ile Asn
1               5                   10

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Trp Met Asn Ser Arg Thr Gly Asp Ala Asp Ser Ala Gln Asn Phe
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Met Asn Phe Leu Gly Ser Arg Trp Glu Val Asn Trp Phe Asp Pro
1               5                   10                  15

<210> SEQ ID NO 262
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ser Gly Ser Arg Ser Asn Val Glu Arg Asn Phe Phe Tyr
1               5                   10

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Met Asn Ser Gln Arg Pro Ala Gly
1               5

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 264

Ala Thr Trp Asp Asp Asn Leu Arg Gly Trp
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Tyr Ile Phe Thr Ser Phe Gly Ile Asn
1               5                   10

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Trp Met Asn Ser Asn Thr Gly Asp Ala Asp Ser Leu Gln Lys Phe
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Met Asn Phe His Gly Ser Arg Trp Asp Val Asn Trp Phe Asp Pro
1               5                   10                  15

<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ser Gly Ser Gly Ser Asn Val Glu Arg Asn Ser Val Tyr
1               5                   10

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Met Ser Asn Arg Pro Arg Ser Gly
1               5

<210> SEQ ID NO 270
<211> LENGTH: 10
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Val Trp Asp Asp Ser Leu Arg Gly Trp
1               5                   10
```

HUMAN ANTIBODIES, PHARMACEUTICAL COMPOSITIONS AND METHODS

CROSS-REFERENCE TO RELATED APPLICATIONS

This application claims the priority to and benefit of International Patent Application No. PCT/US2017/044713, filed Jul. 27, 2017, which claims priorty to and benefit of U.S. Provisional Patent Application No. 62/368,407, filed Jul. 29, 2016. The entirety of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Jan. 28, 2019, is named G3004-00809_SL.txt and is 137,284 bytes in size.

FIELD

The present disclosure relates to human antibodies and binding fragments thereof to carbohydrate antigens, as well as nucleic acids encoding such antibodies, complementary nucleic acids, polypeptides, vectors, host cells and methods of making and using thereof, including pharmaceutical compositions comprising said antibody and/or binding fragments. Further, methods are provided for administering antibodies to a subject in an amount effective to inhibit cancer cells. Specifically, antibodies that bind to stage-specific embryonic antigen 3 (SSEA-3), stage-specific embryonic antigen 4 (SSEA-4) and Globo H are disclosed herein, as well as related compositions and methods of use. Methods of use include, without limitation, cancer therapies and diagnostics.

BACKGROUND OF THE INVENTION

Recent advances in the isolation, culture and expansion of human B cells are enabling the isolation of large numbers of human antibodies to be used for cancer diagnostics and therapeutics. For several decades, mouse monoclonal antibodies were isolated using the hybridoma technology. However, the therapeutic application of these antibodies was limited by induction of anti-mouse antibodies and autoreactivity. More recently, monoclonal antibodies have been isolated through phage display libraries produced from humans with a humoral response of interest (Mao S, et al. (1999) Proc Natl Acad Sci USA; 96:6953-6958.). Although this technique has produced numerous useful antibodies, its applicability is limited by differences in binding properties between antibodies expressed in bacterial and eukaryotic cells. In addition, phage display may result in heavy- and light-chain combinations that do not occur in the same B cell in vivo.

Numerous surface carbohydrates are expressed in malignant tumor cells. For example, the carbohydrate antigen Globo H (Fucα1→2 Galβ1→>3 GalNAcβ1→3 Galα1→4 Galβ1→4 Glc) was first isolated as a ceramide-linked Glycolipid and identified in 1984 from breast cancer MCF-7 cells. (Bremer E G, et al. (1984) J Biol Chem 259:14773-14777). Previous studies have also shown that Globo H and stage-specific embryonic antigen 3 (2Gal β1→3GalNAcβ1→3Galα1→4Galβ1→4Glcβ1) (SSEA-3, also called Gb5) were observed on breast cancer cells and breast cancer stem cells (WW Chang et al. (2008) Proc Natl Acad Sci USA, 105(33): 11667-11672). In addition, SSEA-4 (stage-specific embryonic antigen-4) (Neu5Acα2→3Galβ1→3GalNAcβ1→3Galα1→4Galβ1→>4Glcβ1) has been commonly used as a cell surface marker for pluripotent human embryonic stem cells and has been used to isolate mesenchymal stem cells and enrich neural progenitor cells (Kannagi R et al. (1983) EMBO J, 2:2355-2361). Thus, it is of great interest to identify glycan markers associated with and/or predictive of cancers, and develop human monoclonal antibodies against the markers for use in diagnosing and treating a broad spectrum of cancers.

SUMMARY OF THE INVENTION

Accordingly, the present disclosure is based on the discovery that Globo series antigens (Globo H, SSEA-3 and SSEA-4) are aberrantly expressed in a broad spectrum of cancers, but not on normal cells. Thus, human monoclonal antibodies to Globo series antigens (Globo H, SSEA-3 and SSEA-4) can address the unmet need for effective treatment and/or prevention for cancer. Cancer cells expressing Globo series antigens can include, but are not limited to, sarcoma, skin cancer, leukemia, lymphoma, brain cancer, lung cancer, breast cancer, oral cancer, esophageal cancer, stomach cancer, liver cancer, bile duct cancer, pancreatic cancer, colon cancer, kidney cancer, cervical cancer, ovarian cancer and prostate cancer.

In one aspect, the present disclosure is directed to antibodies or binding fragments thereof specific to Globo series antigens.

In order to generate anti-Globo series antigens human monoclonal antibodies, human B cells are isolated from peripheral blood of vaccinated subjects, plated at a density of one cell per well and cultured for secreted IgG production. The secreted IgGs are assayed for Globo H, SSEA-3 or SSEA-4 binding specificities. Genes encoding Ig VH, Ig Vκ or Ig Vλ from positive wells are recovered using RT-PCR and cloned into expression vectors for generating anti-Globo H, SSEA-3 or SSEA-4 human monoclonal antibody. In one embodiment, the light chains of the antibody is kappa type. In one embodiment, the light chain of the antibody is lamda type.

In one aspect, the present disclosure provides an antibody, and/or an antigen-binding fragment thereof, comprising: a heavy chain variable domain (VH) comprising respective CDRs as disclosed herein and an amino acid sequence of at least about 80%, 81, 82, 83, 84, 85, 86, 87, 88, 89, 90, 91, 92, 93, 94, 95, 96, 97 98, or 99% sequence homology to the amino acid sequences as disclosed herein and/or a light chain variable domain (VL) comprising respective CDRs as disclosed herein and an amino acid sequence of at least about 80%, 81, 82, 83, 84, 85, 86, 87, 88, 89, 90, 91, 92, 93, 94, 95, 96, 97 98, or 99% sequence homology to the amino acid sequences as disclosed herein respectively.

In one aspect, the present disclosure provides an antibody, or an antigen-binding fragment thereof capable of targeting the Globo-Series carbohydrate antigen, comprising: three heavy chain CDRs and corresponding three light chain CDRs of each respective clones as disclosed herein such as the ones disclosed in Tables 1-28.

In another aspect, the present disclosure provides the antibody or antigen-binding fragment thereof comprising: the heavy chain variable domain comprising an amino acid sequence having at least about 80% identity to the full length heavy chain sequences of each clone as disclosed herein in Tables 1-28 further comprising the three corresponding heavy chain complementarity determining regions (CDRs), CDR1, CDR2 and CDR3 sequences of the said corresponding clone; and the light chain variable domain comprising an amino acid sequence having at least about 80% identity to the full length light chain sequences of said clone as disclosed herein in Tables 1-28 further comprising the three corresponding light chain complementarity determining regions (CDRs), CDR1, CDR2 and CDR3 sequences of said corresponding clone.

For example, the present disclosure provides an antibody, or an antigen-binding fragment thereof capable of targeting the Globo-Series carbohydrate antigen, comprising: a three heavy chain CDRs of SEQ ID NOs: 257, 258 and 259 or conservatively modified amino acid substitutions; and/or b. three light chain CDRs of SEQ ID NOs: 260, 261, and 262 or conservatively modified amino acid substitutions. In another embodiment, the antibody or antigen-binding fragment thereof of the above, comprising: the light chain variable domain comprising an amino acid sequence having at least about 80% identity to SEQ ID NO: 3 further comprising the three heavy chain complementarity determining regions (CDRs), CDR1, CDR2 and CDR3 (SEQ ID Nos 257, 258, 259); and/or the light chain variable domain comprising an amino acid sequence having at least about 80% identity to SEQ ID NO: 4 further comprising the three light chain complementarity determining regions (CDRs), CDR1, CDR2 and CDR3 (SEQ ID Nos: 260, 261, 262). The same can be repeated for each of the clones recited in Tables 1-28 with the respective full length heavy chain and light chain sequences of each clone and their respective corresponding heavy chain and light chain CDRs.

In certain embodiments, the antibody or antigen-binding fragment thereof is selected from: (a) a whole immunoglobulin molecule; (b) an scFv; (c) a Fab fragment; (d) an F(ab')2; or (e) a disulfide linked Fv.

In certain embodiments, the antibody is an IgG or IgM.

In one aspect, the present disclosure provides a pharmaceutical composition, comprising:
an antibody or an antigen-binding fragment thereof; and at least one pharmaceutically acceptable carrier.

In certain embodiments, the pharmaceutical composition further comprising at least one additional therapeutic agent.

In one aspect, the present disclosure provides a method for inhibiting the proliferation of cancer cells, comprising the administering of an effective amount of an exemplary pharmaceutical composition to a subject in need thereof, wherein the proliferation of cancer cells is inhibited and/or decreased.

In certain embodiments, the present disclosure provides a method of treating cancer in a subject, the method comprising administering to a subject in need thereof an effective amount of the exemplary human antibody described herein.

In certain embodiments, the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophageal cancer, stomach cancer, liver cancer, bile duct cancer, gallbladder cancer, bladder cancer, pancreatic cancer, intestinal cancer, colorectal cancer, kidney cancer, cervical cancer, endometrial cancer, ovarian cancer, testicular cancer, buccal cancer, oropharyngeal cancer, laryngeal cancer and prostate cancer.

In one aspect, the present disclosure provides a method for staging cancer in a subject, comprising:
(a) applying one or more antibodies that detect expression of Globo series antigens to a cell or tissue sample obtained from the subject;
(b) assaying the binding of the one or more antibodies to the cell or the tissue sample;
(c) comparing the binding with a normal control to determine the presence of the cancer in the subject; and
(d) categorizing disease progression stage based on relative levels of corresponding antibody binding compared to normal baseline index.

In one aspect, the present disclosure provides a method for inhibiting the proliferation of cancer cells, comprising the administering of an effective amount of an pharmaceutical composition comprising an antibody or an antigen-binding fragment thereof targeting Globo-series carbohydrate antigens to a subject in need thereof, wherein the proliferation of cancer cells is inhibited. In one embodiment, the subject is human.

In one aspect, the present disclosure provides a method of treating cancer in a subject, the method comprising administering to the subject in need thereof an effective amount of the antibody or an antigen-binding fragment thereof targeting Globo-series carbohydrate antigens.

In one embodiment, the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer. In one embodiment, the subject is human.

In one aspect, the present disclosure provides a method for cancer diagnosis in a subject, comprising:
(a) Applying one or more antibodies or binding fragments as disclosed herein that detect expression of a panel of markers to a cell or sample obtained from the subject;
(b) Assaying the binding of the one or more antibodies to the cell or the sample; and
(c) Comparing the binding with a normal control to determine the presence of the cancer in the subject.

In one embodiment, the markers consisting of Globo-H, SSEA-3 or SSEA-4.

In one embodiment, the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

In one embodiment, the cell is cancer stem cell.

In another embodiment, the sample consists serum, blood, plasma, cells, cell medium, saliva, urine, lymph node fluid, tumor biopsy or tissue culture. In one embodiment, the subject is human.

In one aspect, the present disclosure provides a method of imaging a subject comprising:
(a) Administering an effective amount of an antibody or an antigen-binding fragment thereof as disclosed herein wherein the antibody or an antigen-binding fragment is conjugated to an imaging agent; and (b) Detecting the imaging agent in the subject.

In one embodiment, the imaging agent is a fluorophore, a dye, an MRI contrast agent or a radionuclide.

In one embodiment, the subject has a cancer, the method further defined as a method of detecting a cancer metastasis. In one embodiment, the subject is human.

In one aspect, the present disclosure provides a method of isolating an antibody, or an antigen-binding fragment in a subject, comprising:
(a) Administering to the subject a therapeutically effective dose of Globo series antigens vaccine and a pharmaceutically acceptable carrier:
(b) Collecting a sample from the subject;
(c) Isolating B cells from the sample; and
(d) Cultivating and screening the B cells which bind to the Globo series antigens.

In one embodiment, the Globo series antigens comprising Globo-H, SSEA-3 or SSEA-4. In one embodiment, the subject is human.

In one embodiment, the sample consists serum, blood, plasma, cells, cell medium, lymph node fluid, tumor biopsy or tissue culture.

In one aspect, the present disclosure provides an antibody-drug conjugate (ADC) comprising a drug conjugated to an antibody or an antigen-binding fragment that binds Globo series antigens, wherein VH selected from SEQ ID No: 3, SEQ ID No: 7, SEQ ID No: 11, SEQ ID No: 15, SEQ ID No: 19, SEQ ID No: 23, SEQ ID No: 27, SEQ ID No: 31, SEQ ID No: 35, SEQ ID No: 39, SEQ ID No: 43, SEQ ID No: 47, SEQ ID No: 51, SEQ ID No: 55, SEQ ID No: 59, SEQ ID No: 63, SEQ ID No: 67, SEQ ID No: 71, SEQ ID No: 75, SEQ ID No: 79, SEQ ID No: 83, SEQ ID No: 87, SEQ ID No: 91, SEQ ID No: 95, SEQ ID No: 99, SEQ ID No: 103, or SEQ ID No: 107 and VL selected from SEQ ID No: 4, SEQ ID No: 8, SEQ ID No: 12, SEQ ID No: 16, SEQ ID No: 20, SEQ ID No: 24, SEQ ID No: 28, SEQ ID No: 32, SEQ ID No: 36, SEQ ID No: 40, SEQ ID No: 44, SEQ ID No: 48, SEQ ID No: 52, SEQ ID No: 56, SEQ ID No: 60, SEQ ID No: 64, SEQ ID No: 68, SEQ ID No: 72, SEQ ID No: 76, SEQ ID No: 80, SEQ ID No: 84, SEQ ID No: 88, SEQ ID No: 92, SEQ ID No: 96, SEQ ID No: 100, SEQ ID No: 104, or SEQ ID No: 108.; and wherein the drug is covalently conjugated to the antibody or the antigen-binding fragment by a linker.

In one embodiment, the Globo series antigens comprising Globo-H, SSEA-3 or SSEA-4.

In one embodiment, the linker comprising a p-nitrophenyl linker, a 4-(4-N-maleimidomethyl) cyclohexane-1-carboxyl hydrazide (MMCCH) linker, a maleimidocaproyl (MC) linker or a maleimidomethyl cyclohexane-1-carboxylate (MCC) linker. In one embodiment, the drug is a chemical compound or a biological agent. In one embodiment, the drug is an anti-proliferative agent.

In one embodiment, the anti-proliferative agent is selected from cyclophosphamide, opiate, granulocyte colony-stimulating factor (GCSF), estrogen inhibitors (tamoxifen or Fareston), aromatase inhibitors (Arimidex, Aromasin or Femara), pituitary downregulators (Zoladex or Lupron), Novaldex (tamoxifen selective estrogen-receptor modulator), Evista (rolaxifene), Faslodex (estrogen receptor downregulator), anticoagulant (Refludan), enzyme (Elitek), Hematopoietic growth factor, anti-neoplastic Agent (antimetabolites, miscellaneous cytotoxic agents, vinca alkaloid, Epipodophyllotoxins, Alkylating agents, Taxanes, Antitumor antibiotics, Camptothecins, Nitrosoureas), HER1/EGFR tyrosine kinase inhibitor (Tarceva), VEGF protein inhibitor (Avastin), HER-2/ErbB2 inhibitor (Tyverb/Tykerb), Interferon, Interleukin, Monoclonal antibody, or Glucocorticoid steroid.

In one embodiment, the anti-proliferative agent is selected from erlotinib (TARCEVA); docetaxel (TAXOTERE); gemcitabine (GEMZAR); cisplatin; carboplatin; paclitaxel (TAXOL); trastuzumab (HERCEPTIN); temozolomide (TEMODAL); tamoxifen (NOLVADEX, ISTUBAL, VALODEX); doxorubicin (ADRIAMYCIN); oxaliplatin (ELOXATIN); bortezomib (VELCADE); sutent (SUNITINIB); letrozole (FEMARA); imatinib mesylate (GLEEVEC); MEK inhibitor (Exelixis); fulvestrant (FASLODEX); leucovorin (folinic acid); rapamycin (RAPAMUNE); lapatinib (TYKERB); lonafarnib (SARASAR); sorafenib (NEXAVAR); gefitinib (IRESSA); irinotecan (CAMPTOSAR); tipifarnib (ZARNESTRA); ABRAXANE (Cremophor-free); paclitaxel; vandetanib (ZACTIMA); chloranmbucil; temsirolimus (TORISEL); pazopanib; canfosfamide (TELCYTA); thiotepa; cyclophosphamide (CYTOXAN, NEOSAR); 5-fluorouracil (5-FU); vinorelbine (NAVELBINE); novantrone; teniposide; edatrexate; daunomycin; aminopterin; capecitabine (XELODA); ibandronate; topoisomerase inhibitor RFS 2000; -difluoromethylornithine (DMFO); tamoxifen (NOLVADEX); raloxifene; droloxifene, 4-hydroxytamoxifen; trioxifene; keoxifene; onapristone; FARESTON (toremifine citrate); 4(5)-imidazoles; aminoglutethimide; MEGASE (megestrol acetate); AROMASIN (exemestane); formestanie; fadrozole; RIVISOR® (vorozole); FEMARA (letrozole); ARIMIDEX (anastrozole); flutamide; nilutamide; bicalutamide; leuprolide; goserelin; troxacitabine (α-1,3-dioxolane nucleoside cytosine analog); lipid kinase inhibitor; oblimersen (GENASENSE); ANGIOZYME; ALLOVECTIN; LEUVECTIN; VAXID; PROLEUKIN; LURTOTECAN; ABARELIX; bevacizumab (AVASTIN); alemtuzumab (Campath); bevacizumab (AVASTIN); cetuximab (ERBITUX); panitumumab (VECTIBIX); rituximab (RITUXAN); pertuzumab (OMNITARG); trastuzumab (HERCEPTIN); tositumomab (Bexxar, Corixia); gemtuzumab; or ozogamicin (MYLOTARG).

In one aspect, the present disclosure provides a method of treating cancer in a subject, the method comprising administering to the subject in need thereof an effective amount of the ADC as disclosed herein.

In one embodiment, the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer. In one embodiment, the subject is human.

The details of one or more embodiments of the invention are set forth in the description below. Other features or advantages of the present invention will be apparent from the following drawings and detailed description of several embodiments, and also from the appending claims.

BRIEF DESCRIPTION OF THE FIGURES

A more complete understanding of the invention may be obtained by reference to the accompanying drawings, when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

Figure 1A:
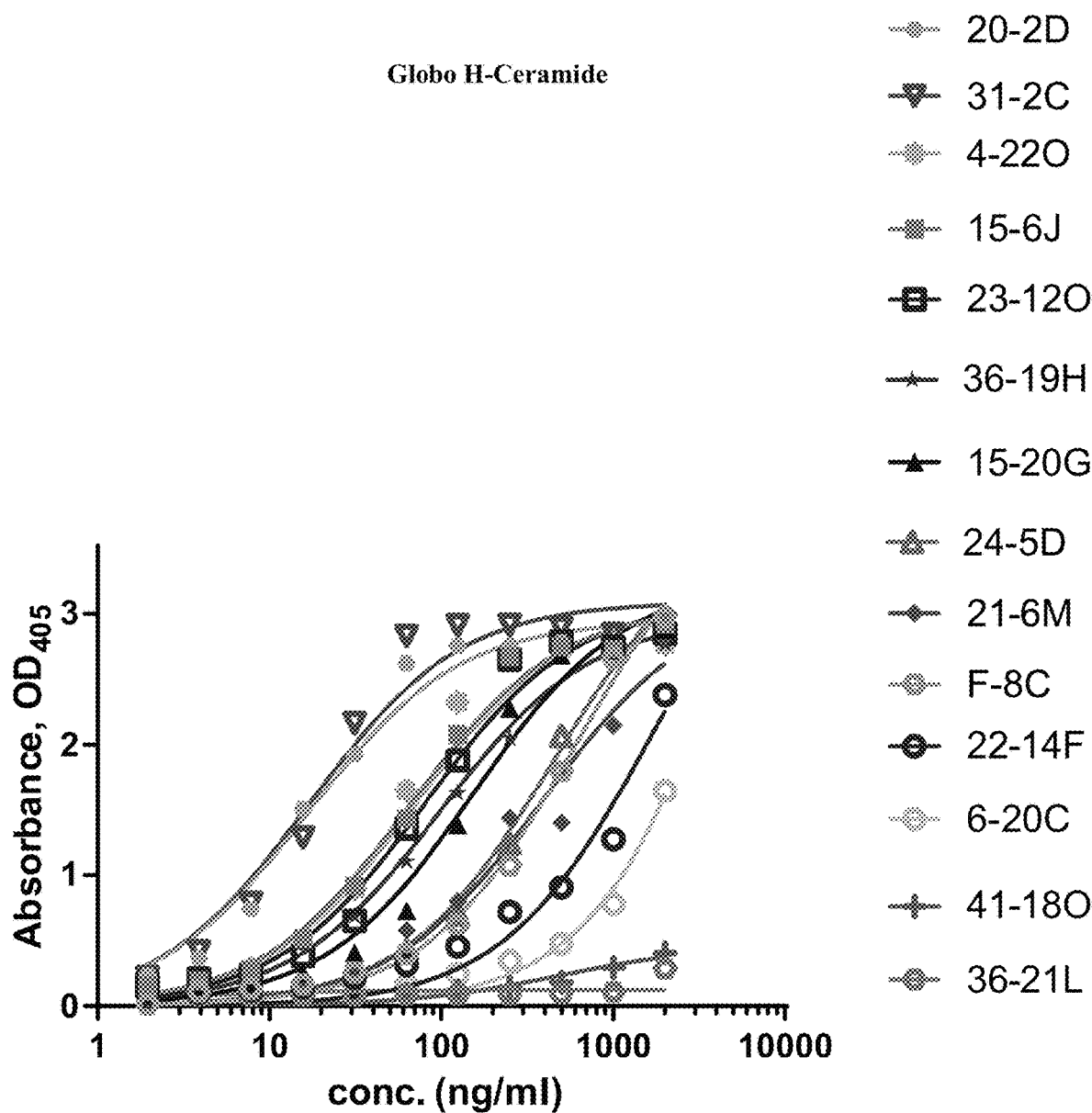
FIG. 1A uses Globo H-ceramide and FIG. 1B uses Globo H-lipid as the coating antigens.

Accordingly, antibody methods and compositions directed to the markers for use in diagnosing and treating a broad spectrum of cancers are provided. Anti-Globo series antigens human antibodies were developed and disclosed herein. Methods of use include, without limitation, cancer therapies and diagnostics. The antibodies described herein can bind to a broad spectrum of Globo series antigens-expressing cancer cells, thereby facilitating cancer diagnosis and treatment. Cells that can be targeted by the antibodies include carcinomas, such as those in skin, blood, lymph node, brain, lung, breast, mouse, esophagus, stomach, liver, bile duct, pancreas, colon, kidney, cervix, ovary, prostate cancer, etc.

Definitions

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of ß-1,4-linked D-glucose, and chitin is a glycan composed of ß-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)).

The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816, 567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851

(1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

Antibodies of the present invention can also include chimerized monoclonal antibodies generated from antibodies of the present invention.

The antibodies can be full-length or can comprise a fragment (or fragments) of the antibody having an antigen-binding portion, including, but not limited to, Fab, F(ab')$_2$, Fab', F(ab)', Fv, single chain Fv (scFv), bivalent scFv (bi-scFv), trivalent scFv (tri-scFv), Fd, dAb fragment (e.g., Ward et al, Nature, 341:544-546 (1989)), an CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al, Proc. Natl. Acad. Sci. USA, 1988, 85:5879-5883.

The antibodies or antigen-binding portions thereof of the present invention may be monospecific, bi-specific or multispecific.

All antibody isotypes are encompassed by the present invention, including IgG (e.g., IgG$_1$, IgG$_2$, IgG$_3$, IgG$_4$), IgM, IgA (IgA$_1$, IgA$_2$), IgD or IgE (all classes and subclasses are encompassed by the present invention). The antibodies or antigen-binding portions thereof may be mammalian (e.g., mouse, human) antibodies or antigen-binding portions thereof. The light chains of the antibody may be of kappa or lambda type.

Thus, anti-cancer antibodies of the present invention include in combination with a heavy chain or light chain variable region, a heavy chain or light chain constant region, a framework region, or any portion thereof, of non-murine origin, preferably of human origin, which can be incorporated into an antibody of the present invention.

Antibodies with a variable heavy chain region and a variable light chain region that are at least about 70%, at least about 75%, at least about 80%, at least about 81%, at least about 82%, at least about 83%, at least about 84%, at least about 85%, at least about 86% o, at least about 87%>, at least about 88%>, at least about 89%>, at least about 90%>, at least about 91>, at least about 92%>, at least about 93%>, at least about 94%>, at least about 95%), at least about 96%>, at least about 97%>, at least about 98%>, at least about 99%> or about 100% homologous to the variable heavy chain region and variable light chain region of the antibody produced by the reference antibody, and can also bind to a carbohydrate antigen (e.g. Globo H, SSEA-3 or SSEA-4). Homology can be present at either the amino acid or nucleotide sequence level.

As used herein, substantially "homology" and/or "homologous sequences" of proteins of the invention include, without limitation, conservative amino acid substitutions, or for example alterations that do not effect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson et al., 1994). If desired, the Clustal W algorithm can be used together with BLOSUM 62 scoring matrix (Henikoff and Henikoff, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (1970), as revised by Smith and Waterman (1981) so that the highest order match is obtained between the two sequences and the number of identical amino acids is determined between the two sequences. Other methods to calculate the percentage identity between two amino acid sequences are generally art recognized and include, for example, those described by Carillo and Lipton (1988) and those described in Computational Molecular Biology, Lesk, e.d. Oxford University Press, New York, 1988, Biocomputing: Informatics and Genomics Projects.

Generally, computer programs can be employed for such calculations. Programs that compare and align pairs of sequences, like ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984) are also useful for this purpose. Furthermore, the Dali server at the European Bioinformatics institute offers structure-based alignments of protein sequences (Holm, 1993; 1995; 1998).

The antibodies or antigen-binding portions may be peptides. Such peptides can include variants, analogs, orthologs, homologs and derivatives of peptides, that exhibit a biological activity, e.g., binding of a carbohydrate antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

Also within the scope of the invention are antibodies or antigen-binding portions thereof in which specific amino acids have been substituted, deleted or added. In an exemplary embodiment, these alternations do not have a substantial effect on the peptide's biological properties such as binding affinity. In another exemplary embodiment, antibodies may have amino acid substitutions in the framework region, such as to improve binding affinity of the antibody to the antigen. In yet another exemplary embodiment, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al, Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256: 1443-45 (1992).

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

Nucleic acids encoding a functionally active variant of the present antibody or antigen-binding portion thereof are also encompassed by the present invention. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: 1) medium stringency hybridization conditions: 6×SSC at about 45° C., followed by one or more washes in 0.2×SSC, 0.1% SDS at 60° C.; 2) high stringency hybridization conditions: 6×SSC at about 45° C., followed by one or more washes in 0.2×SSC, 0.1% SDS at 65° C.; and 3) very high stringency hybridization conditions: 0.5 M sodium phosphate, 7% SDS at 65° C., followed by one or more washes at 0.2×SSC, 1% SDS at 65° C.

A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al, Proc Natl Acad Sci USA, 86: 10029-10033 (1989).

The present antibodies or antigen-binding portions thereof can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

As used herein, "substantially purified" or "substantially isolated" refers to a molecule (e.g. a compound) in a state that it is separated from substantially all other molecules normally associated with it in its native state. Preferably, a substantially purified molecule is the predominant species present in a preparation. Particularly, a substantially purified molecule may be greater than 60% free, preferably 75% free, or 85%, 86%, 87%, 88%, 89%, 90%, 91%, 92%, 93%, 94%, 95%, 96%, 97%, 97.5%, 98%, 98.5%, 99%, or 99.5% free, or any range between any two recited percentages free from the other molecules (exclusive of solvent) present in the natural mixture.

The present nucleic acids can be expressed in various suitable cells, including prokaryotic and eukaryotic cells, e.g., bacterial cells, (e.g., $E.\ coli$), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO), NSO, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present invention also provides for cells comprising the nucleic acids described herein. The cells may be a hybridoma or transfectant.

Alternatively, the present antibody or antigen-binding portion thereof can be synthesized by solid phase procedures well known in the art. Solid Phase Peptide Synthesis: A Practical Approach by E. Atherton and R. C. Sheppard, published by IRL at Oxford University Press (1989). Methods in Molecular Biology, Vol. 35: Peptide Synthesis Protocols (ed. M. W. Pennington and B. M. Dunn), chapter 7. Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)).

"Framework" or "FW" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor" as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

As used herein, "treatment" refers to clinical intervention in an attempt to alter the natural course of the individual or cell being treated, and can be performed either for prophylaxis or during the course of clinical pathology. "Treating" or "treating" is referred to herein as administration of a therapeutic composition to a subject with the purpose to cure, alleviate, relieve, remedy, prevent, or ameliorate a disorder, symptoms of the disorder, a disease state secondary to the disorder, or predisposition toward the disorder. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

Antibodies Targeting Globo Series Antigens

One aspect of the present disclosure features the new antibody targeting the Globo series antigens (Globo H, SSEA-3, SSEA-4).

Cancers expressing Globo series antigens (SSEA-4, Globo H or SSEA-3) include, but are not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer.

"SSEA-4 moiety" is defined herein to be a glycan (i.e., a molecule containing a sugar moiety) that is SSEA-4 or a fragment or analog thereof. SSEA-4 is a glycan containing the hexasaccharide epitope (Neu5Acα2→3Galβ1→3GalNAcβ1→3Galα1→4Galβ1→4Glcβ1), and optionally, a non-sugar moiety. Its fragment is a glycan containing a fragment of the hexasaccharide epitope and, if applicable, the non-sugar moiety.

"Globo H moiety" is defined herein to be a glycan (i.e., a molecule containing a sugar moiety) that is Globo H or a fragment or analog thereof. Globo H is a glycan containing the hexasaccharide epitope (Fucα1→2 Galβ1→3 GalNAcβ1→3 Galα1→4 Galβ1→4 Glc), and optionally, a non-sugar moiety. Its fragment is a glycan containing a fragment of the hexasaccharide epitope and, if applicable, the non-sugar moiety.

"SSEA-3 moiety" is defined herein to be a glycan (i.e., a molecule containing a sugar moiety) that is SSEA-3 or a fragment or analog thereof. SSEA-3 is a glycan containing the pentasaccharide epitope (Galβ1→3GalNAcβ1→3Galα1→4Galβ1→4Glcβ1), and optionally, a non-sugar moiety. Its fragment is a glycan containing a fragment of the hexasaccharide epitope and, if applicable, the non-sugar moiety.

Exemplars and their amino acid and nucleic acid structures/sequences are provided below:

TABLE 1

Amino Acid and Nucleotide Sequences of Human Antibody 2-8M

| SEQ ID NO | DESCRIPTION | SEQUENCE |
|---|---|---|
| 1 | 2-8M VH nucleotide sequence | CAGCTGCAGTTGCAGGAGTCGGGCCCAGGACTGGT GAAGCCTGCGGAGACCCTGTCCCTCACCTGCTCTGT CTCCGGTGGCTACGTCACCATCAAGGATAATTATTG GGTCTGGTTCCGCCAGTCCCCAGGGAAGGAGCCGG AGTGGATTGGGAGTATGTCTTATAGTGGGAATGCCT ACTACAACCCGTCCCTCAAGAGTCGAGCCAGCATTT CCATAGACCGGTACAGGAACCAGTTCTCCCTGAGGT TGACTTCTGTGACCGCCGCAGACACGTCCATGTACT ACTGTGCGAGACGATCAGCAGCAGCTGGTGGGGGG AATGAATGGTTCGACCCCTGGGGCCAAGGAGCCCTT GTCACCGTCTCCTCA |
| 2 | 2-8M VL nucleotide sequence | CAGTCTGCTTTGACGCAGCCGCCCTCAGTGTCTGCG GCCCCAGGACGGAAGGTCGACATCTCCTGCTCTGGA AGCACCTTCAATATTGGGAACAATTATGTGTCGTGG TACCGGCAGTTCCCAGGAACAGCCCCCAAACTCCTC ATTTATGACAATGATAAGCGACCCTCAGGCATTCCT GACCGATTCTCTGGCTCCAGGTTCGGCACGTCAGCC ACCCTGGGCATCACCGGACTCCAGACTGACGACGA GGCCATTTATTACTGCGCAACATGGGATAACAGACT GGATGCTGTGGTTTTCGGCGGGGGGACCGAGTTGAT CGTCCTT |
| 3 | 2-8M VH amino acid sequence | QLQLQESGPGLVKPAETLSLTCSVSGGYVTIKDNYWV WFRQSPGKEPEWIGSMSYSGNAYYNPSLKSRASISIDR YRNQFSLRLTSVTAADTSMYYCARRSAAAGGGNEWF DPWGQGALVTVSS |
| 4 | 2-8M VL amino acid sequence | QSALTQPPSVSAAPGRKVDISCSGSTFNIGNNYVSWYR QFPGTAPKLLIYDNDKRPSGIPDRFSGSRFGTSATLGIT GLQTDDEAIYYCATWDNRLDAVVFGGGTELIVL |

TABLE 2

Amino Acid and Nucleotide Sequences of Antibody 6-8N

| SEQ ID NO | DESCRIPTION | SEQUENCE |
|---|---|---|
| 5 | 6-8N VH nucleotide sequence | GAGGTGCACCTGGTGGAGTCTGGGGGAGGCCTGGT AAACCCGGGGGGGTCCCTTAGACTCTCCTGTTCAGC CTCTGGCTTCGCTTTCACTACCGCCTGGATGACCTGG GCCCGCCAGGCTCCAGGGAAGGGACTGGAATGGAT TGGCCTTATTAAAAGCACAAATGATGGTGGGTCTAT AGACTACGCTGCACCCGTGCAAGGCAGATTCACCAT CTCAAGAGATGATTCAAAGAACACGATTTACCTCCA AATGAGCAGCCTCAAAGCCGAGGACTCAGCCGTCT ACTATTGTGCCACAAACGATGTTGTTCGGCTTCGAG GGGTTACCCCCCCCATACTTCTGTGGGGCCAGGGGA CCCTGATCACCGTCTCCTCA |
| 6 | 6-8N VL nucleotide sequence | CAGCTTGTACTGACTCAATCGCCCTCAACCTCTGCCT CCCTGGGAGCCCCGGTCACACTCACCTGCACTCTGA GCAGTGGGCACCACAGCTACCCCGTCGCATGGCATC AGAAGCACCCAGAGAAGGGCCCTCGATACTTGATG AAGATTAACGGAGATGGCAGCCACACCAAGGGGGA CGGTATCCCTGATCGCTTCTCAGGCTCCAGCTCTGG GACTGGGCGCTATCTCACCATCTCCAGCCTCCAGTC TGAGGATGAGGCTGACTATTACTGTCAGACCTGGGC CACTGGATGGGTGTTCGGCGGAGGGACCAAACTGA CCGTCCTA |
| 7 | 6-8N VH amino acid sequence | EVHLVESGGGLVNPGGSLRLSCSASGFAFTTAWMTW ARQAPGKGLEWIGLIKSTNDGGSIDYAAPVQGRFTISR DDSKNTIYLQMSSLKAEDSAVYYCATNDVVRLRGVTP PILLWGQGTLITVSS |
| 8 | 6-8N VL amino acid sequence | QLVLTQSPSTSASLGAPVTLTCTLSSGHHSYPVAWHQ KHPEKGPRYLMKINGDGSHTKGDGIPDRFSGSSSGTGR YLTISSLQSEDEADYYCQTWATGWVFGGGTKLTVL |

TABLE 3

Amino Acid and Nucleotide Sequences of Antibody 2-20G

| SEQ ID NO | DESCRIPTION | SEQUENCE |
|---|---|---|
| 9 | 2-20G VH nucleotide sequence | GAGTTGCAGTTGGTGGAGTCTGGGGGAAAGTTGGT AAATCCGGGGGGGTCCCTGAGACTCTCATGTGCAG CCTCTGGATTCACTTTCCCTAACGCCTGGTTTAACT GGGTCCGCCAGACTCCAGGGAGGGGGCTGGAGTG GGTTGCCCGTATTAAAAGTCATTCTGACGGTGGGA CAGCCGACTACGCTGCACCCGTGAAAGGCAGATTC ACCGTCTCAAGGGATGATTCAGAGAACATGGTGTT TCTGCAAATGAACCGCCTGCGTGCCGAGGACACAG CCGTTTATTATTGTACTACCTTGGAGATTTATCACC CTGTGGACGTCTGGGGCCAGGGGACCACGGTCGCC GTCTCCTCA |
| 10 | 2-20G VL nucleotide sequence | GATGTTGTGCTGACTCAGTCTCCACTCTCCCTGTCC GTCACCCTTGGACAGCCGGCCTCCATCTCCTGCAG GTCCAGTCACAGCCTCCCAAGAGATGATGAATACT CCTACCTGAATTGGTTTCAGCAGAGGCCAGGCCAG TCTCCAAGGCGCCTAATTTATAGGGTTTCTAAGCG GGACTCTGGGGTCCCAGACAGATTCAGCGGCAGTG GGTCAGACACTTATTTCACACTGACAATCAGCAGG GTGGAGGCTGAGGATGTTGGAGTTTATTACTGCAT GCAAGGTACATACTGGCCCGGGACGTTCGGCCAAG GGACGAAGTTGGAAATCGAGCGA |
| 11 | 2-20G VH amino acid sequence | ELQLVESGGKLVNPGGSLRLSCAASGFTFPNAWFNW VRQTPGRGLEWVARIKSHSDGGTADYAAPVKGRFT VSRDDSENMVFLQMNRLRAEDTAVYYCTTLEIYHPV DVWGQGTTVAVSS |
| 12 | 2-20G VL amino acid sequence | DVVLTQSPLSLSVTLGQPASISCRSSHSLPRDDEYSYL NWFQQRPGQSPRRLIYRVSKRDSGVPDRFSGSGSDTY FTLTISRVEAEDVGVYYCMQGTYWPGTFGQGTKLEI ER |

TABLE 4

Amino Acid and Nucleotide Sequences of Antibody 3-17I

| SEQ ID NO | DESCRIPTION | SEQUENCE |
|---|---|---|
| 13 | 3-17i VH nucleotide sequence | GAGGTGCACCTGGTGGAGTCTGGGGGAGGCCTCGT AAACCCGGGGGGGTCCCTTAGACTCTCCTGTACAG CCTCTGGATTCACTTTCATCACCGCCTGGATGACCT GGGCCCGCCAGGCTCCAGGGAGGGGGCTGGAGTG GATTGGACTTATTAAAAGCGGAAATGATGGTGGGG CTATAGAGTACGCTGCACCCGTGAAAGGCAGATTC ACCATCTCAAGAGATGATTCAAGGAATATGATTTA TCTACAAATGAATAATGTCAAAGCCGAGGACGCA GCCGTCTACTATTGTGCCACAAACGATGTTGCTTTG GTTTGGGGAGTTACCCCCCCCTTGCTTCTCTGGGGC CAGGGGACCCGGGTCACCGTCTCTTCA |
| 14 | 3-17I VL nucleotide sequence | CAACTTGTGGTGACTCAATCGCCCTCTGCCTCTGCC TCCCTGGGAGGCTCGGTCAAGCTCACCTGCACTCT GAGCAGTGGGCACGGCAACTACCCCGTCGCATGGC ATCAGCTCCACCCAGCGAAGGGCCCTCGATACTTG ATGAAGCTTAATGCAGATGGCAGCCACATCAAGG GGGCCGGGATCACTGATCGCTTCTCAGGCTTCAGG TCTGGGGCTGAGCGCTACCTCACCATCTCCAGCCT CCAGTCTGAAGATGAGGCTGATTATTACTGTCAGA CCTGGGCCCCTGGATGGGTGCTCGGCGGAGGGACC AAGCTGACCGTCCTA |
| 15 | 3-17I VH amino acid sequence | EVHLVESGGGLVNPGGSLRLSCTASGFTFITAWMTW ARQAPGRGLEWIGLIKSGNDGGAIEYAAPVKGRFTIS RDDSRNMIYLQMNNVKAEDAAVYYCATNDVALVW GVTPPLLLWGQGTRVTSS |
| 16 | 3-17I VL amino acid sequence | QLVVTQSPSASASLGGSVKLTCTLSSGHGNYPVAWH QLHPAKGPRYLMKLNADGSHIKGAGITDRFSGFRSG AERYLTISSLQSEDEADYYCQTWAPGWVLGGGTKLT VL |

TABLE 5

Amino Acid and Nucleotide Sequences of Antibody B-21J

| SEQ ID NO | DESCRIPTION | SEQUENCE |
|---|---|---|
| 17 | B-21J VH nucleotide sequence | CAGGTGCAACTGGTGGAGTGGGGGGGAGGCGTGG CCCAGCCTGGGACGTCCCTGAGGCTCACCTGTGAT GCGTCTGGATTCAGCTTCAGACATTATGGCATGCA CTGGGTCCGCCAGGCTCCAGGCAAGGGGCTGGAGT GGGTGGCAGTTATCTGGCATAATGGAAGAGACAG AGAGTATGCAGACTCCGTGAAGGGCCGCTTCACCA TCTCCAGAGACAATTCCAAGTACACCCTGTCTTTA CAAATGAACAGCCTGACAGTCGAAGACACGGCAT TATATTACTGCGGGAGAGATCGAGGTGAAGACGA GCCGATTGACTTTTGGGGCCAGGGAACCCTGGTCA CCGTCTCTTCA |
| 18 | B-21J VL nucleotide sequence | CAGGCTGTGCTGACTCAACCGTCTTCCCTCTCTGCA TCTCCTGGAGCATCAGCCAGTCTCACCTGCACCTT GCGCAGTGGCCTCAGTGCTGGTCCCAAGTGGATAT ACTGGTACCAGCAGAGGGCAGGGAGTCCTCCCCA ATTTCTCCTGACATACAAATCAGACTCAGAAGAGC GGCGGAGCTCTGGACTCCCCAGCCGCTTCTCTGGA TCCAAGGATGGCTCGGCCAATGCAGGGATTTTACT CATCTCTGGGCTCCAATCTGAAGATGAGGCAGACT ATTACTGTGCGATTTGGCACAGCAACGTTGTCTTTT TCGGCGCAGGGACCAGGTTGACCGTCCTG |
| 19 | B-21J VH amino acid sequence | QVQLVEWGGGVAQPGTSLRLTCDASGFSFRHYGMH WVRQAPGKGLEWVAVIWHNGRDREYADSVKGRFTI SRDNSKYTLSLQMNSLTVEDTALYYCGRDRGEDEPI DFWGQGTLVTVSS |

TABLE 5-continued

Amino Acid and Nucleotide Sequences of Antibody B-21J

| SEQ ID NO | DESCRIPTION | SEQUENCE |
|---|---|---|
| 20 | B-21J VL amino acid sequence | QAVLTQPSSLSASPGASASLTCTLRSGLSAGPKWIYW YQQRAGSPPQFLLTYKSDSEERRSSGLPSRFSGSKDG SANAGILLISGLQSEDEADYYCAIWHSNVVFFGAGTR LTVL |

TABLE 6

Amino Acid and Nucleotide Sequences of Antibody F-18D

| SEQ ID NO | DESCRIPTION | SEQUENCE |
|---|---|---|
| 21 | F-18D VH nucleotide sequence | GAGGTGCGCCTGGTGGAGTCTGGGGGAGGCTTAAT AGAGCCGGGGGGTCTCTTAGACTCTCATGTGAAG CCTCTGGATTCGTTTTCACTACCGCCTGGATGAATT GGGTCCGCCAGGCTCCAGGGAAGGGGCTGGAGTG GGTTGGCCGTATTAAGAGCAAAAATGAGGCTGAG ACAACAGACTACGCTGCACCCGTGAAAGGCAGATT CACCATCTCAAGAGATGATTCAAAGGACACATTGT ATCTGCAAATGAACAACCTGAAAACCGAAGACAC AGCCGTCTATTATTGTACCACACTTGAGACGTATT ACGAGTCCGACTTCTGGGGCCAGGGAGTCCTGGTC GCCGTCTCCTCA |
| 22 | F-18D VL nucleotide sequence | GATGTTGTGATGACTCAGTCTCCACTCTCCCTGACC GTCACTCTTGGACAGCCGGCCTCCATCTCCTGCAG GTCTAGTCAAAGCCTCGCAGAGAGAGAAGAGGAC ATCTTGTTAAACTGGTATCACCAGGGGCCAGGCCA ATCTCCCAGGCGCCTAATTTATAGAGTTTCTAAGC GTGAGTCTGGGGTCCCAAATAAATTCAGCGGCAGT GTGTCAGGCACTGATTTCACCCTGAGAATCAGCAG GGTGGAGGCTGAGGATGTTGGGGTTTATTACTGCA TGCAACGAACACACTGGCCTCAGACTTTTGGCCAG GGGACCAAGCTGGAGATCAGACGA |
| 23 | F-18D VH amino acid sequence | EVRLVESGGGLIEPGGSLRLSCEASGFVFTTAWMNW VRQAPGKGLEWVGRIKSKNEAETTDYAAPVKGRFTI SRDDSKDTLYLQMNNLKTEDTAVYYCTTLETYYESD FWGQGVLVAVSS |
| 24 | F-18D VL amino acid sequence | DVVMTQSPLSLTVTLGQPASISCRSSQSLAEREEDILL NWYHQGPGQSPRRLIYRVSKRESGVPNKFSGSVSGT DFTLRISRVEAEDVGVYYCMQRTHWPQTFGQGTKLE IRR |

TABLE 7

Amino Acid and Nucleotide Sequences of Antibody J-5N

| SEQ ID NO | DESCRIPTION | SEQUENCE |
|---|---|---|
| 25 | J-5N VH nucleotide sequence | CAGGTGCAGCTGGTGGAGTGGGGGGGAGGCGTGG TCCAGCCTGGGGGGTCCCTGAGACTTTGCTGTGCA GCGTCTGGATTCAGTTTAAGGAGTTTTGGCATGCA CTGGGTCCGTCAGGCTCCAGGCAAGGGGCTGGAAT GGGTGGCAGTTATTTGGCCCCGACGAAGTCAAATA CAATATGCAGACTCCGTGAAGGGCCGAGTCACCAT CTCCAGAGACGACTCTAGGAGTACGGTATGTCTGC AGATGAACAGCCTGAGAGTCGAGGACACGGCTCT CTATCGCTGTGCGAGAGACCCCGGTGAGGACAATC CCATAGATTACTGGGGCCAGGGAACCCTGGTCATC GTCTCCTCA |
| 26 | J-5N VL nucleotide sequence | CAGGCTGTGCTGACTCAGCCGTCTTCCCTCTCTGCA TCTCCTGGAGCATCAGCCAGTCTCACCTGCACCTTC CTCAGCGGCATCAATGTTGGTCCCTACTGGATATA CTGGTACCAGCAAAAGCCAGGGAGTCCTCCCCAGT TTCTCCTGAGGTACAAGTCAGACTCAGATAAGCAC |

TABLE 7-continued

Amino Acid and Nucleotide Sequences of Antibody J-5N

| SEQ ID NO | DESCRIPTION | SEQUENCE |
|---|---|---|
|  |  | CAGGGCTCTGAAGTCCCCAGCCGCTTCTCTGGATC CAAAGATGCTTCGGCCAATGCAGGGATTTTACTCA TCTCTGGGCTCCAGTCTGAAGATGAGGCTGACTAT TACTGTATGATCTGGCACGTCAGCGGTGTGATTTTC GGCGGAGGGACCAAGCTGACCGTCCTA |
| 27 | J-5N VH amino acid sequence | QVQLVEWGGGVVQPGGSLRLCCAASGFSLRSFGMH WVRQAPGKGLEWVAVIWPRRSQIQYADSVKGRVTIS RDDSRSTVCLQMNSLRVEDTALYRCARDPGEDNPID YWGQGTLVIVSS |
| 28 | J-5N VL amino acid sequence | QAVLTQPSSLSASPGASASLTCTFLSGINVGPYWIYW YQQKPGSPPQFLLRYKSDSDKHQGSEVPSRFSGSKDA SANAGILLISGLQSEDEADYYCMIWHVSGVIFGGGTK LTVL |

TABLE 8

Amino Acid and Nucleotide Sequences of Antibody J-8G

| SEQ ID NO | DESCRIPTION | SEQUENCE |
|---|---|---|
| 29 | J-8G VH nucleotide sequence | CAGGTGCAACTGGTGGAGTGGGGGGGAGGCGTGG TCCAGCCTGGGACGTCCCTGAGACTCACCTGTGAT GCGTCTGGATTCAGCTTCAGACATTATGGCATGCA CTGGGTCCGCCAGGCTCCAGGCAAGGGGCTGGAGT GGGTGGCAGTTATCTGGCATAATGGAAGAGATAA AGACTATGCAGACTCCGTGAAGGGCCGGTTCACCA TCTCCAGAGACAATTCCAAGTACACCCTGTCTTTA CAAATGAACAGCCTGACAGTCGAGGACACGGCAT TATATTACTGTGGGAGAGATCGAGGTGAAGACGA GCCGATTGACTTTTGGGGCCAGGGAACCCTGGTCA CCGTCTCCTCA |
| 30 | J-8G VL nucleotide sequence | CAGGCTGTGCTGACTCAACCGTCTTCCCTCTCTGCA TCTCCTGGAGCATCAGCCAGTCTCACCTGCACCTT GCGCAGTGGCCTCAATGTTGGTCCCTACTGGATAT ACTGGTACCAGCAGAAGGCAGGGAGTCCTCCCCA ATTTCTCCTGAGATACAAATCAGACTCAGAAAAGC GGCGGAGCTCTGGAGTCCCCAGCCGCTTCTCTGGA TCCAAAGATGCCTCGGCCAATGCAGGGATTTTACT CATCTCTGGGCTCCAGTCTGAAGATGAGGCTGACT ATTATTGTGCGATTTGGCACAGCAATGCTGTCTTTT TCGGCGCAGGGACCAAGTTGACCGTCCTA |
| 31 | J-8G VH amino acid sequence | QVQLVEWGGGVVQPGTSLRLTCDASGFSFRHYGMH WVRQAPGKGLEWVAVIWHNGRDKDYADSVKGRFTI SRDNSKYTLSLQMNSLTVEDTALYYCGRDRGEDEPI DFWGQGTLVTVSS |
| 32 | J-8G VL amino acid sequence | QAVLTQPSSLSASPGASASLTCTLRSGLNVGPYWIYW YQQKAGSPPQFLLRYKSDSEKRRSSGVPSRFSGSKDA SANAGILLISGLQSEDEADYYCAIWHSNAVFFGAGTK LTVL |

TABLE 9

Amino Acid and Nucleotide Sequences of Antibody 4-220

| SEQ ID NO | DESCRIPTION | SEQUENCE |
|---|---|---|
| 33 | 4-220 VH nucleotide sequence | CAGGTGCAGATGGTGGAGTTTGGGGGAGGCATCTT CCAGCCTGGGGGGTCCCTGAGACTCTCCTGTGTCG CGTCTGGATTCCCCTTCAGGTACTATGGTTTCCACT GGGTCCGCCAGACTCCAGGCAAGGGGCTGGAGTG GCTGGCAGTTGTATGGCACAATGGAAGGGAGACA TATTATGAAGACTCCGTGAAGGGCCGATTCACCAT CTCCAGAGACAATTACAAGAACACGCTGTATTTGC |

TABLE 9-continued

Amino Acid and Nucleotide Sequences of Antibody 4-220

| SEQ ID NO | DESCRIPTION | SEQUENCE |
|---|---|---|
|  |  | AAATGGACAGCCTGAGAGTCGAGGACACGGCTGT CTATCACTGTGCGAGAGATCGTGGTAGCGACGAAC CAATTGACTACTGGGGCCAGGGAGTTTTGGTCACC GTCTCCTCA |
| 34 | 4-220 VL nucleotide sequence | CAGGCTGTGCTGACTCAGCCGTCCTCCCTCTCTGCA TCTCCTGGAGCATCAGCCAGTATCACCTGCACCTT ACGCAGTGACCTCACTGTTGGTCCCTACTGGATGT ACTGGTACCAACAGAAGCCAGGGAGTCCTCCCCAA TTTCTCCTGAGGTACAAGTCAGACTCCGAAAAGTA TCAGGGCTCTGGAGTCCCCAGCCGCTTCTCTGGAT CCAAAGACGCTTCGGCCAATGCAGGGACTTTGCTC ATCTCTGGACTCCAGTCTGAAGATGAGGCTGACTA TTACTGTCAGACTTGGCACGCCAACACTGTGGTAT TTGGCGGAGGGACCAAGCTGACCGTCCTA |
| 35 | 4-220 VH amino acid sequence | QVQMVEFGGGIFQPGGSLRLSCVASGFPFRYYGFHW VRQTPGKGLEWLAVVWHNGRETYYEDSVKGRFTIS RDNYKNTLYLQMDSLRVEDTAVYHCARDRGSDEPI DYWGQGVLVTVSS |
| 36 | 4-220 VL amino acid sequence | QAVLTQPSSLSASPGASASITCTLRSDLTVGPYWMY WYQQKPGSPPQFLLRYKSDSEKYQGSGVPSRFSGSK DASANAGTLLISGLQSEDEADYYCQTWHANTVVFG GGTKLTVL |

TABLE 10

Amino Acid and Nucleotide Sequences of Antibody 6-20C

| SEQ ID NO | DESCRIPTION | SEQUENCE |
|---|---|---|
| 37 | 6-20C VH nucleotide sequence | CAGGTGCAGCTGGTGGAGTCTGGGGGAGGCGTCTT CCAGCCGGGGGGGTCCCTGAGACTCTCCTGTGCAG CGTCTGGATTCAGTTTCAGGAGATTTGGTATGCATT GGGTCCGCCAGGCTCCAGGCAAGGGGCTGGAGTG GCTGGCAGTTGTTTGGCATGATGGAAGGGAGACAC ACTATGGAGACTCCGTGAGGGGCCGATTCACCATC TCCAGAGACAACTCCATGCACATGGTGTTTTTGGA CATGTACAGCCTGAGGGTCGAGGACACGGCTCTAT ATCGCTGTGCGAGAGATCCTGGTCAGGACGAAGCC ATTGACTATTGGGGCCAGGGAGTCCTGGTCACCGT CTCGTCA |
| 38 | 6-20C VL nucleotide sequence | CAGGCTGTGCTGACTCAGCCGTCTTCCCTCTCTGCA TCTCCTGGAGCATCAGCCAGTCTCACCTGCACCTT ACACAGTGGCCTCACTGTTGGTCCCTATTGGATAT ACTGGTTCCGGCAGAAGCCAGGGAGTCCCCCCCAG TTTCTCCTCAGGTACAAATCCGACTCAGAGGAGTA CCGTGCCTCTGGAGTCCCCAGCCGCTTCTCTGGATC CAAAGATGCTTCGGCCAACTCAGGCATTTACTCA TCTCTGGACCACAGTCTGAAGACGAGGCTGACTAT TACTGTATGACTTGGCACACCAACAAGGTAGTCTT CGGCGGAGGGACCACACTGACCGTCCTA |
| 39 | 6-20C VH amino acid sequence | QVQLVESGGGVFQPGGSLRLSCAASGFSFRRFGMHW VRQAPGKGLEWLAVVWHDGRETHYGDSVRGRFTIS RDNSMHMVFLDMYSLRVEDTALYRCARDPGQDEAI DYWGQGVLVTVSS |
| 40 | 6-20C VL amino acid sequence | QAVLTQPSSLSASPGASASLTCTLHSGLTVGPYWIYW FRQKPGSPPQFLLRYKSDSEEYRASGVPSRFSGSKDA SANSGILLISGPQSEDEADYYCMTWHTNKVVFGGGT TLTVL |

TABLE 11

Amino Acid and Nucleotide Sequences of Antibody 12-14G

| SEQ ID NO | DESCRIPTION | SEQUENCE |
|---|---|---|
| 41 | 12-14G VH nucleotide sequence | CAGGTGCAGCTGGTGCAGTCTGGGGCTGAGGTGAA GAAGCCTGGGGCCTCAGTGAAGGTCTCCTGCCAGG CTTCTGGATACACCTTCACCAACTATGGTGTCAACT GGGTGCGACAGGCCACTGGACAAGGGCTTGAGTG GATGGGATGGATGAACACTAACAGTGGTGACACG GGTTATGCCCAGAAGTTCCAGGGCAGAGTCACCAT GACCAGGGACACCTCCATAAACACAGCCTACATGG AGCTGAGCGGACTGACATCTGAGGACACGGCCGTC TATTACTGTGCGCGAGCGTATTTTTTTGATTCGTGG AATAAGGGCAACTGGTTCGACCCCTGGGGCCAGG GAACCCCGGTCACCGTCTCCTCA |
| 42 | 12-14G VL nucleotide sequence | CAGTCTGTGCTGACTCAGGCACCCTCAGTGTCTGG GACCCCCGGGCAGAGGGTCACCATCTCTTGTTCTG GAGGCAGCTCCAACCTGGGAAGAAGTTATATATAT TGGTACCAACAGTTCCCAGGAACGGCCCCCAGAGT CCTCATTTATAAAAATAGTCAGCGGCCCTCAGGGG TCCCTGACCGATTCTCCGGCTCCAAGTCTGGCACCT CAGCCTCCCTGGCCATCAGTGGGCTCCGGTCCGAG GATGAGGCTCATTATTACTGTGCAGCATGGGATGA CAGCCTGAGTGGGTCTTGGGTGTTCGGCGGAGGGA CCAAGCTGACCGTCCTA |
| 43 | 12-14G VH amino acid sequence | QVQLVQSGAEVKKPGASVKVSCQASGYTFTNYGVN WVRQATGQGLEWMGWMNTNSGDTGYAQKFQGRV TMTRDTSINTAYMELSGLTSEDTAVYYCARAYFFDS WNKGNWFDPWGQGTPVTVSS |
| 44 | 12-14G VL amino acid sequence | QSVLTQAPSVSGTPGQRVTISCSGGSSNLGRSYIYWY QQFPGTAPRVLIYKNSQRPSGVPDRFSGSKSGTSASL AISGLRSEDEAHYYCAAWDDSLSGSWVFGGGTKLTV L |

TABLE 12

Amino Acid and Nucleotide Sequences of Antibody 15-6J

| SEQ ID NO | DESCRIPTION | SEQUENCE |
|---|---|---|
| 45 | 15-6J VH nucleotide sequence | CAGGTGCAGTTGGTGGAGTTTGGGGGAGGCATTTT CGAGCCTGGGGGGTCCCTGAGACTCTCCTGTGTCG CGTCTGGATTCTCCTTCAGGCATTATGGTATGCACT GGGTCCGCCAGGCTCCAGGCAAGGGGCTGGAGTG GCTGGCAGTTGTATGGCATGATGGAAGGGAGACA CATTATGGAGACTCCGTGAAGGGGCGATTCACCAT CTCCAGAGACAATTACAAGAATACGCTGTTTTTGC AAATGGACAGCCTGAGAGTCGAGGACACGGCTGT CTATCACTGTGCGAGAGATCGTGGTAGCGACGAAC CTATTGACTACTGGGGCCAGGGAGTTTTGGTCACC GTCTCCTCA |
| 46 | 15-6J VL nucleotide sequence | CAGGCTGTGCTGACTCAGCCGTCCTCCCTCTCTGCA TCTCCTGGAGCATCAGCCAGTATCACCTGCACCTT ACGCAGTGACGTCACTGTTAGTCCCTGGACATACT GGTACCAACAGAAGCCAGGGAGTCCTCCCCGATTT CTCCTGAGATACAAATCAGACTCTGATAAGTATCA GGGCTCTGGAGTCCCCAGCCGCTTCTCTGGATCCA AAAATGCTTCGGCCAATGCAGCGATTTTACTCATC TCTGGGCTCCAGTCTGAAGATGAGGCTGACTATTA CTGTCAGACTTGGCACACCACCACTGTGGTATTTG GCGGAGGGACCAAGCTGACCGTCCTA |
| 47 | 15-6J VH amino acid sequence | QVQLVEFGGGIFEPGGSLRLSCVASGFSFRHYGMHW VRQAPGKGLEWLAVVWHDGRETHYGDSVKGRFTIS RDNYKNTLFLQMDSLRVEDTAVYHCARDRGSDEPID YWGQGVLVTVSS |

TABLE 12-continued

Amino Acid and Nucleotide Sequences of Antibody 15-6J

| SEQ ID NO | DESCRIPTION | SEQUENCE |
|---|---|---|
| 48 | 15-6J VL amino acid sequence | QAVLTQPSSLSASPGASASITCTLRSDVTVSPWTYWY QQKPGSPPRFLLRYKSDSDKYQGSGVPSRFSGSKNAS ANAAILLISGLQSEDEADYYCQTWHTTTVVFGGGTK LTVL |

TABLE 13

Amino Acid and Nucleotide Sequences of Antibody 18-11C

| SEQ ID NO | DESCRIPTION | SEQUENCE |
|---|---|---|
| 49 | 18-11C VH nucleotide sequence | CAGGTGCAGCTGGTGCAGTCTGGGGCTGAGATTAA GAGGCCTGGGGCCTCAGTGAAGGTCTCCTGCAAGG CGTCTGGATACACTTTCACCAGCTTTGGTATCAACT GGGTGCGACAGGCCCCTGGACAAGGGCTTGAGTG GATGGGATGGATGAACTCCAACAGTGGTGATGCG GACTCTGCACAGAAGTTCCAGGGCAGACTCACTAT GACCACCGACACCTCCACAAGTACAGCCTACATGG AGCTGAGGAATCTGAGATCTGAGGACACGGCCGT ATATTATTGCGCGAGAATGAATTTCCGTGGTTCGA AGTGGGAGGTGAACTGGTTCGACCCCTGGGGCCAG GGAACCCTGATCACCGTCTCCTCA |
| 50 | 18-11C VL nucleotide sequence | CAGTCTGTGGTGACTCAGCCACCCTCAGCGTCTGG GACCCCCGGGCAGAGGGTCACCATCTCCTGTTCTG GAAGCAGGTCCAACGTCGAAAGAAATTTTGTTTAC TGGTACCAGCAACTCCCAGGAACGGCCCCCAAACT TCTCATCTATATGAACAGTCAGCGGCCCTCAGGGG TCCCTGACCGATTCTCTGGCTCTCGTTCTGGCACCT CAGCCTCCCTGGCCATCACTGGGCTTCGGTCCGAG GATGAGGCTGACTATTATTGTGCAACTTGGGATGA CAATCTGAGAGGCTGGGTGTTCGGCGGAGGGACC AAGGTGACCGTCCTA |
| 51 | 18-11C VH amino acid sequence | QVQLVQSGAEIKRPGASVKVSCKASGYTFTSFGINW VRQAPGQGLEWMGWMNSNSGDADSAQKFQGRLTM TTDTSTSTAYMELRNLRSEDTAVYYCARMNFRGSK WEVNWFDPWGQGTLITVSS |
| 52 | 18-11C VL amino acid sequence | QSVVTQPPSASGTPGQRVTISCSGSRSNVERNFVYWY QQLPGTAPKLLIYMNSQRPSGVPDRFSGSRSGTSASL AITGLRSEDEADYYCATWDDNLRGWVFGGGTKVTV L |

TABLE 14

Amino Acid and Nucleotide Sequences of Antibody 20-2D

| SEQ ID NO | DESCRIPTION | SEQUENCE |
|---|---|---|
| 53 | 20-2D VH nucleotide sequence | CAGGTGCAGCTGGTGCAGTCTGGGGCTGAGATTAA GAGGCCTGGGGCCTCAGTGAAGGTCTCCTGCAAGG CGTCTGGATACACCTTCACCAGGTTCGGCATCAAC TGGGTGCGACAGGCCCCTGGACAAGGGCTTGAGTG GATGGGATGGATGAACTCCAACAGTGGTAATGCG GACTCTGCACAGAAGTTCCAGGGCAGACTCACTAT GACCACCGACACCTCCACAAGTACAGCCTACATGG AGCTGAGGAATCTAAGATCTGAGGACACGGCCGT ATATTATTGCGCGAGAATGAATTACCGTGGTTCGA AGTGGGAAATAAACTGGTTCGACCCCTGGGGCCAG GGAACCCTGATCACCGTCTCCTCA |
| 54 | 20-2D VL nucleotide sequence | CAGTCTGTGGTGACTCAGCCACCCTCAGCGTCTGG GACCCCCGGGCAGAGGGTCACCATTTCCTGTTCTG GTAGCAGGTCCAACGTCCAAAGAAATTTTGTTTAC TGGTACCAGCAGCTCCCAGGAACGGCCCCCAAACT TCTCATCTATATGAACAATAACCGCCCCTCAGGGG |

TABLE 14-continued

Amino Acid and Nucleotide Sequences of Antibody 20-2D

| SEQ ID NO | DESCRIPTION | SEQUENCE |
|---|---|---|
| | | TCCCTGACCGATTCTCTGGCTCTCATTCTGGCACCT CAGCCTCCCTGGCCATCACTGGGCTTCGGTCCGAG GATGAGGCTGATTATTATTGTGCTACTTGGGATGA CAATCTGAGAGGCTGGGTGTTCGGCGGAGGGACC AAGGTGACCGTCCTA |
| 55 | 20-2D VH amino acid sequence | QVQLVQSGAEIKRPGASVKVSCKASGYTFTRFGINW VRQAPGQGLEWMGWMNSNSGNADSAQKFQGRLTM TTDTSTSTAYMELRNLRSEDTAVYYCARMNYRGSK WEINWFDPWGQGTLITVSS |
| 56 | 20-2D VL amino acid sequence | QSVVTQPPSASGTPGQRVTISCSGSRSNVQRNFVYWY QQLPGTAPKLLIYMNNNRPSGVPDRFSGSHSGTSASL AITGLRSEDEADYYCATWDDNLRGWVFGGGTKVTV L |

TABLE 15

Amino Acid and Nucleotide Sequences of Antibody 9-5L

| SEQ ID NO | DESCRIPTION | SEQUENCE |
|---|---|---|
| 57 | 9-5L VH nucleotide sequence | CAGGTGCACCTGGTGGAGTCTGGGGGAGACCTGGT CCAGCCTGGGAGGTCCCTGAGACTCTCCTGTGCAG CGTCTGGATTTACCCTCAAACGTTATGGCATTCACT GGGTCCGCCAGGCGCCAGGCAAGGGGCTGGAGTG GGTGGCAGTTACTTGGCATGATGGAAATATATACT ATGCAGACTCCGTGAAGGGCCGACTCACCGTCTCC AGAGACAGTTACAAGAACACGGTGGATCTACAAA TGAACAGCCTGAAAGTCGAGGACACGGCTCTATAT TACTGTGCGAGAGATGCCGGGCAAAATGCGCCCAT TGACCTCTGGGGCCACGGAACCCTGGTCACCGTCT CCTCA |
| 58 | 9-5L VL nucleotide sequence | CAGGCTGTACTGACTCAGCCGTCTTCCCTCTCTGCA TCTCCTGGAGCATCAGCCAGTCTCACCTGCACCTT ACCCAGTGGCATCAATGTTGCTACCCACTGGATAT ACTGGTACCAGCAGAAGCCTGGCAGTCCTCCCCAG TTTCTCCTGCGGTACAAATCAGACTCAGATATCCA ACACGGCTCTGGAGTCCCCAGCCGCTTCTCTGGAT CCAAAGATGCTTCGGCCAATGCCGCGATTTTAGTC GTCTCTGGTCTCCAGTCTGAGGATGAGGCTGACTA TTACTGTATGATTTGGTATTCCACCGCCGTGGTTTT CGGCGGAGGGACCAAGCTGACCGTCCTG |
| 59 | 9-5L VH amino acid sequence | QVHLVESGGDLVQPGRSLRLSCAASGFTLKRYGIHW VRQAPGKGLEWVAVTWHDGNIYYADSVKGRLTVSR DSYKNTVDLQMNSLKVEDTALYYCARDAGQNAPID LWGHGTLVTVSS |
| 60 | 9-5L VL amino acid sequence | QAVLTQPSSLSASPGASASLTCTLPSGINVATHWIYW YQQKPGSPPQFLLRYKSDSDIQHGSGVPSRFSGSKDA SANAAILVVSGLQSEDEADYYCMIWYSTAVVFGGGT KLTVL |

TABLE 16

Amino Acid and Nucleotide Sequences of Antibody 15-20G

| SEQ ID NO | DESCRIPTION | SEQUENCE |
|---|---|---|
| 61 | 15-20G VH nucleotide sequence | CAGGTGCAGTTGGTGGAGTTTGGGGGAGGCATTTT CCAGCCTGGGGGGTCCCTGAGACTCTCCTGTGTCG CGTCTGGATTCTCCTTCAGGTATTATGGTTTCCACT GGGTCCGCCAGGCTCCAGGCAAGGGGCTGGAGTG GCTGGCAGTTGTATGGCATGATGGAAGGGAGACA CATTATGGAGACTCCGTGAGGGGCGATTCACCAT CTCCAGAGACAATTACAAGAACACGGTGTTTTTGG |

TABLE 16-continued

Amino Acid and Nucleotide Sequences of Antibody 15-20G

| SEQ ID NO | DESCRIPTION | SEQUENCE |
|---|---|---|
| | | AAATGGACAGCCTGAGAGTCGAGGACACGGCTGT CTATCACTGTGCGAGAGATCGTGGTAGCGACGAAC CTATTGACTACTGGGGCCAGGGAGTTTTGGTCACC GTCTCCTCA |
| 62 | 15-20G VL nucleotide sequence | CAGGCTGTGCTGACTCAGCCGTCCTCCCTCTCTGCA TCTCCTGGAGCATCAGCCAGTATCACCTGCACCTT ACGCAGTGACCTCACTGTTAGTCCCTGGATATACT GGTACCAACAGAAGCCAGGGAGTCCTCCCCGATTT CTCCTGAAATACAAATCAGACTCCAATAACTACCA CGGCTCTGGAGTCCCCAGCCGCTTCTCTGGATCCA AAGATGCTTCGGCCAATGCAGCGATTTTACTCATC TCTGGACTCCAGTCTGAAGATGAGGCTGACTATTA CTGTCAGACTTGGCACACCACCACTGTGGTATTTG GCGGAGGGACCAAGCTGACCGTCCTA |
| 63 | 15-20G VH amino acid sequence | QVQLVEFGGGIFQPGGSLRLSCVASGFSFRYYGFHW VRQAPGKGLEWLAVVWHDGRETHYGDSVRGRFTIS RDNYKNTVFLEMDSLRVEDTAVYHCARDRGSDEPID YWGQGVLVTVSS |
| 64 | 15-20G VL amino acid sequence | QAVLTQPSSLSASPGASASITCTLRSDLTVSPWIYWY QQKPGSPPRFLLKYKSDSNNYHGSGVPSRFSGSKDAS ANAAILLISGLQSEDEADYYCQTWHTTTVVFGGGTK LTVL |

TABLE 17

Amino Acid and Nucleotide Sequences of Antibody 23-120

| SEQ ID NO | DESCRIPTION | SEQUENCE |
|---|---|---|
| 65 | 23-120 VH nucleotide sequence | CAGGTGCAGTTGGTGGAGTTTGGGGGAGGCATTTT CGAGCCTGGGGGGTCCCTGAGACTCTCCTGTGTCG CGTCTGGATTCTCCTTCAGGCATTATGGTATGCACT GGGTCCGCCAGGCTCCAGGCAAGGGGCTGGAGTG GCTGGCAGTTGTATGGCATGATGGAAGGGAGACA CATTATGGAGACTCCGTGAAGGGGCGATTCACCAT CTCCAGAGACAATTACAAGAATACGCTGTTTTTGC AAATGGACAGCCTGAGAGTCGAGGACACGGCTGT CTATCACTGTGCGAGAGATCGTGGTAGCGACGAAC CTATTGACTACTGGGGCCAGGGAGTTTTGGTCACC GTCTCCTCA |
| 66 | 23-120 VL nucleotide sequence | CAGGCTGTGCTGACTCAGCCGTCCTCCCTCTCTGCA TCTCCTGGAGCATCAGCCAGTATCACCTGCACCTT ACGCAGTGACGTCACTGTTAGTCCCTGGACATACT GGTACCAACAGAAGCCAGGGAGTCCTCCCCAATTT CTCCTGAGATACAAATCAGACTCTGATAAGTATCA GGGCTCTGGAGTCCCCAGCCGCTTCTCTGGATCCA AAAATGCTTCGGCCAATGCAGCGATTTTACTCATC TCTGGGCTCCAGTCTGAAGATGAGGCTGACTATTA CTGTCAGACTTGGCACACCAACAATGTGGTATTTG GCGGAGGGACCAAGCTGACCGTCCTA |
| 67 | 23-120 VH amino acid sequence | QVQLVEFGGGIFEPGGSLRLSCVASGFSFRHYGMHW VRQAPGKGLEWLAVVWHDGRETHYGDSVKGRFTIS RDNYKNTLFLQMDSLRVEDTAVYHCARDRGSDEPID YWGQGVLVTVSS |
| 68 | 23-120 VL amino acid sequence | QAVLTQPSSLSASPGASASITCTLRSDVTVSPWTYWY QQKPGSPPQFLLRYKSDSDKYQGSGVPSRFSGSKNAS ANAAILLISGLQSEDEADYYCQTWHTNNVVFGGGTK LTVL |

TABLE 18

Amino Acid and Nucleotide Sequences of Antibody 31-2C

| SEQ ID NO | DESCRIPTION | SEQUENCE |
|---|---|---|
| 69 | 31-2C VH nucleotide sequence | CAGGTGCAGTTGGTGGAGTTTGGGGGAGGCATTTT CCAGCCTGGGGGGTCCCTGAGACTCTCCTGTGTCG CGTCTGGATTCTCCTTCAGATATTATGGTTTCCACT GGGTCCGCCAGGCTCCAGGCAAGGGGCTGGAGTG GCTGGCAGTTGTATGGCATGATGGAAGGGAGACA CATTATGGAGACTCCGTGAAGGGGCGATTCACCAT CTCCAGAGACAATTACAAGAACACGCTGTTTTTGC AAATGGACAGCCTGAGAGTCGAGGACACGGCTGT CTATCACTGTGCGAGAGATCGTGGTAGCGACGAAC CTATTGACTACTGGGGCCAGGGAGTTTTGGTCACC GTCTCCTCA |
| 70 | 31-2C VL nucleotide sequence | CAGGCTGTGCTGACTCAGCCGTCCTCCCTCTCTGCA TCTCCTGGAGCATCAGCCAGTATCACCTGCACCTT ACGCAGTGGCCTCACTGTTAGTCCCTGGATATACT GGTACCAACAGAAGCCAGGGAGTCCTCCCCAATTT CTCCTGAGATACAAATCAGACTCCGAAAACTACCG GGGCTCTGGAGTCCCCAGTCGCTTCTCTGGATCCA AAGAGGCTTCGGCCAATGCAGCGATTTTATTCATC TCTGGACTCCAGTCTGAAGATGAGGCTGACTATTA CTGTCAGACTTGGCACACCAGCACAGTGGTATTTG GCGGAGGGACCAAGCTGACCGTCCTA |
| 71 | 31-2C VH amino acid sequence | QVQLVEFGGGIFQPGGSLRLSCVASGFSFRYYGFHW VRQAPGKGLEWLAVVWHDGRETHYGDSVKGRFTIS RDNYKNTLFLQMDSLRVEDTAVYHCARDRGSDEPID YWGQGVLVTVSS |
| 72 | 31-2C VL amino acid sequence | QAVLTQPSSLSASPGASASITCTLRSGLTVSPWIYWY QQKPGSPPQFLLRYKSDSENYRGSGVPSRFSGSKEAS ANAAILFISGLQSEDEADYYCQTWHTSTVVFGGGTK LTVL |

TABLE 19

Amino Acid and Nucleotide Sequences of Antibody 36-19H

| SEQ ID NO | DESCRIPTION | SEQUENCE |
|---|---|---|
| 73 | 36-19H VH nucleotide sequence | CAGGTGCAGCTGGTGCAGTCTGGGGCTGAGATTAA GAGGCCTGGGGCCTCAGTGAAGGTCTCCTGCAAGG CGTCTGGATACATTTTCACCAACTTTGGCATCAACT GGGTGCGACAGGCCCCTGGTCAAGGGCTTGAGTGG ATGGGATGGATGAACTCCAAGTATGGTAATGCGGA CTCTGCACATAAGTTCCAGGACAGACTCACTATGA CCACCGACACCTCCACAAGTACAGCCTACATGGAG CTGAGAAATCTGAGATCTGAGGACACGGCCGTATA TTATTGCGCGAGAATGAATTACCGTGATTCGAAGT GGGACGTGAATTGGTTCGACCCCTGGGGCCAGGGA ACCCTGATCACCGTCTCCTCA |
| 74 | 36-19H VL nucleotide sequence | CAGTCTGTGGTGACTCAGCCACCCTCAGCGTCTGG GACCCCCGGGCAGAGGGTCACCATCTCCTGTTCTG GAAGCAGGTCCAACGTCGAAAGAAATTTTGTTTAC TGGTACCAGCAGCTCCCAGGAACGGCCCCCAAACT TCTCATCTATATGAACAATCAGCGCCCCTCAGGGG TCCCTGACCGATTCTCTGGCTCTCGTTCTGGCACCT CAGCCTCCCTGGCCATCACTGGGCTTCGGTCCGAG GATGAGGCTGATTATTATTGTGCAGTTTGGGATGA CAATCTCAGAGGCTGGGTGTTCGGCGGAGGGACCG AGGTGACCGTCCTA |
| 75 | 36-19H VH amino acid sequence | QVQLVQSGAEIKRPGASVKVSCKASGYIFTNFGINWV RQAPGQGLEWMGWMNSKYGNADSAHKFQDRLTMT TDTSTSTAYMELRNLRSEDTAVYYCARMNYRDSKW DVNWFDPWGQGTLITVSS |

TABLE 19-continued

Amino Acid and Nucleotide Sequences of Antibody 36-19H

| SEQ ID NO | DESCRIPTION | SEQUENCE |
|---|---|---|
| 76 | 36-19H VL amino acid sequence | QSVVTQPPSASGTPGQRVTISCSGSRSNVERNFVYWY QQLPGTAPKLLIYMNNQRPSGVPDRFSGSRSGTSASL AITGLRSEDEADYYCAVWDDNLRGWVFGGGTEVTV L |

TABLE 20

Amino Acid and Nucleotide Sequences of Antibody 36-21L

| SEQ ID NO | DESCRIPTION | SEQUENCE |
|---|---|---|
| 77 | 36-21L VH nucleotide sequence | CAGGTGCAGCTGGTGCAGTCTGGGGCTGAGATTAA GAGGCCTGGGGCCTCAGTGAAGGTCTCCTGCAAGG CGTCTGGATACACTTTCACCGGCTTTGGTATCAACT GGGTGCGACAGGCCCCAGGACAGGGGCTTGAGTG GATGGGATGGATGAACTCCAACACTGGTGATGCGG ACTCTGCACAGAAGTTCCAGGGCAGACTCACTATG ACCACCGACACCTCCACAAGTACAGCCCACATGGA GCTGACGAATCTGGGATCTGAGGACACGGCCGTAT ACTATTGCGCGAGAATGAATTTCCTTGGTTCGAAG TGGGAGGTGAACTGGTTCGACCCCTGGGGCCAGGG AACCCTGATCACCGTCTCCTCA |
| 78 | 36-21L VL nucleotide sequence | GATGTTGTGCTGACTCAGTCTCCACTCTCCCTGTCC GTCACCCTTGGACAGCCGGCCTCCATCTCCTGCAG GTCCAGTCACAGCCTCCCAAGAGATGATGAATACT CCTACCTGAATTGGTTTCAGCAGAGGCCAGGCCAG TCTCCAAGGCGCCTAATTTATAGGGTTTCTAAGCG GGACTCTGGGGTCCCAGACAGATTCAGCGGCAGTG GGTCAGACACTTATTTCACACTGACAATCAGCAGG GTGGAGGCTGAGGATGTTGGAGTTTATTACTGCAT GCAAGGTACATACTGGCCCGGGACGTTCGGCCAAG GGACGAAGTTGGAAATCGAGCGA |
| 79 | 36-21L VH amino acid sequence | QVQLVQSGAEIKRPGASVKVSCKASGYTFTGFGINW VRQAPGQGLEWMGWMNSNTGDADSAQKFQGRLTM TTDTSTSTAHMELTNLGSEDTAVYYCARMNFLGSK WEVNWFDPWGQGTLITVSS |
| 80 | 36-21L VL amino acid sequence | DVVLTQSPLSLSVTLGQPASISCRSSHSLPRDDEYSYL NWFQQRPGQSPRRLIYRVSKRDSGVPDRFSGSGSDTY FTLTISRVEAEDVGVYYCMQGTYWPGTFGQGTKLEI ER |

TABLE 21

Amino Acid and Nucleotide Sequences of Antibody 41-180

| SEQ ID NO | DESCRIPTION | SEQUENCE |
|---|---|---|
| 81 | 41-180 VH nucleotide sequence | GAGGTACAGCTGGTGGAGTCTGGGGGAGGCCTGG TCCAGCCTGGGGGGTCTCTGAGACTCTCCTGTGCA GCCTCTGGATTCACCTTTAATCACGATTGGATGACT TGGGTCCGCCAGGCTCCAGGGAAGGGTCTGGAGTG GGTGGCCAACATAATACAAGATGGAAGCGAAACA TACTATGTGGACTCTGTGAAGGGCCGATTCACCAT CTCCAGAGACAATGCCAAGAATTTACTGTATCTGC AGATGAACAGCCTGAGAGTCGAGGACACGGCTGT GTATTTCTGTGGCCGGAGTATGGACGTCTGGGGCC AAGGGACCACGGTCATCGTCTCCTCA |
| 82 | 41-180 VL nucleotide sequence | CAGTCTGTGCTGACTCAGCCACCCTCAGCGTCTGG GACCCCCGGGCAGAGGGTCACCATCTCTTGTTCTG GAAGCAGCTCCAACATCGGAAGTAATACTGTGAAC TGGTACCACCAGGTCCCAGGAACGGCCCCCAAACT CCTCATCTATACTGATAATCAGCGGCCCTCAGGGG TCCCTGACCGATTCTCTGGCTCCAAGTCTGGCACCT |

TABLE 21-continued

Amino Acid and Nucleotide Sequences of Antibody 41-180

| SEQ ID NO | DESCRIPTION | SEQUENCE |
|---|---|---|
| | | CAGCCTCCCTGGCCATCAGTGGGCTCCAGTCTGAG<br>GATGAAGGTGATTATTACTGTGCAGCGAGGGATGG<br>CAGCCTGGATGTTTGGGTGTTCGGCGGAGGGACCA<br>AAGTGACTGTCCTA |
| 83 | 41-180 VH amino acid sequence | EVQLVESGGGLVQPGGSLRLSCAASGFTFNHDWMT<br>WVRQAPGKGLEWVANIIQDGSETYYVDSVKGRFTIS<br>RDNAKNLLYLQMNSLRVEDTAVYFCGRSMDVWGQ<br>GTTVIVSS |
| 84 | 41-180 VL amino acid sequence | QSVLTQPPSASGTPGQRVTISCSGSSSNIGSNTVNWY<br>HQVPGTAPKLLIYTDNQRPSGVPDRFSGSKSGTSASL<br>AISGLQSEDEGDYYCAARDGSLDVWVFGGGTKVTV<br>L |

TABLE 22

Amino Acid and Nucleotide Sequences of Antibody 5-14N

| SEQ ID NO | DESCRIPTION | SEQUENCE |
|---|---|---|
| 85 | 5-14N VH nucleotide sequence | CAGGTGCAGCTGGTGCAGTCTGGGGCTGAGATTAA<br>GAGGCCTGGGGCCTCAGTGAAGGTCTCCTGCAAGG<br>CGTCTGGATACACTTTCACCAACTTTGGAATCAAC<br>TGGGTGCGACAGGCCCCTGGACAAGGGCTTGAGTG<br>GATGGGATGGATGAACTCCAGAACTGGTGATGCG<br>GACTCTGCACAGAACTTCCAGGGCAGGCTCACTAT<br>GACCACCGACACCTCCAGAAGTATAGCCTACATGG<br>AGCTGACGCACCTGACCTCTGAGGACACGGCCGTA<br>TATTATTGCGCGAGAATGAATTTCCTTGGTTCGAG<br>GTGGGAGGTGAACTGGTTCGACCCCTGGGGCCAGG<br>GAACCCTGATCACCGTCTCCTCA |
| 86 | 5-14N VL nucleotide sequence | CAGTCTGTGGTGACTCAGCCACCCTCAGTGTCTGG<br>GACCCCCGGGCAGAGGGTCACCATCTCCTGTTCTG<br>GAAGCAGGTCCAACGTCGAAAGAAATTTTTTTTAC<br>TGGTATCAGCAATTCCCAGGAACGGCCCCCAAACT<br>TCTCATCTATATGAACAGTCAGCGGCCCGCAGGGG<br>TCCCTGACCGATTCTCTGGCTCTCGTTCTGGCACCT<br>CAGTTTCCCTGGCCATCACTGGGCTTCGGTCCGAG<br>GATGAGGCTGACTATTATTGTGCAACTTGGGATGA<br>CAATCTGAGAGGCTGGGTGTTCGGCGGAGGGACC<br>AAGGTGACCGTCCTA |
| 87 | 5-14N VH amino acid sequence | QVQLVQSGAEIKRPGASVKVSCKASGYTFTNFGINW<br>VRQAPGQGLEWMGWMNSRTGDADSAQNFQGRLTM<br>TTDTSRSIAYMELTHLTSEDTAVYYCARMNFLGSRW<br>EVNWFDPWGQGTLITVSS |
| 88 | 5-14N VL amino acid sequence | QSVVTQPPSVSGTPGQRVTISCSGSRSNVERNFFYWY<br>QQFPGTAPKLLIYMNSQRPAGVPDRFSGSRSGTSVSL<br>AITGLRSEDEADYYCATWDDNLRGWVFGGGTKVTV<br>L |

TABLE 23

Amino Acid and Nucleotide Sequences of Antibody 11-19C

| SEQ ID NO | DESCRIPTION | SEQUENCE |
|---|---|---|
| 89 | 11-19C VH nucleotide sequence | CAGGTGCAGCTGGTGCAGTCTGGGGCTGAGATTAA<br>GCGGCCTGGGGCCTCAGTGAAGATCTCCTGCAAGG<br>CGTCTGGATACATTTTCACCAGCTTTGGTATCAACT<br>GGGTGCGACAGGCCCCTGGACAAGGGCTTGAGTG<br>GATGGGATGGATGAACTCCAACACTGGTGATGCGG<br>ACTCTCTACAGAAGTTCCAGGGCAGACTCACCATG<br>ACCACCGACACCTCCACAAGCACAGCCTACATGGA<br>ATTGAGCAATCTGAGATCTGAAGACACGGCCGTAT |

TABLE 23-continued

Amino Acid and Nucleotide Sequences of Antibody 11-19C

| SEQ ID NO | DESCRIPTION | SEQUENCE |
| --- | --- | --- |
|  |  | ATTATTGCGCGAGAATGAATTTCCATGGTTCGAGG TGGGACGTGAACTGGTTCGACCCCTGGGGCCAGGG AACCCTGATCACCGTCTCCTCA |
| 90 | 11-19C VL nucleotide sequence | CAGTCTGTGGTGACTCAGCCACCCTCAGCGTCTGG GACCCCCGGGCAGAGGGTCATCATCTCCTGTTCTG GAAGCGGGTCCAACGTCGAAAGAAATTCTGTTTAC TGGTACCAACAGTTCCCGGGAACGGCCCCCAAACT TCTCATCTACATGAGCAATAGGCGCCCCTCAGGGG TCCCTGACCGATTCTTTGGCTCTCGTTCTGGCACCT CAGCCTCCCTGGCCATCACTGGGCTTCGGCCCGAG GATGAGGCTGATTATTATTGTGCAGTTTGGGATGA CAGTCTGAGAGGCTGGGTATTCGGCGGAGGGACC AAGGTGACCGTCCTA |
| 91 | 11-19C VH amino acid sequence | QVQLVQSGAEIKRPGASVKISCKASGYIFTSFGINWV RQAPGQGLEWMGWMNSNTGDADSLQKFQGRLTMT TDTSTSTAYMELSNLRSEDTAVYYCARMNFHGSRW DVNWFDPWGQGTLITVSS |
| 92 | 11-19C VL amino acid sequence | QSVVTQPPSASGTPGQRVIISCSGSGSNVERNSVYWY QQFPGTAPKLLIYMSNRRPSGVPDRFFGSRSGTSASL AITGLRPEDEADYYCAVWDDSLRGWVFGGGTKVTV L |

TABLE 24

Amino Acid and Nucleotide Sequences of Antibody F-8C

| SEQ ID NO | DESCRIPTION | SEQUENCE |
| --- | --- | --- |
| 93 | F-8C VH nucleotide sequence | CAGGTGCAGCTGGCGGAGTCTGGGGGAGGCGTGG TCCAGCCTGGGGGGTCCCTGAGACTTTCCTGTGCA GCGTCTGGATTCAGTCTCAAGAGTTATGGCATTCA CTGGGTCCGCCAGGCCCCAGGCAAGGGGCTGGAG TGGGTGGCAGTTATCTGGCCCCGACGAGATACACA GTATGCAGACTCCGTGAAGGGCCGAGTCACCATGT ACAGAGACGACTATAGGAATACGGTCTATCTACAG ATGAACAGCCTGAGATTCGATGACGCGGCTCTGTA TCGGTGTGCGAGAGATCGCGGTGAAGACAATCCCA TAGATTTCTGGGGCCAGGGAACCCTGGTCACCGTC TCCTCA |
| 94 | F-8C VL nucleotide sequence | CAGGCTGTGCTGACTCAGCCGTCTTCCCTCTCTGCA TCTCCTGGAGCATCAGCCAGTCTCACCTGCACCTT GCTCAGCGGCATCAATGTTGGTCCCTACTGGATAT ACTGGTATCAGCAGAAGGCAGGGAGTCCTCCCCAG TTTCTCCTCAGGTACAGGTCAGACTCAGATGAGGA GCAGGGCTCTGAGGTCCCCAGCCGCTTCTCTGGAT CCAAAGATGCCTCGGCCAATGCAGGGATTTTGGTC ATCTCTGGGCTCCAGTCTGAAGATGAAGCTGACTA TTACTGTATGATCTGGCACAGGACCGGTGTGATTT TCGGCGGAGGGACCAAGCTGACCGTCCTA |
| 95 | F-8C VH amino acid sequence | QVQLAESGGGVVQPGGSLRLSCAASGFSLKSYGIHW VRQAPGKGLEWVAVIWPRRDTQYADSVKGRVTMY RDDYRNTVYLQMNSLRFDDAALYRCARDRGEDNPI DFWGQGTLVTVSS |
| 96 | F-8C VL amino acid sequence | QAVLTQPSSLSASPGASASLTCTLLSGINVGPYWIYW YQQKAGSPPQFLLRYRSDSDEEQGSEVPSRFSGSKDA SANAGILVISGLQSEDEADYYCMIWHRTGVIFGGGTK LTVL |

TABLE 25

Amino Acid and Nucleotide Sequences of Antibody 21-6M

| SEQ ID NO | DESCRIPTION | SEQUENCE |
|---|---|---|
| 97 | 21-6M VH nucleotide sequence | CAGGTGCAGCTGGTGCAGTCTGGGGCTGAGATTA AGAGGCCTGGGGCCTCAGTGAAGGTCTCCTGCAA GGCGTCTGGATACATTTTCACCAGCTTTGGTATCA ACTGGGTGCGACAGGCCCCTGGACAAGGGCTTGA GTGGATGGGATGGATGAACTCCAACACTGGTGAT GCGGACTCTGTACAGAAGTTCCAGGGCAGACTCA CCATGACCACCGACCCCTCCACAAGTACAGCCTA TATGGAACTGAGGAATCTGAGATCTGACGACACG GCCGTATATTATTGCGCGAGAATGAACTTCTTTGG TTCGCAGTGGGAAGTGAACTGGTTCGACCCCTGG GGCCAGGGAACCCTGATCACCGTCTCCTCA |
| 98 | 21-6M VL nucleotide sequence | CAGTCTGTGGTGACTCAGCCACCCTCAGCGTCTGG GACCCCCGGGCAGAGGATCACCATCTCCTGTTCTG GAAGCAGGTCCAACGTCGAAAGAAATTCTGTTTA CTGGTACCAGCAGCTCCGAGGAACGGCCCCCAAA CTTCTCATCTATATGAGCAATCAGCGCCCCTCAGG GGTCCCTGACCGATTCTCTGGCTCTCGTTCTGGCA CCTCAGCCTCCCTGGCCATCACTGGGCTTCGGTCC GAGGATGAGGCTGATTATTATTGTGCAGTTTGGG ATGACAATCTCAGAGGCTGGGTGTTCGGCGGAGG GACCGAGGTGACCGTCCTA |
| 99 | 21-6M VH amino acid sequence | QVQLVQSGAEIKRPGASVKVSCKASGYIFTSFGINW VRQAPGQGLEWMGWMNSNTGDADSVQKFQGRLT MTTDPSTSTAYMELRNLRSDDTAVYYCARMNFFGS QWEVNWFDPWGQGTLITVSS |
| 100 | 21-6M VL amino acid sequence | QSVVTQPPSASGTPGQRITISCSGSRSNVERNSVYWY QQLRGTAPKLLIYMSNQRPSGVPDRFSGSRSGTSASL AITGLRSEDEADYYCAVWDDNLRGWVFGGGTEVT VL |

TABLE 26

Amino Acid and Nucleotide Sequences of Antibody 22-14F

| SEQ ID NO | DESCRIPTION | SEQUENCE |
|---|---|---|
| 101 | 22-14F VH nucleotide sequence | CCAGGTGCACCTGGTGCAGTCTGGGGCTGAGATT AAGAGGCCTGGGGCCTCAGTGAAGGTCTCCTGCA AGGCGTCTGGATACACTTTCACCAGCTTTGGTATC AACTGGGTGCGACAGGCCCCTGGACAAGGGCTTG AGTGGATGGGATGGATGAACTCCAACAGTGGTGA TGCGGACTCTGCACAGAAGTTCCAGGGCAGACTC ACTATGACCACCGACACCTCCACAAGTACAGCCT ACATGGAGCTGAGGAATCTGAGATCTGAGGACAC GGCCGTATATTATTGCGCGAGAATGAATTTCCGTG GTTCGAAGTGGGAGGTGAACTGGTTCGACCCCTG GGGCCAGGGAACCCTGATCACCGTCTCCTCA |
| 102 | 22-14F VL nucleotide sequence | CAGTCTGTGGTGACTCAGCCACCCTCAGCGTCTGG GACCCCCGGGCAGAGGGTCACCATCTCCTGTTCTG GAAGCAGGTCCAACGTCGAAAGAAATTTTGTTTA CTGGTACCAGCAACTCCCAGGAACGGCCCCCAAA CTTCTCATCTATATGAACAGTCAGCGGCCCTCAGG GGTCCCTGACCGATTCTCTGGCTCTCGTTCTGGCA CCTCAGCCTCCCTGGCCATCACTGGGCTTCGGTCC GAGGATGAGGCTGACTATTATTGTGCAACTTGGG ATGACAATCTGAGAGGCTGGGTGTTCGGCGGAGG GACCAAGGTGACCGTCCTA |
| 103 | 22-14F VH amino acid sequence | QVHLVQSGAEIKRPGASVKVSCKASGYTFTSFGINW VRQAPGQGLEWMGWMNSNSGDADSAQKFQGRLT MTTDTSTSTAYMELRNLRSEDTAVYYCARMNFRGS KWEVNWFDPWGQGTLITVSS |

TABLE 26-continued

Amino Acid and Nucleotide Sequences of Antibody 22-14F

| SEQ ID NO | DESCRIPTION | SEQUENCE |
| --- | --- | --- |
| 104 | 22-14F VL amino acid sequence | QSVVTQPPSASGTPGQRVTISCSGSRSNVERNFVYW YQQLPGTAPKLLIYMNSQRPSGVPDRFSGSRSGTSAS LAITGLRSEDEADYYCATWDDNLRGWVFGGGTKV TVL |

TABLE 27

Amino Acid and Nucleotide Sequences of Antibody 24-5D

| SEQ ID NO | DESCRIPTION | SEQUENCE |
| --- | --- | --- |
| 105 | 24-5D VH nucleotide sequence | CAGGTGCAGCTGGTGCAGTCTGGGGCTGAGATTA AGAGGCCTGGGGCCTCAGTGAAGGTCTCCTGCAA GGCGTCTGGATACACCTTCACCAGATTTGGTATCA ACTGGGTGCGACAGGCCCCTGGACAAGGGCTTGA GTGGATGGGATGGATGAACTCCAACACTGGTGAT GCGGACTCTGCACAGAAGTTCCAGGGCAGACTCA GTATGACCACCGACACCTCCACAAGTACAGCCTA CATGGAGCTGAAGAGTCTGACATCTGACGACACG GCCGTATATTTTTGCGCGAGAATGAATTACTGGGG GTCGAAGTGGGACGTGAACTGGTTCGACCCCTGG GGCCAGGGAACCCTGATCACCGTCTCCTCA |
| 106 | 24-5D VL nucleotide sequence | CAGTCTGTGGTGACTCAGCCACCCTCAGCGTCTGG GACCCCCGGGCAGAGGGTCACCATCTCCTGTTCTG GAAGAAGGACCAACGTGGAAAGAAATTCTGTCTA CTGGTACCAGCAGCTCCCAGGAACGGCCCCCAAA CTTCTCATCTATATGAGCAATAAGCGCCCCTCAGG GGTCCCTGACCGATTCTCCGGCTCTCGTTCTGGCA CCTCTGCCTCCCTGGCCATCACTGGGCTTCGGTCC GAGGATGAGGCTGATTATTATTGTGCAGTTTGGG ATGACAATCTGAGAGGCTGGGTGTTCGGCGGAGG GACCAAGGTGACCGTCCTA |
| 107 | 24-5D VH amino acid sequence | QVQLVQSGAEIKRPGASVKVSCKASGYTFTRFGINW VRQAPGQGLEWMGWMNSNTGDADSAQKFQGRLS MTTDTSTSTAYMELKSLTSDDTAVYFCARMNYWGS KWDVNWFDPWGQGTLITVSS |
| 108 | 24-5D VL amino acid sequence | QSVVTQPPSASGTPGQRVTISCSGRRTNVERNSVYW YQQLPGTAPKLLIYMSNKRPSGVPDRFSGSRSGTSAS LAITGLRSEDEADYYCAVWDDNLRGWVFGGGTKV TVL |

TABLE 28

Amino Acid Sequences of twenty-seven antibodies complementarity-determining regions (CDRs)

| SEQ ID NO | DESCRIPTION | SEQUENCE |
| --- | --- | --- |
| 109-111 | 15-6J CDR Heavy chain sequence (CDRH) | CDRH1: GFSFRHYGMH<br>CDRH2: VVWHDGRETHYGDSV<br>CDRH3: DRGSDEPIDY<br>SEQ ID Nos: 109-111 (CDR 1, CDR2, CDR3 respectively) |
| 112-114 | 15-6J CDR Light chain sequence (CDRL) | CDRL1: TLRSDVTVSPWTY<br>CDRL2: KSDSDKYQGS<br>CDRL3: QTWHTTTV<br>SEQ ID Nos: 112-114 (CDR 1, CDR2, CDR3 respectively) |

TABLE 28-continued

Amino Acid Sequences of twenty-seven antibodies complementarity-determining regions (CDRs)

| SEQ ID NO | DESCRIPTION | SEQUENCE |
|---|---|---|
| 115-117 | 23-12O CDR Heavy chain sequence (CDRH) | CDRH1: GFSFRHYGMH<br>CDRH2: VVWHDGRETHYGDSV<br>CDRH3: DRGSDEPIDY<br>SEQ ID Nos: 115-117 (CDR 1, CDR2, CDR3 respectively) |
| 118-120 | 23-12O CDR Light chain sequence (CDRL) | CDRL1: TLRSDVTVSPWTY<br>CDRL2: KSDSDKYQGS<br>CDRL3: QTWHTSTV<br>SEQ ID Nos: 118-120 (CDR 1, CDR2, CDR3 respectively) |
| 121-123 | 31-2C CDR Heavy chain sequence (CDRH) | CDRH1: GFSFRYYGFH<br>CDRH2: VVWHDGRETHYGDSV<br>CDRH3: DRGSDEPIDY<br>SEQ ID Nos: 121-123 (CDR 1, CDR2, CDR3 respectively) |
| 124-126 | 31-2C CDR Light chain sequence (CDRL) | CDRL1: TLRSGLTVSPWIY<br>CDRL2: KSDSENYRGS<br>CDRL3: QTWHTSTV<br>SEQ ID Nos: 124-126 (CDR 1, CDR2, CDR3 respectively) |
| 127-129 | 15-20G CDR Heavy chain sequence (CDRH) | CDRH1: GFSFRYYGFH<br>CDRH2: VVWHDGRETHYGDSV<br>CDRH3: DRGSDEPIDY<br>SEQ ID Nos: 127-129 (CDR 1, CDR2, CDR3 respectively) |
| 130-132 | 15-20G CDR Light chain sequence (CDRL) | CDRL1: TLRSDLTVSPWIY<br>CDRL2: KSDSNNYHGS<br>CDRL3: QTWHTTTV<br>SEQ ID Nos: 130-132 (CDR 1, CDR2, CDR3 respectively) |
| 133-135 | 4-22O CDR Heavy chain sequence (CDRH) | CDRH1: GFPFRYYGFH<br>CDRH2: VVWHNGRETYYEDSV<br>CDRH3: DRGSDEPIDY<br>SEQ ID Nos: 133-135 (CDR 1, CDR2, CDR3 respectively) |
| 136-138 | 4-22O CDR Light chain sequence (CDRL) | CDRL1: TLRSDLTVGPYWMY<br>CDRL2: KSDSEKYQGS<br>CDRL3: QTWHANTV<br>SEQ ID Nos: 136-138 (CDR 1, CDR2, CDR3 respectively) |
| 139-141 | 6-20C CDR Heavy chain sequence (CDRH) | CDRH1: GFSFRRFGMH<br>CDRH2: VVWHDGRETHYGDSV<br>CDRH3: DPGQDEAIDY<br>SEQ ID Nos: 139-141 (CDR 1, CDR2, CDR3 respectively) |
| 142-144 | 6-20C CDR Light chain sequence (CDRL) | CDRL1: TLHSGLTVGPYWIY<br>CDRL2: KSDSEEYRAS<br>CDRL3: MTWHTNKV<br>SEQ ID Nos: 142-144 (CDR 1, CDR2, CDR3 respectively) |
| 145-147 | J-5N CDR Heavy chain sequence (CDRH) | CDRH1: GFSLRSFGMH<br>CDRH2: VIWPRRSQIQYADSV<br>CDRH3: DPGEDNPIDY<br>SEQ ID Nos: 145-147 (CDR 1, CDR2, CDR3 respectively) |
| 148-150 | J-5N CDR Light chain sequence (CDRL) | CDRL1: TFLSGINVGPYWIY<br>CDRL2: KSDSDKHQGS<br>CDRL3: MIWHVSGV<br>SEQ ID Nos: 148-150 (CDR 1, CDR2, CDR3 respectively) |

TABLE 28-continued

Amino Acid Sequences of twenty-seven antibodies complementarity-determining regions (CDRs)

| SEQ ID NO | DESCRIPTION | SEQUENCE |
|---|---|---|
| 151-153 | F-8C CDR Heavy chain sequence (CDRH) | CDRH1: GFSLKSYGIH<br>CDRH2: VIWPRRDTQYADSV<br>CDRH3: DRGEDNPIDF<br>SEQ ID Nos: 151-153 (CDR 1, CDR2, CDR3 respectively) |
| 154-156 | F-8C CDR Light chain sequence (CDRL) | CDRL1: TLLSGINVGPYWIY<br>CDRL2: RSDSDEEQGS<br>CDRL3: MIWHRTGV<br>SEQ ID Nos: 154-156 (CDR 1, CDR2, CDR3 respectively) |
| 157-159 | B-21J CDR Heavy chain sequence (CDRH) | CDRH1: GFSFRHYGMH<br>CDRH2: VIWHNGRDREYADSV<br>CDRH3: DRGEDEPIDF<br>SEQ ID Nos: 157-159 (CDR 1, CDR2, CDR3 respectively) |
| 160-162 | B-21J CDR Light chain sequence (CDRL) | CDRL1: TLRSGLSAGPKWIY<br>CDRL2: KSDSEERRSS<br>CDRL3: AIWHSNVV<br>SEQ ID Nos: 160-162 (CDR 1, CDR2, CDR3 respectively) |
| 163-165 | J-8G CDR Heavy chain sequence (CDRH) | CDRH1: GFSFRHYGMH<br>CDRH2: VIWHNGRDKDYADSV<br>CDRH3: DRGEDEPIDF<br>SEQ ID Nos: 163-165 (CDR 1, CDR2, CDR3 respectively) |
| 166-168 | J-8G CDR Light chain sequence (CDRL) | CDRL1: TLRSGLNVGPYWIY<br>CDRL2: KSDSEKRRSS<br>CDRL3: AIWHSNAV<br>SEQ ID Nos: 166-168 (CDR 1, CDR2, CDR3 respectively) |
| 169-171 | 9-5L CDR Heavy chain sequence (CDRH) | CDRH1: GFTLKRYGIH<br>CDRH2: VTWHDGNIYYADSV<br>CDRH3: DAGQNAPIDL<br>SEQ ID Nos: 169-171 (CDR 1, CDR2, CDR3 respectively) |
| 172-174 | 9-5L CDR Light chain sequence (CDRL) | CDRL1: TLPSGINVATHWIY<br>CDRL2: KSDSDIQHGS<br>CDRL3: MIWYSTAV<br>SEQ ID Nos: 172-174 (CDR 1, CDR2, CDR3 respectively) |
| 175-177 | 2-20G CDR Heavy chain sequence (CDRH) | CDRH1: GFTFPNAWFN<br>CDRH2: RIKSHSDGGTADYAAPV<br>CDRH3: LEIYHPVDV<br>SEQ ID Nos: 175-177 (CDR 1, CDR2, CDR3 respectively) |
| 178-180 | 2-20G CDR Light chain sequence (CDRL) | CDRL1: RSSHSLPRDDEYSYLN<br>CDRL2: RVSKRDS<br>CDRL3: MQGTYWPGT<br>SEQ ID Nos: 178-180 (CDR 1, CDR2, CDR3 respectively) |
| 181-183 | 3-17I CDR Heavy chain sequence (CDRH) | CDRH1: GFTFITAWMT<br>CDRH2: LIKSGNDGGAIEYAAPV<br>CDRH3: NDVALVWGVTPPLLL<br>SEQ ID Nos: 181-183 (CDR 1, CDR2, CDR3 respectively) |
| 184-186 | 3-17I CDR Light chain sequence (CDRL) | CDRL1: TLSSGHGNYPVA<br>CDRL2: NADGSHIKGA<br>CDRL3: QTWAPGW<br>SEQ ID Nos: 184-186 (CDR 1, CDR2, CDR3 respectively) |

TABLE 28-continued

Amino Acid Sequences of twenty-seven antibodies complementarity-determining regions (CDRs)

| SEQ ID NO | DESCRIPTION | SEQUENCE |
|---|---|---|
| 187-189 | F-18D CDR Heavy chain sequence (CDRH) | CDRH1: GFVFTTAWMN<br>CDRH2: RIKSKNEAETTDYAAPV<br>CDRH3: LETYYESDF<br>SEQ ID Nos: 187-189 (CDR 1, CDR2, CDR3 respectively) |
| 190-192 | F-18D CDR Light chain sequence (CDRL) | CDRL1: RSSQSLAEREEDILLN<br>CDRL2: RVSKRES<br>CDRL3: MQRTHWPQT<br>SEQ ID Nos: 190-192 (CDR 1, CDR2, CDR3 respectively) |
| 193-195 | 41-180 CDR Heavy chain sequence (CDRH) | CDRH1: GFTFNHDWMT<br>CDRH2: NIIQDGSETYYVDSV<br>CDRH3: GRVSMDV<br>SEQ ID Nos: 193-195 (CDR 1, CDR2, CDR3 respectively) |
| 196-198 | 41-180 CDR Light chain sequence (CDRL) | CDRL1: SGSSSNIGSNTVN<br>CDRL2: TDNQRPS<br>CDRL3: AARDGSLDVW<br>SEQ ID Nos: 196-198 (CDR 1, CDR2, CDR3 respectively) |
| 199-201 | 18-11C CDR Heavy chain sequence (CDRH) | CDRH1: GYTFTSFGIN<br>CDRH2: WMNSNSGDADSAQKF<br>CDRH3: MNFRGSKWEVNWFDP<br>SEQ ID Nos: 199-201 (CDR 1, CDR2, CDR3 respectively) |
| 202-204 | 18-11C CDR Light chain sequence (CDRL) | CDRL1: SGSRSNVERNFVY<br>CDRL2: MNSQRPS<br>CDRL3: ATWDDNLRGW<br>SEQ ID Nos: 202-204 (CDR 1, CDR2, CDR3 respectively) |
| 205-207 | 22-14F CDR Heavy chain sequence (CDRH) | CDRH1: GYTFTSFGIN<br>CDRH2: WMNSNSGDADSAQKF<br>CDRH3: MNFRGSKWEVNWFDP<br>SEQ ID Nos: 205-207 (CDR 1, CDR2, CDR3 respectively) |
| 208-210 | 22-14F CDR Light chain sequence (CDRL) | CDRL1: SGSRSNVERNFVY<br>CDRL2: MNSQRPS<br>CDRL3: ATWDDNLRGW<br>SEQ ID Nos: 208-210 (CDR 1, CDR2, CDR3 respectively) |
| 211-213 | 20-2D CDR Heavy chain sequence (CDRH) | CDRH1: GYTFTRFGIN<br>CDRH2: WMNSNSGNADSAQKF<br>CDRH3: MNYRGSKWEINWFDP<br>SEQ ID Nos: 211-213 (CDR 1, CDR2, CDR3 respectively) |
| 214-216 | 20-2D CDR Light chain sequence (CDRL) | CDRL1: SGSRSNVQRNFVY<br>CDRL2: MNNNRPS<br>CDRL3: ATWDDNLRGW<br>SEQ ID Nos: 214-216 (CDR 1, CDR2, CDR3 respectively) |
| 217-219 | 36-21L CDR Heavy chain sequence (CDRH) | CDRH1: GYTFTGFGIN<br>CDRH2: WMNSNTGDADSAQKF<br>CDRH3: MNFLGSKWEVNWFDP<br>SEQ ID Nos: 217-219 (CDR 1, CDR2, CDR3 respectively) |
| 220-222 | 36-21L CDR Light chain sequence (CDRL) | CDRL1: RSSHSLPRDDEYSYLN<br>CDRL2: RVSKRDS<br>CDRL3: MQGTYWPGT<br>SEQ ID Nos: 220-222 (CDR 1, CDR2, CDR3 respectively) |

TABLE 28-continued

Amino Acid Sequences of twenty-seven antibodies complementarity-determining regions (CDRs)

| SEQ ID NO | DESCRIPTION | SEQUENCE |
|---|---|---|
| 223-225 | 36-19H CDR Heavy chain sequence (CDRH) | CDRH1: GYIFTNFGIN<br>CDRH2: WMNSKYGNADSAHKF<br>CDRH3: MNYRDSKWDVNWFDP<br>SEQ ID Nos: 223-225 (CDR 1, CDR2, CDR3 respectively) |
| 226-228 | 36-19H CDR Light chain sequence (CDRL) | CDRL1: SGSRSNVERNFVY<br>CDRL2: MNNQRPS<br>CDRL3: AVWDDNLRGW<br>SEQ ID Nos: 226-228 (CDR 1, CDR2, CDR3 respectively) |
| 229-231 | 21-6M CDR Heavy chain sequence (CDRH) | CDRH1: GYIFTSFGIN<br>CDRH2: WMNSNTGDADSVQKF<br>CDRH3: MNFFGSQWEVNWFDP<br>SEQ ID Nos: 229-231 (CDR 1, CDR2, CDR3 respectively) |
| 232-234 | 21-6M CDR Light chain sequence (CDRL) | CDRL1: SGSRSNVERNSVY<br>CDRL2: MSNQRPS<br>CDRL3: AVWDDNLRGW<br>SEQ ID Nos: 232-234 (CDR 1, CDR2, CDR3 respectively) |
| 235-237 | 24-5D CDR Heavy chain sequence (CDRH) | CDRH1: GYTFTRFGIN<br>CDRH2: WMNSNTGDADSAQKF<br>CDRH3: MNYWGSKWDVNWFDP<br>SEQ ID Nos: 235-237 (CDR 1, CDR2, CDR3 respectively) |
| 238-240 | 24-5D CDR Light chain sequence (CDRL) | CDRL1: SGRRTNVERNSVY<br>CDRL2: MSNKRPS<br>CDRL3: AVWDDNLRGW<br>SEQ ID Nos: 238-240 (CDR 1, CDR2, CDR3 respectively) |
| 241-243 | 12-14G CDR Heavy chain sequence (CDRH) | CDRH1: GYTFTNYGVN<br>CDRH2: WMNTNSGDTGYAQKF<br>CDRH3: AYFFDSWNKGNWFDP<br>SEQ ID Nos: 241-243 (CDR 1, CDR2, CDR3 respectively) |
| 244-246 | 12-14G CDR Light chain sequence (CDRL) | CDRL1: SGGSSNLGRSYIY<br>CDRL2: KNSQRPS<br>CDRL3: AAWDDSLSGSW<br>SEQ ID Nos: 244-246 (CDR 1, CDR2, CDR3 respectively) |
| 247-249 | 2-8M CDR Heavy chain sequence (CDRH) | CDRH1: GGYVTIKDNYWV<br>CDRH2: SMSYSGNAYYNPSL<br>CDRH3: RSAAAGGGNEWFDP<br>SEQ ID Nos: 247-249 (CDR 1, CDR2, CDR3 respectively) |
| 250-252 | 2-8M CDR Light chain sequence (CDRL) | CDRL1: SGSTFNIGNNYVS<br>CDRL2: DNDKRPS<br>CDRL3: ATWDNRLDAV<br>SEQ ID Nos: 250-252 (CDR 1, CDR2, CDR3 respectively) |
| 253-255 | 6-8N CDR Heavy chain sequence (CDRH) | CDRH1: GFAFTTAWMT<br>CDRH2: LIKSTNDGGSIDYAAPV<br>CDRH3: NDVVRLRGVTPPILL<br>SEQ ID Nos: 253-255 (CDR 1, CDR2, CDR3 respectively) |
| 256-258 | 6-8N CDR Light chain sequence (CDRL) | CDRL1: TLSSGHHSYPVA<br>CDRL2: NGDGSHTKGDG<br>CDRL3: QTWATGW<br>SEQ ID Nos: 256-258 (CDR 1, CDR2, CDR3 respectively) |

TABLE 28-continued

Amino Acid Sequences of twenty-seven antibodies complementarity-determining regions (CDRs)

| SEQ ID NO | DESCRIPTION | SEQUENCE |
|---|---|---|
| 259-261 | 5-14N CDR Heavy chain sequence (CDRH) | CDRH1: GYIFTNFGIN<br>CDRH2: WMNSRTGDADSAQNF<br>CDRH3: MNFLGSRWEVNWFDP<br>SEQ ID Nos: 259-261 (CDR 1, CDR2, CDR3 respectively) |
| 262-264 | 5-14N CDR Light chain sequence (CDRL) | CDRL1: SGSRSNVERNFFY<br>CDRL2: MNSQRPAG<br>CDRL3: ATWDDNLRGW<br>SEQ ID Nos: 262-264 (CDR 1, CDR2, CDR3 respectively) |
| 265-267 | 11-19C CDR Heavy chain sequence (CDRH) | CDRH1: GYIFTSFGIN<br>CDRH2: WMNSNTGDADSLQKF<br>CDRH3: MNFHGSRWDVNWFDP<br>SEQ ID Nos: 265-267 (CDR 1, CDR2, CDR3 respectively) |
| 268-270 | 11-19C CDR Light chain sequence (CDRL) | CDRL1: SGSGSNVERNSVY<br>CDRL2: MSNRPRSG<br>CDRL3: AVWDDSLRGW<br>SEQ ID Nos: 268-270 (CDR 1, CDR2, CDR3 respectively) |

One aspect of the present disclosure features the new antibodies specific to SSEA-4. The anti-SSEA-4 antibody binds to Neu5Acα2→3Galβ1→3GalNAcβ1→3Galα1→4Galβ1→4Glcβ1.

One aspect of the present disclosure features the new antibodies specific to SSEA-3. The anti-SSEA-3 antibody binds to 2Galβ1→3GalNAcβ1→3Galα1→4Galβ1→4Glcβ1.

One aspect of the present disclosure features the new antibodies specific to Globo H. The anti-Globo H antibody binds to Fucα1→2 Galβ1→3 GalNAcβ1→3 Galα1→4 Galβ1→4 Glc.

Any of the antibodies described herein can be a full length antibody or an antigen-binding fragment thereof. In some examples, the antigen binding fragment is a Fab fragment, a F(ab')$_2$ fragment, or a single-chain Fv fragment. In some examples, the antigen binding fragment is a Fab fragment, a F(ab')$_2$ fragment, or a single-chain Fv fragment. In some examples, the antibody is a human antibody, a chimeric antibody, or a single-chain antibody.

Any of the antibodies described herein has one or more characteristics of: (a) is a recombinant antibody, a monoclonal antibody, a chimeric antibody, a human antibody, an antibody fragment, a bispecific antibody, a monospecific antibody, a monovalent antibody, an IgG$_1$ antibody, an IgG$_2$ antibody, or derivative of an antibody; (b) is a human, murine, or chimeric antibody, antigen-binding fragment, or derivative of an antibody; (c) is a single-chain antibody fragment, a multibody, a Fab fragment, and/or an immunoglobulin of the IgG, IgM, IgA, IgE, IgD isotypes and/or subclasses thereof; (d) has one or more of the following characteristics: (i) mediates ADCC and/or CDC of cancer cells; (ii) induces and/or promotes apoptosis of cancer cells; (iii) inhibits proliferation of target cells of cancer cells; (iv) induces and/or promotes phagocytosis of cancer cells; and/or (v) induces and/or promotes the release of cytotoxic agents; (e) specifically binds the tumor-associated carbohydrate antigen, which is a tumor-specific carbohydrate antigen; (f) does not bind an antigen expressed on non-cancer cells, non-tumor cells, benign cancer cells and/or benign tumor cells; and/or (g) specifically binds a tumor-associated carbohydrate antigen expressed on cancer stem cells and on normal cancer cells.

Preferably the binding of the antibodies to their respective antigens is specific. The term "specific" is generally used to refer to the situation in which one member of a binding pair will not show any significant binding to molecules other than its specific binding partner (s) and e.g. has less than about 30%, preferably 20%, 10%, or 1% cross-reactivity with any other molecule other than those specified herein.

Immunization of Host Animals and Hybridoma Technology

In one embodiment, the present invention provides for a method for making a hybridoma that expresses an antibody that specifically binds to a carbohydrate antigen (e.g., Globo H). The method contains the following steps: immunizing an animal with a composition that includes a carbohydrate antigen (e.g., Globo H); isolating splenocytes from the animal; generating hybridomas from the splenocytes; and selecting a hybridoma that produces an antibody that specifically binds to Globo H. Kohler and Milstein, Nature, 256: 495, 1975. Harlow, E. and Lane, D. Antibodies: A Laboratory Manual, Cold Spring Harbor Laboratory Press, Cold Spring Harbor, N.Y., 1988.

In one embodiment, carbohydrate antigen is used to immunize mice subcutaneously. One or more boosts may or may not be given. The titers of the antibodies in the plasma can be monitored by, e.g., ELISA (enzyme-linked immunosorbent assay) or flow cytometry. Mice with sufficient titers of anti-carbohydrate antigen antibodies are used for fusions. Mice may or may not be boosted with antigen 3 days before sacrifice and removal of the spleen. The mouse splenocytes are isolated and fused with PEG to a mouse myeloma cell line. The resulting hybridomas are then screened for the production of antigen-specific antibodies. Cells are plated, and then incubated in selective medium. Supernatants from individual wells are then screened by ELISA for human anti-carbohydrate antigen monoclonal antibodies. The antibody secreting hybridomas are replated, screened again, and if still positive for anti-carbohydrate antigen antibodies, can be subcloned by limiting dilution.

Exemplary Polyclonal antibodies against the anti-Globo series antigens antibodies may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum.

Polyclonal antibodies are generally raised in host animals (e.g., rabbit, mouse, horse, or goat) by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, etc.

Any mammalian animal may be immunized with the antigen for producing the desired antibodies. In general, animals of Rodentia, Lagomorpha, or Primates can be used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Animals are immunized against the antigen, immunogenic conjugates, or derivatives by combining 1 mg or 1 µg of the peptide or conjugate (for rabbits or mice, respectively) with 3 volumes of Freund's incomplete adjuvant.

Animals can be boosted until the titer plateaus by several administrations of antigen mixed with an appropriately amount of Freund's incomplete adjuvant every 4 to 21 days. Animals are boosted with ⅕ to ¹/₁₀ the original amount of peptide or conjugate in Freund's complete adjuvant by subcutaneous injection at multiple sites. Seven to 14 days later the animals are bled and the serum is assayed for antibody titer. An appropriate carrier may also be used for immunization. After immunization as above, serum is examined by a standard method for an increase in the amount of desired antibodies. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

In some embodiments, antibodies can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that can specifically bind to the protein used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically include hypoxanthine, aminopterin, and thymidine (HAT medium), which substances prevent the growth of HGPRT-deficient cells.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used in this method.

Applying any of the conventional methods, including those described above, hybridoma cells producing antibodies that bind to epitopes described herein can be identified and selected for further characterization.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In addition, the hybridoma cells may be grown in vivo as ascites tumors in an animal. For example, the obtained hybridomas can be subsequently transplanted into the abdominal cavity of a mouse and the ascites are harvested.

The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention.

Activity Assays

Antibodies of the invention can be characterized for their physical/chemical properties and biological functions by various assays known in the art.

Antibodies, or antigen-binding fragments, variants or derivatives thereof of the present disclosure can also be described or specified in terms of their binding affinity to an antigen. The affinity of an antibody for a carbohydrate antigen can be determined experimentally using any suitable method (see, e.g., Berzofsky et al, "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-carbohydrate antigen interaction can vary if measured under different conditions {e.g., salt concentration, pH). Thus, measurements of affinity and other antigen-binding parameters (e.g., $K_D$, $K_a$, Ka) are preferably made with standardized solutions of antibody and antigen, and a standardized buffer.

The present antibodies or antigen-binding portions thereof have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose cancer.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, chemiluminescent immunoassays, nanoparticle immunoassays, aptamer immunoassays, and protein A immunoassays.

Uses

An antibody of the invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, an antibody of the invention can be used for inhibiting antigen activities by contacting the antibody with the antigen such that antigen activity is inhibited. In one embodiment, the antigen is a human protein molecule.

"Administering" is referred to herein as providing a therapeutic composition of the invention to a patient. By way of example and not limitation, composition administration, e.g., injection, may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route or nasal route. Additionally, administration may also be by surgical deposition of a bolus or positioning of a medical device.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In one embodiment, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Antibodies of the invention can be used to treat, inhibit, delay progression of, prevent/delay recurrence of, ameliorate, or prevent diseases, disorders or conditions associated with abnormal expression and/or activity of Globo series antigens (Globo H, SSEA-3, SSEA-4), including but not limited to cancer, muscular disorders, ubiquitin-pathway-related genetic disorders, immune/inflammatory disorders, neurological disorders, and other ubiquitin pathway-related disorders.

In certain embodiments, an immunoconjugate comprising an antibody of the invention conjugated with a cytotoxic agent is administered to the patient. In some embodiments, the immunoconjugate and/or antigen to which it is bound is/are internalized by cells expressing one or more proteins on their cell surface which are associated with Globo series antigens, resulting in increased therapeutic efficacy of the immunoconjugate in killing the target cell with which it is associated. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

An antibody of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

Therapeutic Applications

Described herein are therapeutic methods that include administering to a subject in need of such treatment a therapeutically effective amount of a composition that includes one or more antibodies described herein.

In some embodiments, the subject (e.g., a human patient) in need of the treatment is diagnosed with, suspected of having, or at risk for cancer. Examples of the cancer include, but are not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In some embodiments, the cancer is sarcoma, skin cancer, leukemia, lymphoma, brain cancer, lung cancer, breast cancer, ovarian cancer, prostate cancer, colon cancer, or pancreas cancer. In some preferred embodiments, the cancer is brain cancer or glioblastoma multiforme (GBM) cancer.

In preferred embodiments, the antibody is capable of targeting Globo series antigens-expressing cancer cells. In some embodiments, the antibody is capable of targeting Globo series antigens on cancer cells. In some embodiments, the antibody is capable of targeting Globo series antigens in cancers.

The treatment results in reduction of tumor size, elimination of malignant cells, prevention of metastasis, prevention of relapse, reduction or killing of disseminated cancer, prolongation of survival and/or prolongation of time to tumor cancer progression.

In some embodiments, the treatment further comprises administering an additional therapy to said subject prior to, during or subsequent to said administering of the antibodies. In some embodiments, the additional therapy is treatment with a chemotherapeutic agent. In some embodiments, the additional therapy is radiation therapy.

The methods of the invention are particularly advantageous in treating and preventing early stage tumors, thereby preventing progression to the more advanced stages resulting in a reduction in the morbidity and mortality associated with advanced cancer. The methods of the invention are also advantageous in preventing the recurrence of a tumor or the regrowth of a tumor, for example, a dormant tumor that persists after removal of the primary tumor, or in reducing or preventing the occurrence of a tumor.

In some embodiments, the methods as disclosed herein are useful for the treatment or prevention of a cancer, for example where a cancer is characterized by increased Globo H, SSEA-3 and/or SSEA-4 expression. In some embodiments the cancer comprises a cancer stem cell. In some embodiments, the cancer is a pre-cancer, and/or a malignant cancer and/or a therapy resistant cancer. In some embodiments, the cancer is a brain cancer.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer, which include, but not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. A subject having cancer can be identified by routine medical examination.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

As used herein, the term "treating" refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect cancer, the symptom of cancer, or the predisposition toward cancer.

"Development" or "progression" of cancer means initial manifestations and/or ensuing progression of cancer. Development of cancer can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

The exemplary therapeutic compositions (also referred to herein as pharmaceutical compositions) generally include a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, intramuscular, intra-arterial, oral (e.g., inhalation), transdermal (topical), transmucosal, and rectal administration. Solutions or suspensions used for parenteral, intradermal, or subcutaneous application can include the following components: a sterile diluent such as water for injection, saline solution, phosphate buffered saline, tris-buffered saline, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. The pH value can be adjusted with acids or bases, such as hydrochloric acid or sodium hydroxide. The parenteral preparation can be enclosed in ampoules, disposable syringes, or multiple dose vials made of glass or plastic.

Exemplary pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Exemplary Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying, which yields a powder of the active ingredient plus any additional desired ingredient from a previously sterile-filtered solution thereof.

Exemplary oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Furthermore, for oral administration, the exemplary formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from polyglycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, or nasal administration the exemplary compounds/formulations can be delivered in the form of an aerosol spray from pressured container or dispenser which contains a suitable propellant, e.g., a gas such as carbon dioxide, or a nebulizer.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to implementations, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, which is incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The pharmaceutical formulations of the invention can be delivered parenterally, i.e., by intravenous (i.v.), subcutaneous (s.c.), intraperitoneal (i.p.), intramuscular (i.m.), subdermal (s.d.), or intradermal (i.d.) administration, by direct injection, via, for example, bolus injection, continuous infusion, or gene gun (e.g., to administer a vector vaccine to a subject, such as naked DNA or RNA). Formulations for injection can be presented in unit dosage form, e.g., in ampoules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

Dosage: Toxicity and therapeutic efficacy of such therapeutic compositions may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic compositions which exhibit high therapeutic indices are preferred. While compounds that exhibit toxic side effects can be used, care should be taken to design a delivery system that targets such compounds to the site of affected location to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, a therapeutically effective amount of a therapeutic composition (i.e., an effective dosage) may range from about 0.001 µg/kg to about 250 g/kg, 0.01 µg/kg to 10 g/kg, or 0.1 µg/kg to 1.0 g/kg or about or at least: 0.001, 0.002, 0.003, 0.004, 0.005, 0.006, 0.007, 0.008, 0.009; 0.01, 0.02, 0.03, 0.04, 0.05, 0.06, 0.07, 0.08, 0.09; 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, or 250 grams or micrograms per kilogram of patient body weight, or any range between any of the numbers listed herein, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

In other embodiments, a therapeutically effective amount of Globo series moiety in the therapeutic composition (i.e., an effective dosage) may range from about 0.001 µg/kg to about 250 g/kg, 0.01 µg/kg to 10 g/kg, or 0.1 µg/kg to 1.0 g/kg or about or at least: 0.001, 0.002, 0.003, 0.004, 0.005, 0.006, 0.007, 0.008, 0.009; 0.01, 0.02, 0.03, 0.04, 0.05, 0.06, 0.07, 0.08, 0.09; 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, or 250 grams or micrograms per kilogram of patient body weight, or any range between any of the numbers listed herein, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present. In one embodiment, the immunogenically effective amount of a pharmaceutically acceptable carrier comprising the vaccine ranges from about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.25, 1.5, 1.75, 2.0, 2.25, 2.5, 2.75, 3.0, 3.25, 3.5, 3.75, 4.0, 4.25, 4.5, 4.75 to about 5.0 µg, or any range between any of the numbers listed herein.

In some embodiments, the therapeutic compositions of the invention are administered to a subject in need thereof (e.g., one having a cancer such as breast cancer) in a method that on average extends progression free survival or overall survival over a control placebo, e.g., a phosphate buffered saline placebo, by about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 days, weeks, months, or years.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Clinical Sample Collection

In order to generate anti-Globo series antigens human monoclonal antibodies, B cells were isolated from peripheral blood of vaccinated patients. After administering Globo H-KLH vaccine (OBI-822/OBI-821) in a patient of recurrent ovarian cancer, blood samples were collected for the following analyzing procedure.

Example 2: Human Single B Cell Sorting and Cultivation

IgD⁻IgM⁻IgA⁻ memory B cells were freshly isolated from human peripheral blood and plated into 384-well tissue culture plates at a density of one cell per well using fluorescence-activated cell sorter. The sorted B cells were stimulated to secrete IgG and incubated for several days. After incubation, B cell lysates and culture supernatants were collected separately.

Example 3: Amplification of Antibody Genes

In obtaining Globo H, SSEA-3 or SSEA-4 binding clones, genes encoding Ig VH, Ig Vκ or Ig Vλ are recovered from B cell lysates using RT-PCR and cloned into IgG expression vectors. Recombinant antibodies are expressed by transfection of mammalian cells and used to confirm the binding specificities or to implement other functional assays.

Example 4: Globo H, SSEA-3 and SSEA-4 Binding Assays

To screen for anti-Globo series antigen human antibodies, the culture supernatants containing secreted IgG were assayed for Globo H, SSEA-3 or SSEA-4 binding specificities using ELISA.

1. Reagent/Buffer Preparation:
A. Globo H-ceramide, Globo H-lipid, SSEA-3-ceramide, SSEA-3-lipid, SSEA-4-ceramide and SSEA-4-lipid powder was dissolved in ethanol and storage at −20° C. 20 µg of antigen was added into 5 mL ethanol and mixed gently.
B. Adding 50 µL of coating antigen (0.2 µg of antigen/well) into each well. Covering, labeling and incubating at room temperature for overnight.
C. Adding 100 µL/well of Blocking Buffer (Sigma, Cat #B6429) into each well and incubating at room temperature for 30 minutes.

2. Addition of Culture Supernatants to Antigen-Coated Plate
A. After the blocking procedure, washing three times with 200 µL PBST Wash Buffer.
B. Transferring 50 µL of all diluted test samples to corresponding wells in the Antigen-Coated/Blocked Plate.
C. Incubating the plate at room temperature for 1 hour.
D. After incubating, washing three times with 200 µL PBST Wash Buffer.

3. Addition of Secondary Antibody to Antigen-Coated Plate
A. Pipetting 25 µL of Secondary Antibody to 4975 µL of Blocking Buffer and mixing gently. (Goat anti-human IgG-AP for IgG antibody detection)
B. Adding 50 µL of Secondary Antibody Solution and incubating at room temperature for 45 minutes.
C. After incubating, washing four times with 200 µL Wash Buffer.
D. Adding 100 µL Substrate Solution (Sigma, Cat #P7998) and incubating for 20 minutes at 37° C.
E. Stop reaction by adding 50 µL of Stop Solution (Sigma, Cat #A5852), mixing well and then reading the absorbance at 405 nm on the ELISA Plate Reader.

4. Data Analysis

A. The well that gives a reading above the cutoff value is defined as the potential Globo series antigen binding clone.

B. Cutoff value=X+0.1. (X is the mean OD value of negative control).

C. Controls were treated the same as test samples. The differences are that the positive control has primary Abs known positive Ab (anti-Globo H, anti-SSEA-3, anti-SSEA-4 antibody or no IgG added as the primary antibody is negative control).

D. Data were analyzed statistically by Mann-Whitney test using GraphPad Prism 5 Software.

5. Result

Figure 1B:
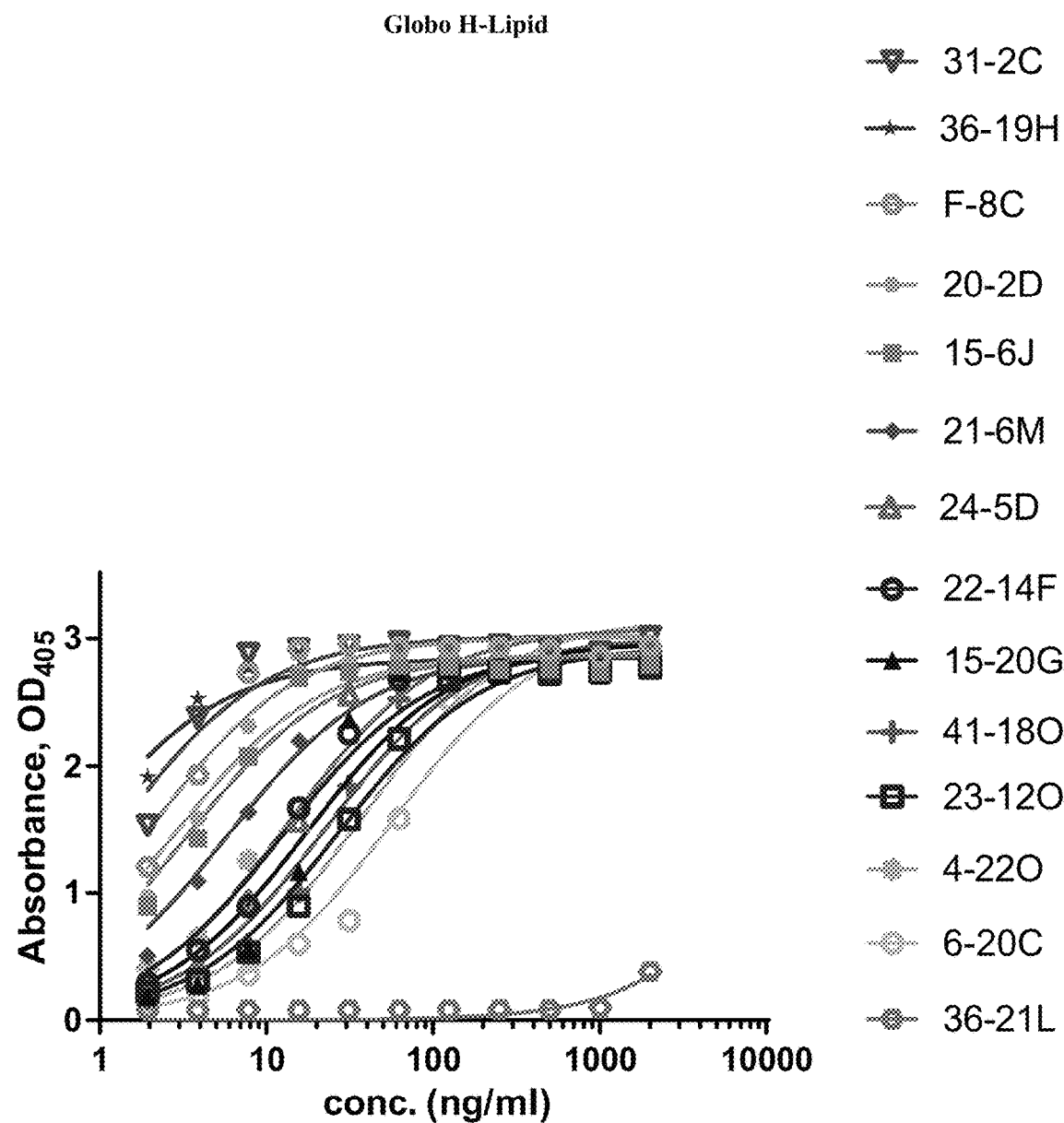
FIG. 1 shows the binding efficacy characterization between different human antibody clones by titration ELISA.
Figure 2A:
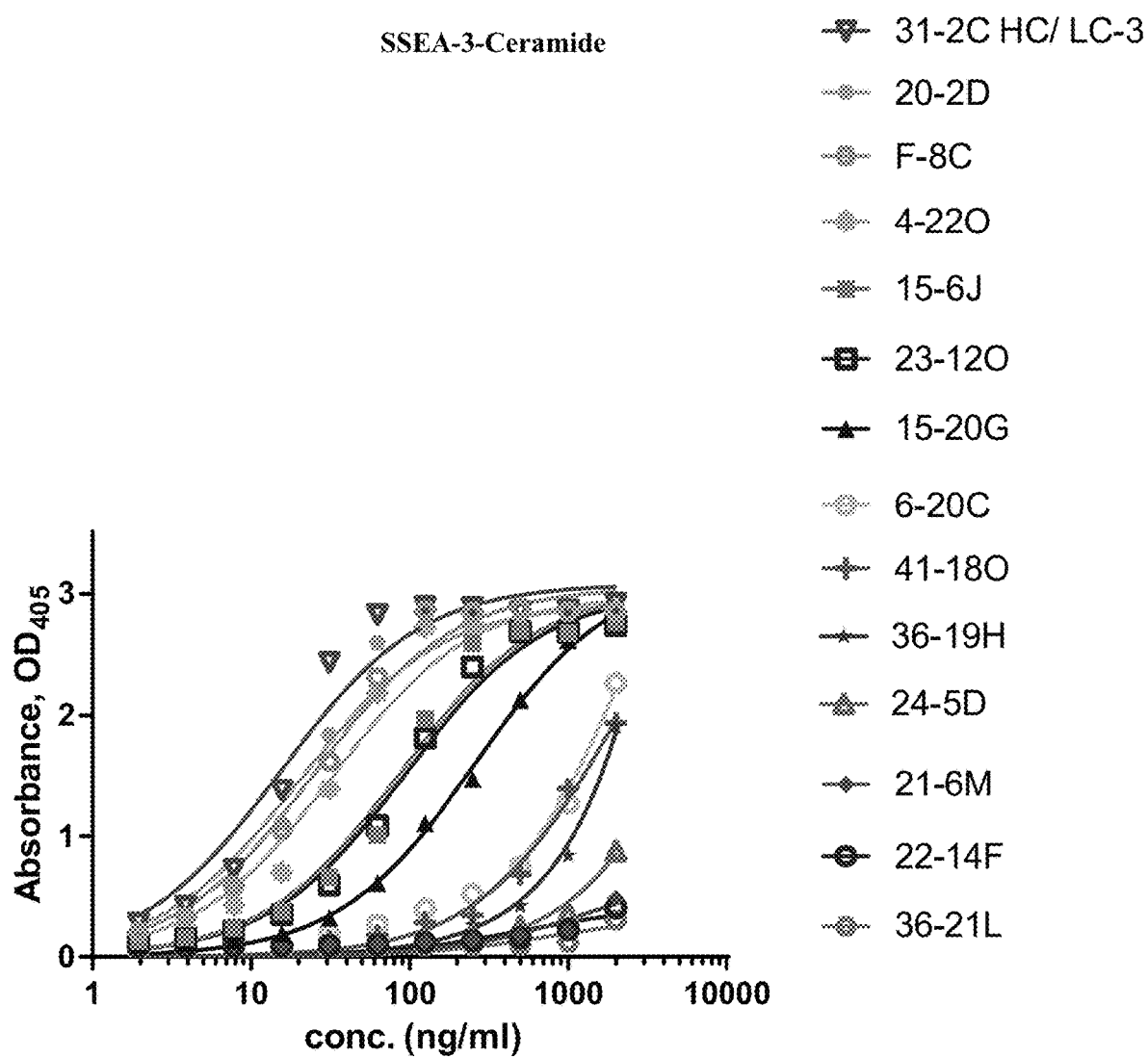
FIG. 2A uses SSEA-3-ceramide and FIG. 2B uses SSEA-3-lipid as the coating antigens.
Figure 2B:
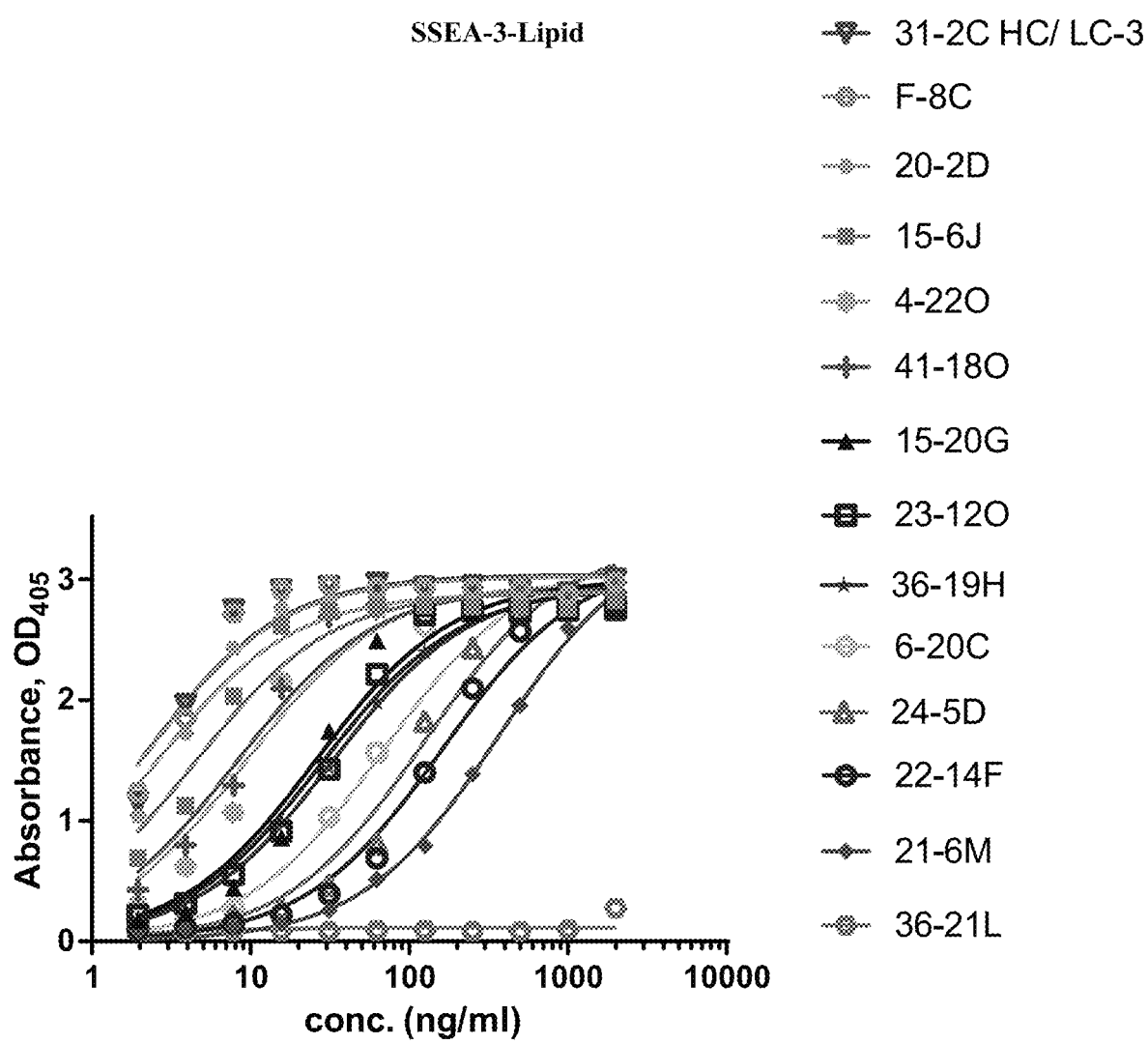
FIG. 2 shows the binding efficacy characterization between different human antibody clones by titration ELISA.
Figure 3A:
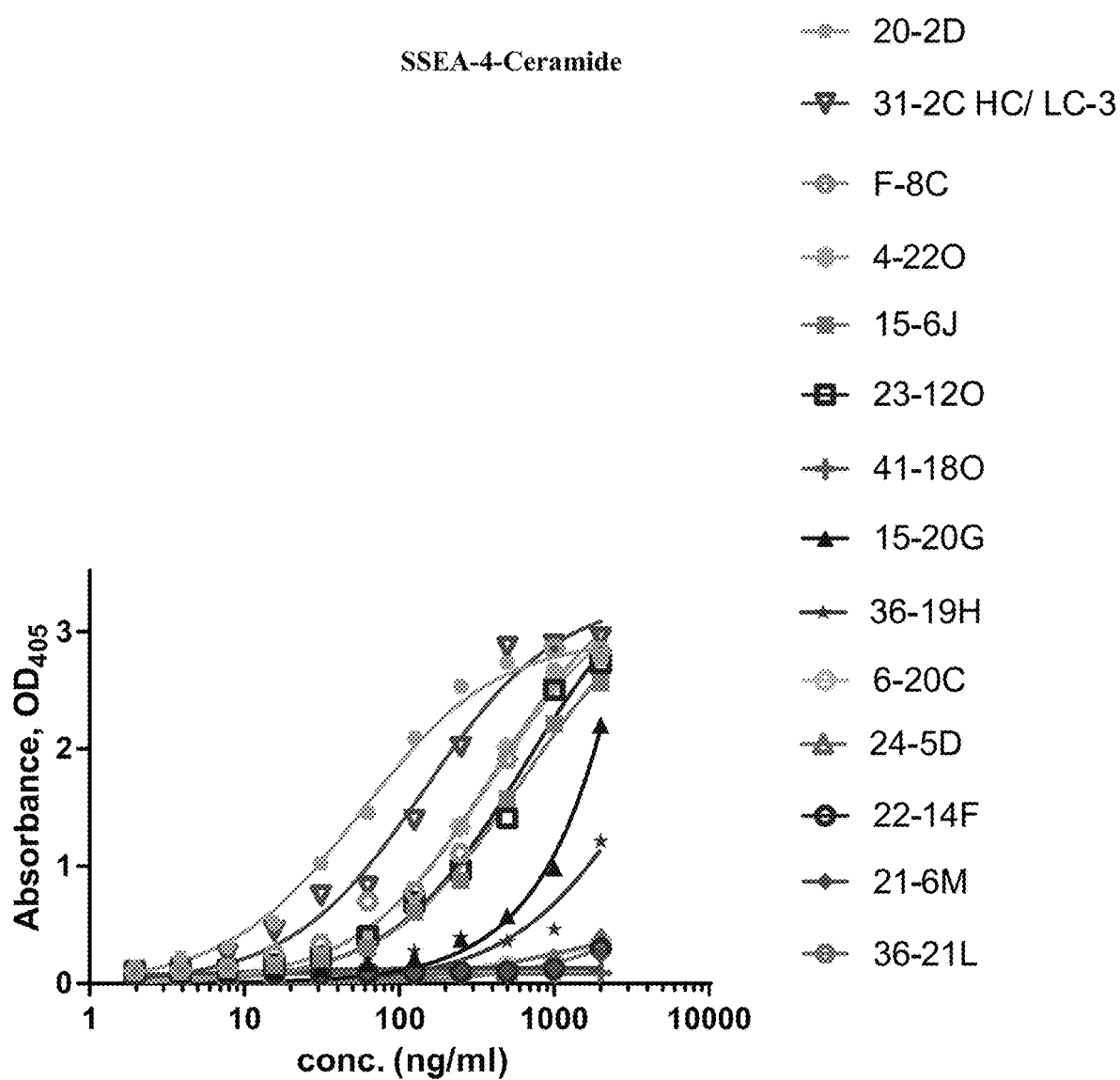
FIG. 3A uses SSEA-4-ceramide and FIG. 3B uses SSEA-4-lipid as the coating antigens.
Figure 3B:
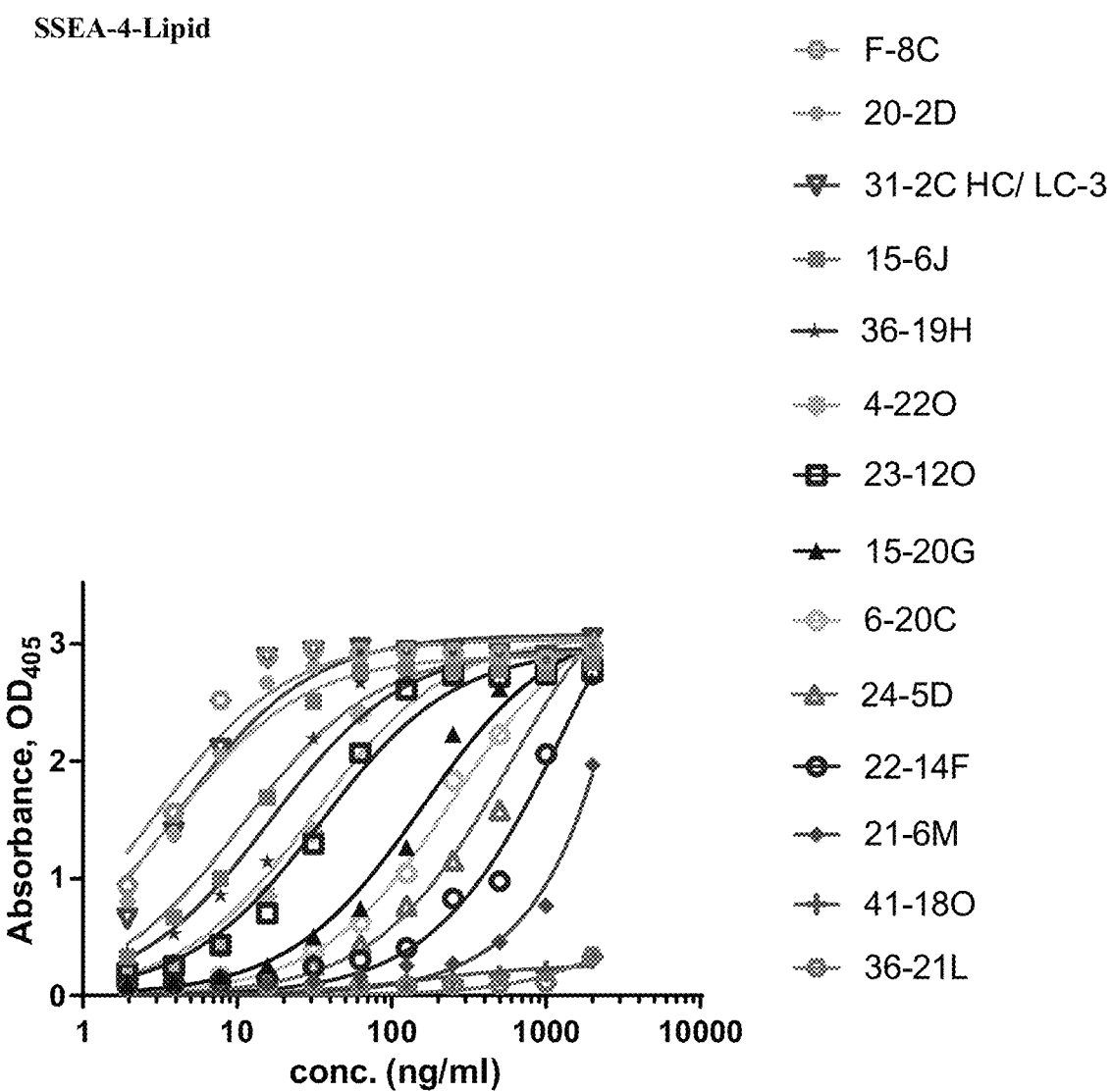
FIG. 3 shows the binding efficacy characterization between different human antibody clones by titration ELISA.

FIG. 1 indicated 20-2D, 31-2C and 4-22O had better binding affinity to Globo H. FIG. 2 indicated 20-2D, 31-2C and F-8C had better binding affinity to SSEA-3. Similarly, FIG. 3 indicated 20-2D, 31-2C and F-8C had better binding affinity to SSEA-4. Furthermore, the overall binding affinity of Globo series antigens (Globo H, SSEA-3 and SSEA-4) conjugated lipids were higher than conjugated ceramides. The following table showed the Kd value of human antibody clones binding to Globo series antigens (Globo H, SSEA-3 and SSEA-4).

TABLE 29

The exemplary kD value of human antibodies to Globo H-ceramide and Globo H-lipid

| Human Antibody | Globo H-ceramide | Globo H-Lipid |
|---|---|---|
| 20-2D | 1.7E−08M | 2.7E−09M |
| 31-2C | 1.7E−08M | 1.3E−09M |
| 4-22O | 7.0E−08M | 3.6E−08M |
| 15-6J | 6.6E−08M | 3.3E−09M |
| 23-12O | 8.1E−08M | 2.7E−08M |
| 36-19H | 9.9E−08M | 1E−09M |
| 15-20G | 1.6E−07M | 1.8E−08M |
| F-8C | 6.1E−07M | 2.0E−09M |
| 21-6M | 3.8E−07M | 5.8E−09M |
| 24-5D | 4.6E−07M | 1.33E−08M |

TABLE 30

The exemplary kD value of human antibodies to SSEA-3-ceramide and SSEA-3-lipid

| Human Antibody | SSEA-3-ceramide | SSEA-3-Lipid |
|---|---|---|
| 20-2D | 2.0E−08M | 2.4E−09M |
| 31-2C | 1.6E−08M | 2.1E−09M |
| 4-22O | 3.3E−08M | 9.2E−09M |
| 15-6J | 8.8E−08M | 4.3E−09M |
| 23-12O | 9.4E−08M | 2.7E−08M |
| 36-19H | >2.6E−07M | 3.2E−08M |
| 15-20G | 2.6E−07M | 2.5E−08M |
| F-8C | 2.6E−08M | 2.1E−09M |
| 21-6M | >2.6E−07M | 3.7E−07M |
| 24-5D | >2.6E−07M | 1.2E−07M |

TABLE 31

The exemplary kD value of human antibodies to SSEA-4-ceramide and SSEA-4-lipid

| Human Antibody | SSEA-4-ceramide | SSEA-4-Lipid |
|---|---|---|
| 20-2D | 5.2E−08M | 3.6E−09M |
| 31-2C | 2.2E−08M | 4.0E−09M |
| 4-22O | 4.4E−08M | 3.1E−09M |
| 15-6J | 7.0E−08M | 4.3E−09M |
| 23-12O | 1.2E−07M | 1.1E−08M |
| 36-19H | >1.2E−07M | 1.6E−08M |
| 15-20G | >1.2E−07M | 1.6E−07M |
| F-8C | 8.8E−08M | 2.9E−09M |
| 21-6M | >1.2E−07M | >5.7E−07M |
| 24-5D | >1.2E−07M | 5.7E−07M |

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

LISTING OF THE SEQUENCES

| SEQ ID NO | DESCRIPTION | SEQUENCE |
|---|---|---|
| 1 | 2-8M VH NUCLEOTIDE SEQUENCE | CAGCTGCAGTTGCAGGAGTCGGGCCCAGGACTGGT GAAGCCTGCGGAGACCCTGTCCCTCACCTGCTCTGT CTCCGGTGGCTACGTCACCATCAAGGATAATTATTG GGTCTGGTTCCGCCAGTCCCCAGGGAAGGAGCCGG AGTGGATTGGGAGTATGTCTTATAGTGGGAATGCCT ACTACAACCCGTCCCTCAAGAGTCGAGCCAGCATTT CCATAGACCGGTACAGGAACCAGTTCTCCCTGAGGT TGACTTCTGTGACCGCCGCAGACACGTCCATGTACT ACTGTGCGAGACGATCAGCAGCAGCTGGTGGGGGG AATGAATGGTTCGACCCCTGGGGCCAAGGAGCCCTT GTCACCGTCTCCTCA |
| 2 | 2-8M VL NUCLEOTIDE SEQUENCE | CAGTCTGCTTTGACGCAGCCGCCCTCAGTGTCTGCG GCCCCAGGACGGAAGGTCGACATCTCCTGCTCTGGA AGCACCTTCAATATTGGGAACAATTATGTGTCGTGG TACCGGCAGTTCCCAGGAACAGCCCCCAAACTCCTC |

| SEQ ID NO | DESCRIPTION | SEQUENCE |
|---|---|---|
| | | ATTTATGACAATGATAAGCGACCCTCAGGCATTCCT GACCGATTCTCTGGCTCCAGGTTCGGCACGTCAGCC ACCCTGGGCATCACCGGACTCCAGACTGACGACGA GGCCATTTATTACTGCGCAACATGGGATAACAGACT GGATGCTGTGGTTTTCGGCGGGGGGACCGAGTTGAT CGTCCTT |
| 3 | 2-8M VH AMINO ACID SEQUENCE | QLQLQESGPGLVKPAETLSLTCSVSGGYVTIKDNYWV WFRQSPGKEPEWIGSMSYSGNAYYNPSLKSRASISIDR YRNQFSLRLTSVTAADTSMYYCARRSAAAGGGNEWF DPWGQGALVTVSS |
| 4 | 2-8M VL AMINO ACID SEQUENCE | QSALTQPPSVSAAPGRKVDISCSGSTFNIGNNYVSWYR QFPGTAPKLLIYDNDKRPSGIPDRFSGSRFGTSATLGIT GLQTDDEAIYYCATWDNRLDAVVFGGGTELIVL |
| 5 | 6-8N VH NUCLEOTIDE SEQUENCE | GAGGTGCACCTGGTGGAGTCTGGGGGAGGCCTGGT AAACCCGGGGGGGTCCCTTAGACTCTCCTGTTCAGC CTCTGGCTTCGCTTTCACTACCGCCTGGATGACCTGG GCCCGCCAGGCTCCAGGGAAGGGACTGGAATGGAT TGGCCTTATTAAAAGCACAAATGATGGTGGGTCTAT AGACTACGCTGCACCCGTGCAAGGCAGATTCACCAT CTCAAGAGATGATTCAAAGAACACGATTTACCTCCA AATGAGCAGCCTCAAAGCCGAGGACTCAGCCGTCT ACTATTGTGCCACAAACGATGTTGTTCGGCTTCGAG GGGTTACCCCCCCCATACTTCTGTGGGGCCAGGGGA CCCTGATCACCGTCTCCTCA |
| 6 | 6-8N VL NUCLEOTIDE SEQUENCE | CAGCTTGTACTGACTCAATCGCCCTCAACCTCTGCCT CCCTGGGAGCCCCGGTCACACTCACCTGCACTCTGA GCAGTGGGCACCACAGCTACCCCGTCGCATGGCATC AGAAGCACCCAGAGAAGGGCCCTCGATACTTGATG AAGATTAACGGAGATGGCAGCCACACCAAGGGGGA CGGTATCCCTGATCGCTTCTCAGGCTCCAGCTCTGG GACTGGGCGCTATCTCACCATCTCCAGCCTCCAGTC TGAGGATGAGGCTGACTATTACTGTCAGACCTGGGC CACTGGATGGGTGTTCGGCGGAGGGACCAAACTGA CCGTCCTA |
| 7 | 6-8N VH AMINO ACID SEQUENCE | EVHLVESGGGLVNPGGSLRLSCSASGFAFTTAWMTW ARQAPGKGLEWIGLIKSTNDGGSIDYAAPVQGRFTISR DDSKNTIYLQMSSLKAEDSAVYYCATNDVVRLRGVTP PILLWGQGTLITVSS |
| 8 | 6-8N VL AMINO ACID SEQUENCE | QLVLTQSPSTSASLGAPVTLTCTLSSGHHSYPVAWHQ KHPEKGPRYLMKINGDGSHTKGDGIPDRFSGSSSGTGR YLTISSLQSEDEADYYCQTWATGWVFGGGTKLTVL |
| 9 | 2-20G VH NUCLEOTIDE SEQUENCE | GAGTTGCAGTTGGTGGAGTCTGGGGGAAAGTTGGTA AATCCGGGGGGGTCCCTGAGACTCTCATGTGCAGCC TCTGGATTCACTTTCCCTAACGCCTGGTTTAACTGGG TCCGCCAGACTCCAGGGAGGGGGCTGGAGTGGGTT GCCCGTATTAAAAGTCATTCTGACGGTGGGACAGCC GACTACGCTGCACCCGTGAAAGGCAGATTCACCGTC TCAAGGGATGATTCAGAGAACATGGTGTTTCTGCAA ATGAACCGCCTGCGTGCCGAGGACACAGCCGTTTAT TATTGTACTACCTTGGAGATTTATCACCCTGTGGAC GTCTGGGGCCAGGGGACCACGGTCGCCGTCTCCTCA |
| 10 | 2-20G VL NUCLEOTIDE SEQUENCE | GATGTTGTGCTGACTCAGTCTCCACTCTCCCTGTCCG TCACCCTTGGACAGCCGGCCTCCATCTCCTGCAGGT CCAGTCACAGCCTCCCAAGAGATGATGAATACTCCT ACCTGAATTGGTTTCAGCAGAGGCCAGGCCAGTCTC CAAGGCGCCTAATTTATAGGGTTTCTAAGCGGGACT CTGGGGTCCCAGACAGATTCAGCGGCAGTGGGTCA GACACTTATTTCACACTGACAATCAGCAGGGTGGAG GCTGAGGATGTTGGAGTTTATTACTGCATGCAAGGT ACATACTGGCCCGGGACGTTCGGCCAAGGGACGAA GTTGGAAATCGAGCGA |
| 11 | 2-20G VH AMINO ACID SEQUENCE | ELQLVESGGKLVNPGGSLRLSCAASGFTFPNAWFNWV RQTPGRGLEWVARIKSHSDGGTADYAAPVKGRFTVSR DDSENMVFLQMNRLRAEDTAVYYCTTLEIYHPVDVW GQGTTVAVSS |

-continued

| SEQ ID NO | DESCRIPTION | SEQUENCE |
|---|---|---|
| 12 | 2-20G VL AMINO ACID SEQUENCE | DVVLTQSPLSLSVTLGQPASISCRSSHSLPRDDEYSYLN WFQQRPGQSPRRLIYRVSKRDSGVPDRFSGSGSDTYFT LTISRVEAEDVGVYYCMQGTYWPGTFGQGTKLEIER |
| 13 | 3-17I VH NUCLEOTIDE SEQUENCE | GAGGTGCACCTGGTGGAGTCTGGGGGAGGCCTCGT AAACCCGGGGGGGTCCCTTAGACTCTCCTGTACAGC CTCTGGATTCACTTTCATCACCGCCTGGATGACCTG GGCCCGCCAGGCTCCAGGGAGGGGCTGGAGTGGA TTGGACTTATTAAAAGCGGAAATGATGGTGGGGCTA TAGAGTACGCTGCACCCGTGAAAGGCAGATTCACCA TCTCAAGAGATGATTCAAGGAATATGATTTATCTAC AAATGAATAATGTCAAAGCCGAGGACGCAGCCGTC TACTATTGTGCCACAAACGATGTTGCTTTGGTTTGG GGAGTTACCCCCCCCTTGCTTCTCTGGGGCCAGGGG ACCCGGGTCACCGTCTCTTCA |
| 14 | 3-17I VL NUCLEOTIDE SEQUENCE | CAACTTGTGGTGACTCAATCGCCCTCTGCCTCTGCCT CCCTGGGAGGCTCGGTCAAGCTCACCTGCACTCTGA GCAGTGGGCACGGCAACTACCCCGTCGCATGGCATC AGCTCCACCCAGCGAAGGGCCCTCGATACTTGATGA AGCTTAATGCAGATGGCAGCCACATCAAGGGGGCC GGGATCACTGATCGCTTCTCAGGCTTCAGGTCTGGG GCTGAGCGCTACCTCACCATCTCCAGCCTCCAGTCT GAAGATGAGGCTGATTATTACTGTCAGACCTGGGCC CCTGGATGGGTGCTCGGCGGAGGGACCAAGCTGAC CGTCCTA |
| 15 | 3-17I VH AMINO ACID SEQUENCE | EVHLVESGGGLVNPGGSLRLSCTASGFTITAWMTWA RQAPGRGLEWIGLIKSGNDGGAIEYAAPVKGRFTISRD DSRNMIYLQMNNVKAEDAAVYYCATNDVALVWGVT PPLLLWGQGTRVTVSS |
| 16 | 3-17I VL AMINO ACID SEQUENCE | QLVVTQSPSASASLGGSVKLTCTLSSGHGNYPVAWHQ LHPAKGPRYLMKLNADGSHIKGAGITDRFSGFRSGAE RYLTISSLQSEDEADYYCQTWAPGWVLGGGTKLTVL |
| 17 | B-21J VH NUCLEOTIDE SEQUENCE | CAGGTGCAACTGGTGGAGTGGGGGGGAGGCGTGGC CCAGCCTGGGACGTCCCTGAGGCTCACCTGTGATGC GTCTGGATTCAGCTTCAGACATTATGGCATGCACTG GGTCCGCCAGGCTCCAGGCAAGGGGCTGGAGTGGG TGGCAGTTATCTGGCATAATGGAAGAGACAGAGAG TATGCAGACTCCGTGAAGGGCCGCTTCACCATCTCC AGAGACAATTCCAAGTACACCCTGTCTTTACAAATG AACAGCCTGACAGTCGAAGACACGGCATTATATTAC TGCGGGAGAGATCGAGGTGAAGACGAGCCGATTGA CTTTTGGGGCCAGGGAACCCTGGTCACCGTCTCTTC A |
| 18 | B-21J VL NUCLEOTIDE SEQUENCE | CAGGCTGTGCTGACTCAACCGTCTTCCCTCTCTGCAT CTCCTGGAGCATCAGCCAGTCTCACCTGCACCTTGC GCAGTGGCCTCAGTGCTGGTCCCAAGTGGATATACT GGTACCAGCAGAGGGCAGGGAGTCCTCCCCAATTTC TCCTGACATACAAATCAGACTCAGAAGAGCGGCGG AGCTCTGGACTCCCCAGCCGCTTCTCTGGATCCAAG GATGGCTCGGCCAATGCAGGGATTTTACTCATCTCT GGGCTCCAATCTGAAGATGAGGCAGACTATTACTGT GCGATTTGGCACAGCAACGTTGTCTTTTTCGGCGCA GGGACCAGGTTGACCGTCCTG |
| 19 | B-21J VH AMINO ACID SEQUENCE | QVQLVEWGGGVAQPGTSLRLTCDASGFSFRHYGMHW VRQAPGKGLEWVAVIWHNGRDREYADSVKGRFTISR DNSKYTLSLQMNSLTVEDTALYYCGRDRGEDEPIDFW GQGTLVTVSS |
| 20 | B-21J VL AMINO ACID SEQUENCE | QAVLTQPSSLSASPGASASLTCTLRSGLSAGPKWIYWY QQRAGSPPQFLLTYKSDSEERRSSGLPSRFSGSKDGSA NAGILLISGLQSEDEADYYCAIWHSNVVFFGAGTRLTV L |
| 21 | F-18D VH NUCLEOTIDE SEQUENCE | GAGGTGCGCCTGGTGGAGTCTGGGGGAGGCTTAAT AGAGCCGGGGGGTCTCTTAGACTCTCATGTGAAGC CTCTGGATTCGTTTTCACTACCGCCTGGATGAATTGG GTCCGCCAGGCTCCAGGGAAGGGGCTGGAGTGGGT |

| SEQ ID NO | DESCRIPTION | SEQUENCE |
|---|---|---|
| | | TGGCCGTATTAAGAGCAAAAATGAGGCTGAGACAA CAGACTACGCTGCACCCGTGAAAGGCAGATTCACCA TCTCAAGAGATGATTCAAAGGACACATTGTATCTGC AAATGAACAACCTGAAAACCGAAGACACAGCCGTC TATTATTGTACCACACTTGAGACGTATTACGAGTCC GACTTCTGGGGCCAGGGAGTCCTGGTCGCCGTCTCC TCA |
| 22 | F-18D VL NUCLEOTIDE SEQUENCE | GATGTTGTGATGACTCAGTCTCCACTCTCCCTGACC GTCACTCTTGGACAGCCGGCCTCCATCTCCTGCAGG TCTAGTCAAAGCCTCGCAGAGAGAGAAGAGGACAT CTTGTTAAACTGGTATCACCAGGGGCCAGGCCAATC TCCCAGGCGCCTAATTTATAGAGTTTCTAAGCGTGA GTCTGGGGTCCCAAATAAATTCAGCGGCAGTGTGTC AGGCACTGATTTCACCCTGAGAATCAGCAGGGTGGA GGCTGAGGATGTTGGGGTTTATTACTGCATGCAACG AACACACTGGCCTCAGACTTTTGGCCAGGGGACCAA GCTGGAGATCAGACGA |
| 23 | F-18D VH AMINO ACID SEQUENCE | EVRLVESGGGLIEPGGSLRLSCEASGFVFTTAWMNWV RQAPGKGLEWVGRIKSKNEAETTDYAAPVKGRFTISR DDSKDTLYLQMNNLKTEDTAVYYCTTLETYYESDFW GQGVLVAVSS |
| 24 | F-18D VL AMINO ACID SEQUENCE | DVVMTQSPLSLTVTLGQPASISCRSSQSLAEREEDILLN WYHQGPGQSPRRLIYRVSKRESGVPNKFSGSVSGTDFT LRISRVEAEDVGVYYCMQRTHWPQTFGQGTKLEIRR |
| 25 | J-5N VH NUCLEOTIDE SEQUENCE | CAGGTGCAGCTGGTGGAGTGGGGGGGAGGCGTGGT CCAGCCTGGGGGGTCCCTGAGACTTTGCTGTGCAGC GTCTGGATTCAGTTTAAGGAGTTTTGGCATGCACTG GGTCCGTCAGGCTCCAGGCAAGGGGCTGGAATGGG TGGCAGTTATTTGGCCCCGACGAAGTCAAATACAAT ATGCAGACTCCGTGAAGGGCCGAGTCACCATCTCCA GAGACGACTCTAGGAGTACGGTATGTCTGCAGATGA ACAGCCTGAGAGTCGAGGACACGGCTCTCTATCGCT GTGCGAGAGACCCCGGTGAGGACAATCCCATAGAT TACTGGGGCCAGGGAACCCTGGTCATCGTCTCCTCA |
| 26 | J-5N VL NUCLEOTIDE SEQUENCE | CAGGCTGTGCTGACTCAGCCGTCTTCCCTCTCTGCAT CTCCTGGAGCATCAGCCAGTCTCACCTGCACCTTCC TCAGCGGCATCAATGTTGGTCCCTACTGGATATACT GGTACCAGCAAAAGCCAGGGAGTCCTCCCCAGTTTC TCCTGAGGTACAAGTCAGACTCAGATAAGCACCAG GGCTCTGAAGTCCCCAGCCGCTTCTCTGGATCCAAA GATGCTTCGGCCAATGCAGGGATTTTACTCATCTCT GGGCTCCAGTCTGAAGATGAGGCTGACTATTACTGT ATGATCTGGCACGTCAGCGGTGTGATTTTCGGCGGA GGGACCAAGCTGACCGTCCTA |
| 27 | J-5N VH AMINO ACID SEQUENCE | QVQLVEWGGGVVQPGGSLRLCCAASGFSLRSFGMHW VRQAPGKGLEWVAVIWPRRSQIQYADSVKGRVTISRD DSRSTVCLQMNSLRVEDTALYRCARDPGEDNPIDYWG QGTLVIVSS |
| 28 | J-5N VL AMINO ACID SEQUENCE | QAVLTQPSSLSASPGASASLTCTFLSGINVGPYWIYWY QQKPGSPPQFLLRYKSDSDKHQGSEVPSRFSGSKDASA NAGILLISGLQSEDEADYYCMIWHVSGVIFGGGTKLTV L |
| 29 | J-8G VH NUCLEOTIDE SEQUENCE | CAGGTGCAACTGGTGGAGTGGGGGGGAGGCGTGGT CCAGCCTGGGACGTCCCTGAGACTCACCTGTGATGC GTCTGGATTCAGCTTCAGACATTATGGCATGCACTG GGTCCGCCAGGCTCCAGGCAAGGGGCTGGAGTGGG TGGCAGTTATCTGGCATAATGGAAGAGATAAAGACT ATGCAGACTCCGTGAAGGGCCGGTTCACCATCTCCA GAGACAATTCCAAGTACACCCTGTCTTTACAAATGA ACAGCCTGACAGTCGAGGACACGGCATTATATTACT GTGGGAGAGATCGAGGTGAAGACGAGCCGATTGAC TTTTGGGGCCAGGGAACCCTGGTCACCGTCTCCTCA |
| 30 | J-8G VL NUCLEOTIDE SEQUENCE | CAGGCTGTGCTGACTCAACCGTCTTCCCTCTCTGCAT CTCCTGGAGCATCAGCCAGTCTCACCTGCACCTTGC GCAGTGGCCTCAATGTTGGTCCCTACTGGATATACT |

LISTING OF THE SEQUENCES

| SEQ ID NO | DESCRIPTION | SEQUENCE |
|---|---|---|
|  |  | GGTACCAGCAGAAGGCAGGGAGTCCTCCCCAATTTC TCCTGAGATACAAATCAGACTCAGAAAAGCGGCGG AGCTCTGGAGTCCCCAGCCGCTTCTCTGGATCCAAA GATGCCTCGGCCAATGCAGGGATTTTACTCATCTCT GGGCTCCAGTCTGAAGATGAGGCTGACTATTATTGT GCGATTTGGCACAGCAATGCTGTCTTTTTCGGCGCA GGGACCAAGTTGACCGTCCTA |
| 31 | J-8G VH AMINO ACID SEQUENCE | QVQLVEWGGGVVQPGTSLRLTCDASGFSFRHYGMHW VRQAPGKGLEWVAVIWHNGRDKDYADSVKGRFTISR DNSKYTLSLQMNSLTVEDTALYYCGRDRGEDEPIDFW GQGTLVTVSS |
| 32 | J-8G VL AMINO ACID SEQUENCE | QAVLTQPSSLSASPGASASLTCTLRSGLNVGPYWIYW YQQKAGSPPQFLLRYKSDSEKRRSSGVPSRFSGSKDAS ANAGILLISGLQSEDEADYYCAIWHSNAVFFGAGTKLT VL |
| 33 | 4-220 VH NUCLEOTIDE SEQUENCE | CAGGTGCAGATGGTGGAGTTTGGGGGAGGCATCTTC CAGCCTGGGGGGTCCCTGAGACTCTCCTGTGTCGCG TCTGGATTCCCCTTCAGGTACTATGGTTTCCACTGGG TCCGCCAGACTCCAGGCAAGGGGCTGGAGTGGCTG GCAGTTGTATGGCACAATGGAAGGGAGACATATTAT GAAGACTCCGTGAAGGGGCGATTCACCATCTCCAGA GACAATTACAAGAACACGCTGTATTTGCAAATGGAC AGCCTGAGAGTCGAGGACACGGCTGTCTATCACTGT GCGAGAGATCGTGGTAGCGACGAACCAATTGACTA CTGGGGCCAGGGAGTTTTGGTCACCGTCTCCTCA |
| 34 | 4-220 VL NUCLEOTIDE SEQUENCE | CAGGCTGTGCTGACTCAGCCGTCCTCCCTCTCTGCAT CTCCTGGAGCATCAGCCAGTATCACCTGCACCTTAC GCAGTGACCTCACTGTTGGTCCCTACTGGATGTACT GGTACCAACAGAAGCCAGGGAGTCCTCCCCAATTTC TCCTGAGGTACAAGTCAGACTCCGAAAAGTATCAGG GCTCTGGAGTCCCCAGCCGCTTCTCTGGATCCAAAG ACGCTTCGGCCAATGCAGGGACTTTGCTCATCTCTG GACTCCAGTCTGAAGATGAGGCTGACTATTACTGTC AGACTTGGCACGCCAACACTGTGGTATTTGGCGGAG GGACCAAGCTGACCGTCCTA |
| 35 | 4-220 VH AMINO ACID SEQUENCE | QVQMVEFGGGIFQPGGSLRLSCVASGFPFRYYGFHWV RQTPGKGLEWLAVVWHNGRETYYEDSVKGRFTISRD NYKNTLYLQMDSLRVEDTAVYHCARDRGSDEPIDYW GQGVLVTVSS |
| 36 | 4-220 VL AMINO ACID SEQUENCE | QAVLTQPSSLSASPGASASITCTLRSDLTVGPYWMYW YQQKPGSPPQFLLRYKSDSEKYQGSGVPSRFSGSKDAS ANAGTLLISGLQSEDEADYYCQTWHANTVVFGGGTK LTVL |
| 37 | 6-20C VH NUCLEOTIDE SEQUENCE | CAGGTGCAGCTGGTGGAGTCTGGGGGAGGCGTCTTC CAGCCGGGGGGGTCCCTGAGACTCTCCTGTGCAGCG TCTGGATTCAGTTTCAGGAGATTTGGTATGCATTGG GTCCGCCAGGCTCCAGGCAAGGGGCTGGAGTGGCT GGCAGTTGTTTGGCATGATGGAAGGGAGACACACT ATGGAGACTCCGTGAGGGGCCGATTCACCATCTCCA GAGACAACTCCATGCACATGGTGTTTTTGGACATGT ACAGCCTGAGGGTCGAGGACACGGCTCTATATCGCT GTGCGAGAGATCCTGGTCAGGACGAAGCCATTGACT ATTGGGGCCAGGGAGTCCTGGTCACCGTCTCGTCA |
| 38 | 6-20C VL NUCLEOTIDE SEQUENCE | CAGGCTGTGCTGACTCAGCCGTCTTCCCTCTCTGCAT CTCCTGGAGCATCAGCCAGTCTCACCTGCACCTTAC ACAGTGGCCTCACTGTTGGTCCCTATTGGATATACT GGTTCCGGCAGAAGCCAGGGAGTCCCCCCCAGTTTC TCCTCAGGTACAAATCCGACTCAGAGGAGTACCGTG CCTCTGGAGTCCCCAGCCGCTTCTCTGGATCCAAAG ATGCTTCGGCCAACTCAGGCATTTACTCATCTCTGG ACCACAGTCTGAAGACGAGGCTGACTATTACTGTAT GACTTGGCACACCAACAAGGTAGTCTTCGGCGGAG GGACCACACTGACCGTCCTA |

-continued

| SEQ ID NO | DESCRIPTION | SEQUENCE |
|---|---|---|
| 39 | 6-20C VH AMINO ACID SEQUENCE | QVQLVESGGGVFQPGGSLRLSCAASGFSFRRFGMHWV RQAPGKGLEWLAVVWHDGRETHYGDSVRGRFTISRD NSMHMVFLDMYSLRVEDTALYRCARDPGQDEAIDYW GQGVLVTVSS |
| 40 | 6-20C VL AMINO ACID SEQUENCE | QAVLTQPSSLSASPGASASLTCTLHSGLTVGPYWIYWF RQKPGSPPQFLLRYKSDSEEYRASGVPSRFSGSKDASA NSGILLISGPQSEDEADYYCMTWHTNKVVFGGGTTLT VL |
| 41 | 12-14G VH NUCLEOTIDE SEQUENCE | CAGGTGCAGCTGGTGCAGTCTGGGGCTGAGGTGAA GAAGCCTGGGGCCTCAGTGAAGGTCTCCTGCCAGGC TTCTGGATACACCTTCACCAACTATGGTGTCAACTG GGTGCGACAGGCCACTGGACAAGGGCTTGAGTGGA TGGGATGGATGAACACTAACAGTGGTGACACGGGT TATGCCCAGAAGTTCCAGGGCAGAGTCACCATGACC AGGGACACCTCCATAAACACAGCCTACATGGAGCT GAGCGGACTGACATCTGAGGACACGGCCGTCTATTA CTGTGCGCGAGCGTATTTTTTTGATTCGTGGAATAA GGGCAACTGGTTCGACCCCTGGGGCCAGGGAACCC CGGTCACCGTCTCCTCA |
| 42 | 12-14G VL NUCLEOTIDE SEQUENCE | CAGTCTGTGCTGACTCAGGCACCCTCAGTGTCTGGG ACCCCCGGGCAGAGGGTCACCATCTCTTGTTCTGGA GGCAGCTCCAACCTGGGAAGAAGTTATATATATTGG TACCAACAGTTCCCAGGAACGGCCCCCAGAGTCCTC ATTTATAAAAATAGTCAGCGGCCCTCAGGGGTCCCT GACCGATTCTCCGGCTCCAAGTCTGGCACCTCAGCC TCCCTGGCCATCAGTGGGCTCCGGTCCGAGGATGAG GCTCATTATTACTGTGCAGCATGGGATGACAGCCTG AGTGGGTCTTGGGTGTTCGGCGGAGGGACCAAGCTG ACCGTCCTA |
| 43 | 12-14G VH AMINO ACID SEQUENCE | QVQLVQSGAEVKKPGASVKVSCQASGYTFTNYGVNW VRQATGQGLEWMGWMNTNSGDTGYAQKFQGRVTM TRDTSINTAYMELSGLTSEDTAVYYCARAYFFDSWNK GNWFDPWGQGTPVTVSS |
| 44 | 12-14G VL AMINO ACID SEQUENCE | QSVLTQAPSVSGTPGQRVTISCSGGSSNLGRSYIYWYQ QFPGTAPRVLIYKNSQRPSGVPDRFSGSKSGTSASLAIS GLRSEDEAHYYCAAWDDSLSGSWVFGGGTKLTVL |
| 45 | 15-6J VH NUCLEOTIDE SEQUENCE | CAGGTGCAGTTGGTGGAGTTTGGGGGAGGCATTTTC GAGCCTGGGGGGTCCCTGAGACTCTCCTGTGTCGCG TCTGGATTCTCCTTCAGGCATTATGGTATGCACTGG GTCCGCCAGGCTCCAGGCAAGGGGCTGGAGTGGCT GGCAGTTGTATGGCATGATGGAAGGGAGACACATT ATGGAGACTCCGTGAAGGGGCGATTCACCATCTCCA GAGACAATTACAAGAATACGCTGTTTTTGCAAATGG ACAGCCTGAGAGTCGAGGACACGGCTGTCTATCACT GTGCGAGAGATCGTGGTAGCGACGAACCTATTGACT ACTGGGGCCAGGGAGTTTTGGTCACCGTCTCCTCA |
| 46 | 15-6J VL NUCLEOTIDE SEQUENCE | CAGGCTGTGCTGACTCAGCCGTCCTCCCTCTCTGCAT CTCCTGGAGCATCAGCCAGTATCACCTGCACCTTAC GCAGTGACGTCACTGTTAGTCCCTGGACATACTGGT ACCAACAGAAGCCAGGGAGTCCTCCCCGATTTCTCC TGAGATACAAATCAGACTCTGATAAGTATCAGGGCT CTGGAGTCCCCAGCCGCTTCTCTGGATCCAAAAATG CTTCGGCCAATGCAGCGATTTTACTCATCTCTGGGCT CCAGTCTGAAGATGAGGCTGACTATTACTGTCAGAC TTGGCACACCACCACTGTGGTATTTGGCGGAGGGAC CAAGCTGACCGTCCTA |
| 47 | 15-6J VH AMINO ACID SEQUENCE | QVQLVEFGGGIFEPGGSLRLSCVASGFSFRHYGMHWV RQAPGKGLEWLAVVWHDGRETHYGDSVKGRFTISRD NYKNTLFLQMDSLRVEDTAVYHCARDRGSDEPIDYW GQGVLVTVSS |
| 48 | 15-6J VL AMINO ACID SEQUENCE | QAVLTQPSSLSASPGASASITCTLRSDVTVSPWTYWYQ QKPGSPPRFLLRYKSDSDKYQGSGVPSRFSGSKNASAN AAILLISGLQSEDEADYYCQTWHTTTVVFGGGTKLTV L |

LISTING OF THE SEQUENCES

| SEQ ID NO | DESCRIPTION | SEQUENCE |
|---|---|---|
| 49 | 18-11C VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACACTTTCACCAGCTTTGGTATCAACTGG GTGCGACAGGCCCCTGGACAAGGGCTTGAGTGGAT GGGATGGATGAACTCCAACAGTGGTGATGCGGACT CTGCACAGAAGTTCCAGGGCAGACTCACTATGACCA CCGACACCTCCACAAGTACAGCCTACATGGAGCTGA GGAATCTGAGATCTGAGGACACGGCCGTATATTATT GCGCGAGAATGAATTTCCGTGGTTCGAAGTGGGAG GTGAACTGGTTCGACCCCTGGGGCCAGGGAACCCTG ATCACCGTCTCCTCA |
| 50 | 18-11C VL NUCLEOTIDE SEQUENCE | CAGTCTGTGGTGACTCAGCCACCCTCAGCGTCTGGG ACCCCCGGGCAGAGGGTCACCATCTCCTGTTCTGGA AGCAGGTCCAACGTCGAAAGAAATTTTGTTTACTGG TACCAGCAACTCCCAGGAACGGCCCCCAAACTTCTC ATCTATATGAACAGTCAGCGGCCCTCAGGGGTCCCT GACCGATTCTCTGGCTCTCGTTCTGGCACCTCAGCCT CCCTGGCCATCACTGGGCTTCGGTCCGAGGATGAGG CTGACTATTATTGTGCAACTTGGGATGACAATCTGA GAGGCTGGGTGTTCGGCGGAGGGACCAAGGTGACC GTCCTA |
| 51 | 18-11C VH AMINO ACID SEQUENCE | QVQLVQSGAEIKRPGASVKVSCKASGYTFTSFGINWV RQAPGQGLEWMGWMNSNSGDADSAQKFQGRLTMTT DTSTSTAYMELRNLRSEDTAVYYCARMNFRGSKWEV NWFDPWGQGTLITVSS |
| 52 | 18-11C VL AMINO ACID SEQUENCE | QSVVTQPPSASGTPGQRVTISCSGSRSNVERNFVYWYQ QLPGTAPKLLIYMNSQRPSGVPDRFSGSRSGTSASLAIT GLRSEDEADYYCATWDDNLRGWVFGGGTKVTVL |
| 53 | 20-2D VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACACCTTCACCAGGTTCGGCATCAACTGG GTGCGACAGGCCCCTGGACAAGGGCTTGAGTGGAT GGGATGGATGAACTCCAACAGTGGTAATGCGGACT CTGCACAGAAGTTCCAGGGCAGACTCACTATGACCA CCGACACCTCCACAAGTACAGCCTACATGGAGCTGA GGAATCTAAGATCTGAGGACACGGCCGTATATTATT GCGCGAGAATGAATTACCGTGGTTCGAAGTGGGAA ATAAACTGGTTCGACCCCTGGGGCCAGGGAACCCTG ATCACCGTCTCCTCA |
| 54 | 20-2D VL NUCLEOTIDE SEQUENCE | CAGTCTGTGGTGACTCAGCCACCCTCAGCGTCTGGG ACCCCCGGGCAGAGGGTCACCATTTCCTGTTCTGGT AGCAGGTCCAACGTCAAAGAAATTTTGTTTACTGG TACCAGCAGCTCCCAGGAACGGCCCCCAAACTTCTC ATCTATATGAACAATAACCGCCCCTCAGGGGTCCCT GACCGATTCTCTGGCTCTCATTCTGGCACCTCAGCCT CCCTGGCCATCACTGGGCTTCGGTCCGAGGATGAGG CTGATTATTATTGTGCTACTTGGGATGACAATCTGA GAGGCTGGGTGTTCGGCGGAGGGACCAAGGTGACC GTCCTA |
| 55 | 20-2D VH AMINO ACID SEQUENCE | QVQLVQSGAEIKRPGASVKVSCKASGYTFTRFGINWV RQAPGQGLEWMGWMNSNSGNADSAQKFQGRLTMTT DTSTSTAYMELRNLRSEDTAVYYCARMNYRGSKWEI NWFDPWGQGTLITVSS |
| 56 | 20-2D VL AMINO ACID SEQUENCE | QSVVTQPPSASGTPGQRVTISCSGSRSNVQRNFVYWY QQLPGTAPKLLIYMNNNRPSGVPDRFSGSHSGTSASLA ITGLRSEDEADYYCATWDDNLRGWVFGGGTKVTVL |
| 57 | 9-5L VH NUCLEOTIDE SEQUENCE | CAGGTGCACCTGGTGGAGTCTGGGGGAGACCTGGTC CAGCCTGGGAGGTCCCTGAGACTCTCCTGTGCAGCG TCTGGATTTACCCTCAAACGTTATGGCATTCACTGG GTCCGCCAGGCGCCAGGCAAGGGGCTGGAGTGGGT GGCAGTTACTTGGCATGATGGAAATATATACTATGC AGACTCCGTGAAGGGCCGACTCACCGTCTCCAGAGA CAGTTACAAGAACACGGTGGATCTACAAATGAACA |

| SEQ ID NO | DESCRIPTION | SEQUENCE |
|---|---|---|
| | | GCCTGAAAGTCGAGGACACGGCTCTATATTACTGTG<br>CGAGAGATGCCGGGCAAAATGCGCCCATTGACCTCT<br>GGGGCCACGGAACCCTGGTCACCGTCTCCTCA |
| 58 | 9-5L VL NUCLEOTIDE SEQUENCE | CAGGCTGTACTGACTCAGCCGTCTTCCCTCTCTGCAT<br>CTCCTGGAGCATCAGCCAGTCTCACCTGCACCTTAC<br>CCAGTGGCATCAATGTTGCTACCCACTGGATATACT<br>GGTACCAGCAGAAGCCTGGCAGTCCTCCCCAGTTTC<br>TCCTGCGGTACAAATCAGACTCAGATATCCAACACG<br>GCTCTGGAGTCCCCAGCCGCTTCTCTGGATCCAAAG<br>ATGCTTCGGCCAATGCCGCGATTTTAGTCGTCTCTG<br>GTCTCCAGTCTGAGGATGAGGCTGACTATTACTGTA<br>TGATTTGGTATTCCACCGCCGTGGTTTTCGGCGGAG<br>GGACCAAGCTGACCGTCCTG |
| 59 | 9-5L VH AMINO ACID SEQUENCE | QVHLVESGGDLVQPGRSLRLSCAASGFTLKRYGIHWV<br>RQAPGKGLEWVAVTWHDGNIYYADSVKGRLTVSRDS<br>YKNTVDLQMNSLKVEDTALYYCARDAGQNAPIDLWG<br>HGTLVTVSS |
| 60 | 9-5L VL AMINO ACID SEQUENCE | QAVLTQPSSLSASPGASASLTCTLPSGINVATHWIYWY<br>QQKPGSPPQFLLRYKSDSDIQHGSGVPSRFSGSKDASA<br>NAAILVVSGLQSEDEADYYCMIWYSTAVVFGGGTKLT<br>VL |
| 61 | 15-20G VH NUCLEOTIDE SEQUENCE | CAGGTGCAGTTGGTGGAGTTTGGGGGAGGCATTTTC<br>CAGCCTGGGGGGTCCCTGAGACTCTCCTGTGTCGCG<br>TCTGGATTCTCCTTCAGGTATTATGGTTTCCACTGGG<br>TCCGCCAGGCTCCAGGCAAGGGGCTGGAGTGGCTG<br>GCAGTTGTATGGCATGATGGAAGGGAGACACATTAT<br>GGAGACTCCGTGAGGGGCGATTCACCATCTCCAGA<br>GACAATTACAAGAACACGGTGTTTTTGGAAATGGAC<br>AGCCTGAGAGTCGAGGACACGGCTGTCTATCACTGT<br>GCGAGAGATCGTGGTAGCGACGAACCTATTGACTAC<br>TGGGGCCAGGGAGTTTTGGTCACCGTCTCCTCA |
| 62 | 15-20G VL NUCLEOTIDE SEQUENCE | CAGGCTGTGCTGACTCAGCCGTCCTCCCTCTCTGCAT<br>CTCCTGGAGCATCAGCCAGTATCACCTGCACCTTAC<br>GCAGTGACCTCACTGTTAGTCCCTGGATATACTGGT<br>ACCAACAGAAGCCAGGGAGTCCTCCCCGATTTCTCC<br>TGAAATACAAATCAGACTCCAATAACTACCACGGCT<br>CTGGAGTCCCCAGCCGCTTCTCTGGATCCAAAGATG<br>CTTCGGCCAATGCAGCGATTTTACTCATCTCTGGACT<br>CCAGTCTGAAGATGAGGCTGACTATTACTGTCAGAC<br>TTGGCACACCACCACTGTGGTATTTGGCGGAGGGAC<br>CAAGCTGACCGTCCTA |
| 63 | 15-20G VH AMINO ACID SEQUENCE | QVQLVEFGGGIFQPGGSLRLSCVASGFSFRYYGFHWV<br>RQAPGKGLEWLAVVWHDGRETHYGDSVRGRFTISRD<br>NYKNTVFLEMDSLRVEDTAVYHCARDRGSDEPIDYW<br>GQGVLVTVSS |
| 64 | 15-20G VL AMINO ACID SEQUENCE | QAVLTQPSSLSASPGASASITCTLRSDLTVSPWIYWYQ<br>QKPGSPPRFLLKYKSDSNNYHGSGVPSRFSGSKDASAN<br>AAILLISGLQSEDEADYYCQTWHTTTVVFGGGTKLTV<br>L |
| 65 | 23-120 VH NUCLEOTIDE SEQUENCE | CAGGTGCAGTTGGTGGAGTTTGGGGGAGGCATTTTC<br>GAGCCTGGGGGGTCCCTGAGACTCTCCTGTGTCGCG<br>TCTGGATTCTCCTTCAGGCATTATGGTATGCACTGG<br>GTCCGCCAGGCTCCAGGCAAGGGGCTGGAGTGGCT<br>GGCAGTTGTATGGCATGATGGAAGGGAGACACATT<br>ATGGAGACTCCGTGAAGGGCGATTCACCATCTCCA<br>GAGACAATTACAAGAATACGCTGTTTTTGCAAATGG<br>ACAGCCTGAGAGTCGAGGACACGGCTGTCTATCACT<br>GTGCGAGAGATCGTGGTAGCGACGAACCTATTGACT<br>ACTGGGGCCAGGGAGTTTTGGTCACCGTCTCCTCA |
| 66 | 23-120 VL NUCLEOTIDE SEQUENCE | CAGGCTGTGCTGACTCAGCCGTCCTCCCTCTCTGCAT<br>CTCCTGGAGCATCAGCCAGTATCACCTGCACCTTAC<br>GCAGTGACGTCACTGTTAGTCCCTGGACATACTGGT<br>ACCAACAGAAGCCAGGGAGTCCTCCCCAATTTCTCC<br>TGAGATACAAATCAGACTCTGATAAGTATCAGGGCT<br>CTGGAGTCCCCAGCCGCTTCTCTGGATCCAAAAATG |

| SEQ ID NO | DESCRIPTION | SEQUENCE |
|---|---|---|
| | | CTTCGGCCAATGCAGCGATTTTACTCATCTCTGGGCT CCAGTCTGAAGATGAGGCTGACTATTACTGTCAGAC TTGGCACACCAACAATGTGGTATTTGGCGGAGGGAC CAAGCTGACCGTCCTA |
| 67 | 23-120 VH AMINO ACID SEQUENCE | QVQLVEFGGGIFEPGGSLRLSCVASGFSFRHYGMHWV RQAPGKGLEWLAVVWHDGRETHYGDSVKGRFTISRD NYKNTLFLQMDSLRVEDTAVYHCARDRGSDEPIDYW GQGVLVTVSS |
| 68 | 23-120 VL AMINO ACID SEQUENCE | QAVLTQPSSLSASPGASASITCTLRSDVTVSPWTYWYQ QKPGSPPQFLLRYKSDSDKYQGSGVPSRFSGSKNASAN AAILLISGLQSEDEADYYCQTWHTNNVVFGGGTKLTV L |
| 69 | 31-2C VH NUCLEOTIDE SEQUENCE | CAGGTGCAGTTGGTGGAGTTTGGGGGAGGCATTTTC CAGCCTGGGGGGTCCCTGAGACTCTCCTGTGTCGCG TCTGGATTCTCCTTCAGATATTATGGTTTCCACTGGG TCCGCCAGGCTCCAGGCAAGGGGCTGGAGTGGCTG GCAGTTGTATGGCATGATGGAAGGGAGACACATTAT GGAGACTCCGTGAAGGGGCGATTCACCATCTCCAGA GACAATTACAAGAACACGCTGTTTTTGCAAATGGAC AGCCTGAGAGTCGAGGACACGGCTGTCTATCACTGT GCGAGAGATCGTGGTAGCGACGAACCTATTGACTAC TGGGGCCAGGGAGTTTTGGTCACCGTCTCCTCA |
| 70 | 31-2C VL NUCLEOTIDE SEQUENCE | CAGGCTGTGCTGACTCAGCCGTCCTCCCTCTCTGCAT CTCCTGGAGCATCAGCCAGTATCACCTGCACCTTAC GCAGTGGCCTCACTGTTAGTCCCTGGATATACTGGT ACCAACAGAAGCCAGGGAGTCCTCCCCAATTTCTCC TGAGATACAAATCAGACTCCGAAAACTACCGGGGC TCTGGAGTCCCCAGTCGCTTCTCTGGATCCAAAGAG GCTTCGGCCAATGCAGCGATTTTATTCATCTCTGGA CTCCAGTCTGAAGATGAGGCTGACTATTACTGTCAG ACTTGGCACACCAGCACAGTGGTATTTGGCGGAGGG ACCAAGCTGACCGTCCTA |
| 71 | 31-2C VH AMINO ACID SEQUENCE | QVQLVEFGGGIFQPGGSLRLSCVASGFSFRYYGFHWV RQAPGKGLEWLAVVWHDGRETHYGDSVKGRFTISRD NYKNTLFLQMDSLRVEDTAVYHCARDRGSDEPIDYW GQGVLVTVSS |
| 72 | 31-2C VL AMINO ACID SEQUENCE | QAVLTQPSSLSASPGASASITCTLRSGLTVSPWIYWYQ QKPGSPPQFLLRYKSDSENYRGSGVPSRFSGSKEASAN AAILFISGLQSEDEADYYCQTWHTSTVVFGGGTKLTVL |
| 73 | 36-19H VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACATTTTCACCAACTTTGGCATCAACTGG GTGCGACAGGCCCCTGGTCAAGGGCTTGAGTGGATG GGATGGATGAACTCCAAGTATGGTAATGCGGACTCT GCACATAAGTTCCAGGACAGACTCACTATGACCACC GACACCTCCACAAGTACAGCCTACATGGAGCTGAG AAATCTGAGATCTGAGGACACGGCCGTATATTATTG CGCGAGAATGAATTACCGTGATTCGAAGTGGGACGT GAATTGGTTCGACCCCTGGGGCCAGGGAACCCTGAT CACCGTCTCCTCA |
| 74 | 36-19H VL NUCLEOTIDE SEQUENCE | CAGTCTGTGGTGACTCAGCCACCCTCAGCGTCTGGG ACCCCCGGGCAGAGGGTCACCATCTCCTGTTCTGGA AGCAGGTCCAACGTCGAAAGAAATTTTGTTTACTGG TACCAGCAGCTCCCAGGAACGGCCCCCAAACTTCTC ATCTATATGAACAATCAGCGCCCCTCAGGGGTCCCT GACCGATTCTCTGGCTCTCGTTCTGGCACCTCAGCCT CCCTGGCCATCACTGGGCTTCGGTCCGAGGATGAGG CTGATTATTATTGTGCAGTTTGGGATGACAATCTCA GAGGCTGGGTGTTCGGCGGAGGGACCGAGGTGACC GTCCTA |
| 75 | 36-19H VH AMINO ACID SEQUENCE | QVQLVQSGAEIKRPGASVKVSCKASGYIFTNFGINWV RQAPGQGLEWMGWMNSKYGNADSAHKFQDRLTMTT DTSTSTAYMELRNLRSEDTAVYYCARMNYRDSKWDV NWFDPWGQGTLITVSS |

LISTING OF THE SEQUENCES

| SEQ ID NO | DESCRIPTION | SEQUENCE |
|---|---|---|
| 76 | 36-19H VL AMINO ACID SEQUENCE | QSVVTQPPSASGTPGQRVTISCSGSRSNVERNFVYWYQ QLPGTAPKLLIYMNNQRPSGVPDRFSGSRSGTSASLAIT GLRSEDEADYYCAVWDDNLRGWVFGGGTEVTVL |
| 77 | 36-21L VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACACTTTCACCGGCTTTGGTATCAACTGG GTGCGACAGGCCCCAGGACAGGGGCTTGAGTGGAT GGGATGGATGAACTCCAACACTGGTGATGCGGACTC TGCACAGAAGTTCCAGGGCAGACTCACTATGACCAC CGACACCTCCACAAGTACAGCCCACATGGAGCTGAC GAATCTGGGATCTGAGGACACGGCCGTATACTATTG CGCGAGAATGAATTTCCTTGGTTCGAAGTGGGAGGT GAACTGGTTCGACCCCTGGGGCCAGGGAACCCTGAT CACCGTCTCCTCA |
| 78 | 36-21L VL NUCLEOTIDE SEQUENCE | GATGTTGTGCTGACTCAGTCTCCACTCTCCCTGTCCG TCACCCTTGGACAGCCGGCCTCCATCTCCTGCAGGT CCAGTCACAGCCTCCCAAGAGATGATGAATACTCCT ACCTGAATTGGTTTCAGCAGAGGCCAGGCCAGTCTC CAAGGCGCCTAATTTATAGGGTTTCTAAGCGGGACT CTGGGGTCCCAGACAGATTCAGCGGCAGTGGGTCA GACACTTATTTCACACTGACAATCAGCAGGGTGGAG GCTGAGGATGTTGGAGTTTATTACTGCATGCAAGGT ACATACTGGCCCGGGACGTTCGGCCAAGGGACGAA GTTGGAAATCGAGCGA |
| 79 | 36-21L VH AMINO ACID SEQUENCE | QVQLVQSGAEIKRPGASVKVSCKASGYTFTGFGINWV RQAPGQGLEWMGWMNSNTGDADSAQKFQGRLTMTT DTSTSTAHMELTNLGSEDTAVYYCARMNFLGSKWEV NWFDPWGQGTLITVSS |
| 80 | 36-21L VL AMINO ACID SEQUENCE | DVVLTQSPLSLSVTLGQPASISCRSSHSLPRDDEYSYLN WFQQRPGQSPRRLIYRVSKRDSGVPDRFSGSGSDTYFT LTISRVEAEDVGVYYCMQGTYWPGTFGQGTKLEIER |
| 81 | 41-180 VH NUCLEOTIDE SEQUENCE | GAGGTACAGCTGGTGGAGTCTGGGGGAGGCCTGGT CCAGCCTGGGGGGTCTCTGAGACTCTCCTGTGCAGC CTCTGGATTCACCTTTAATCACGATTGGATGACTTG GGTCCGCCAGGCTCCAGGGAAGGGTCTGGAGTGGG TGGCCAACATAATACAAGATGGAAGCGAAACATAC TATGTGGACTCTGTGAAGGGCCGATTCACCATCTCC AGAGACAATGCCAAGAATTTACTGTATCTGCAGATG AACAGCCTGAGAGTCGAGGACACGGCTGTGTATTTC TGTGGCCGGAGTATGGACGTCTGGGGCCAAGGGAC CACGGTCATCGTCTCCTCA |
| 82 | 41-180 VL NUCLEOTIDE SEQUENCE | CAGTCTGTGCTGACTCAGCCACCCTCAGCGTCTGGG ACCCCCGGGCAGAGGGTCACCATCTCTTGTTCTGGA AGCAGCTCCAACATCGGAAGTAATACTGTGAACTGG TACCACCAGGTCCCAGGAACGGCCCCCAAACTCCTC ATCTATACTGATAATCAGCGGCCCTCAGGGGTCCCT GACCGATTCTCTGGCTCCAAGTCTGGCACCTCAGCC TCCCTGGCCATCAGTGGGCTCCAGTCTGAGGATGAA GGTGATTATTACTGTGCAGCGAGGGATGGCAGCCTG GATGTTTGGGTGTTCGGCGGAGGGACCAAAGTGACT GTCCTA |
| 83 | 41-180 VH AMINO ACID SEQUENCE | EVQLVESGGGLVQPGGSLRLSCAASGFTFNHDWMTW VRQAPGKGLEWVANIIQDGSETYYVDSVKGRFTISRD NAKNLLYLQMNSLRVEDTAVYFCGRSMDVWGQGTT VIVSS |
| 84 | 41-180 VL AMINO ACID SEQUENCE | QSVLTQPPSASGTPGQRVTISCSGSSSNIGSNTVNWYH QVPGTAPKLLIYTDNQRPSGVPDRFSGSKSGTSASLAIS GLQSEDEGDYYCAARDGSLDVWVFGGGTKVTVL |
| 85 | 5-14N VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACACTTTCACCAACTTTGGAATCAACTGG GTGCGACAGGCCCCTGGACAAGGGCTTGAGTGGAT GGGATGGATGAACTCCAGAACTGGTGATGCGGACT CTGCACAGAACTTCCAGGGCAGGCTCACTATGACCA CCGACACCTCCAGAAGTATAGCCTACATGGAGCTGA |

| SEQ ID NO | DESCRIPTION | SEQUENCE |
|---|---|---|
| | | CGCACCTGACCTCTGAGGACACGGCCGTATATTATT GCGCGAGAATGAATTTCCTTGGTTCGAGGTGGGAGG TGAACTGGTTCGACCCCTGGGGCCAGGGAACCCTGA TCACCGTCTCCTCA |
| 86 | 5-14N VL NUCLEOTIDE SEQUENCE | CAGTCTGTGGTGACTCAGCCACCCTCAGTGTCTGGG ACCCCCGGGCAGAGGGTCACCATCTCCTGTTCTGGA AGCAGGTCCAACGTCGAAAGAAATTTTTTTTACTGG TATCAGCAATTCCCAGGAACGGCCCCCAAACTTCTC ATCTATATGAACAGTCAGCGGCCCGCAGGGGTCCCT GACCGATTCTCTGGCTCTCGTTCTGGCACCTCAGTTT CCCTGGCCATCACTGGGCTTCGGTCCGAGGATGAGG CTGACTATTATTGTGCAACTTGGGATGACAATCTGA GAGGCTGGGTGTTCGGCGGAGGGACCAAGGTGACC GTCCTA |
| 87 | 5-14N VH AMINO ACID SEQUENCE | QVQLVQSGAEIKRPGASVKVSCKASGYTFTNFGINWV RQAPGQGLEWMGWMNSRTGDADSAQNFQGRLTMTT DTSRSIAYMELTHLTSEDTAVYYCARMNFLGSRWEVN WFDPWGQGTLITVSS |
| 88 | 5-14N VL AMINO ACID SEQUENCE | QSVVTQPPSVSGTPGQRVTISCSGSRSNVERNFFYWYQ QFPGTAPKLLIYMNSQRPAGVPDRFSGSRSGTSVSLAIT GLRSEDEADYYCATWDDNLRGWVFGGGTKVTVL |
| 89 | 11-19C VH NUCLEOTIDE SEQUENCE | CAGGTGCAGCTGGTGCAGTCTGGGGCTGAGATTAAG CGGCCTGGGGCCTCAGTGAAGATCTCCTGCAAGGCG TCTGGATACATTTTCACCAGCTTTGGTATCAACTGG GTGCGACAGGCCCCTGGACAAGGGCTTGAGTGGAT GGGATGGATGAACTCCAACACTGGTGATGCGGACTC TCTACAGAAGTTCCAGGGCAGACTCACCATGACCAC CGACACCTCCACAAGCACAGCCTACATGGAATTGAG CAATCTGAGATCTGAAGACACGGCCGTATATTATTG CGCGAGAATGAATTTCCATGGTTCGAGGTGGGACGT GAACTGGTTCGACCCCTGGGGCCAGGGAACCCTGAT CACCGTCTCCTCA |
| 90 | 11-19C VL NUCLEOTIDE SEQUENCE | CAGTCTGTGGTGACTCAGCCACCCTCAGCGTCTGGG ACCCCCGGGCAGAGGGTCATCATCTCCTGTTCTGGA AGCGGGTCCAACGTCGAAAGAAATTCTGTTTACTGG TACCAACAGTTCCCGGGAACGGCCCCCAAACTTCTC ATCTACATGAGCAATAGGCGCCCCTCAGGGGTCCCT GACCGATTCTTTGGCTCTCGTTCTGGCACCTCAGCCT CCCTGGCCATCACTGGGCTTCGGCCCGAGGATGAGG CTGATTATTATTGTGCAGTTTGGGATGACAGTCTGA GAGGCTGGGTATTCGGCGGAGGGACCAAGGTGACC GTCCTA |
| 91 | 11-19C VH AMINO ACID SEQUENCE | QVQLVQSGAEIKRPGASVKISCKASGYIFTSFGINWVR QAPGQGLEWMGWMNSNTGDADSLQKFQGRLTMTTD TSTSTAYMELSNLRSEDTAVYYCARMNFHGSRWDVN WFDPWGQGTLITVSS |
| 92 | 11-19C VL AMINO ACID SEQUENCE | QSVVTQPPSASGTPGQRVIISCSGSGSNVERNSVYWYQ QFPGTAPKLLIYMSNRRPSGVPDRFFGSRSGTSASLAIT GLRPEDEADYYCAVWDDSLRGWVFGGGTKVTVL |
| 93 | F-8C VH NUCLEOTIDE SEQUENCE | CAGGTGCAGCTGGCGGAGTCTGGGGGAGGCGTGGT CCAGCCTGGGGGGTCCCTGAGACTTTCCTGTGCAGC GTCTGGATTCAGTCTCAAGAGTTATGGCATTCACTG GGTCCGCCAGGCCCCAGGCAAGGGGCTGGAGTGGG TGGCAGTTATCTGGCCCCGACGAGATACACAGTATG CAGACTCCGTGAAGGGCCGAGTCACCATGTACAGA GACGACTATAGGAATACGGTCTATCTACAGATGAAC AGCCTGAGATTCGATGACGCGGCTCTGTATCGGTGT GCGAGAGATCGCGGTGAAGACAATCCCATA GATTTCTGGGGCCAGGGAACCCTGGTCACCGTCTCC TCA |
| 94 | F-8C VL NUCLEOTIDE SEQUENCE | CAGGCTGTGCTGACTCAGCCGTCTTCCCTCTCTGCAT CTCCTGGAGCATCAGCCAGTCTCACCTGCACCTTGC TCAGCGGCATCAATGTTGGTCCCTACTGGATATACT GGTATCAGCAGAAGGCAGGGAGTCCTCCCCAGTTTC TCCTCAGGTACAGGTCAGACTCAGATGAGGAGCAG |

| SEQ ID NO | DESCRIPTION | SEQUENCE |
|---|---|---|
| | | GGCTCTGAGGTCCCCAGCCGCTTCTCTGGATCCAAA GATGCCTCGGCCAATGCAGGGATTTTGGTCATCTCT GGGCTCCAGTCTGAAGATGAAGCTGACTATTACTGT ATGATCTGGCACAGGACCGGTGTGATTTTCGGCGGA GGGACCAAGCTGACCGTCCTA |
| 95 | F-8C VH AMINO ACID SEQUENCE | QVQLAESGGGVVQPGGSLRLSCAASGFSLKSYGIHWV RQAPGKGLEWVAVIWPRRDTQYADSVKGRVTMYRD DYRNTVYLQMNSLRFDDAALYRCARDRGEDNPIDFW GQGTLVTVSS |
| 96 | F-8C VL AMINO ACID SEQUENCE | QAVLTQPSSLSASPGASASLTCTLLSGINVGPYWIYWY QQKAGSPPQFLLRYRSDSDEEQGSEVPSRFSGSKDASA NAGILVISGLQSEDEADYYCMIWHRTGVIFGGGTKLTV L |
| 97 | 21-6M VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACATTTTCACCAGCTTTGGTATCAACTGG GTGCGACAGGCCCCTGGACAAGGGCTTGAGTGGAT GGGATGGATGAACTCCAACACTGGTGATGCGGACTC TGTACAGAAGTTCCAGGGCAGACTCACCATGACCAC CGACCCCTCCACAAGTACAGCCTATATGGAACTGAG GAATCTGAGATCTGACGACACGGCCGTATATTATTG CGCGAGAATGAACTTCTTTGGTTCGCAGTGGGAAGT GAACTGGTTCGACCCCTGGGGCCAGGGAACCCTGAT CACCGTCTCCTCA |
| 98 | 21-6M VL NUCLEOTIDE SEQUENCE | CAGTCTGTGGTGACTCAGCCACCCTCAGCGTCTGGG ACCCCCGGGCAGAGGATCACCATCTCCTGTTCTGGA AGCAGGTCCAACGTCGAAAGAAATTCTGTTTACTGG TACCAGCAGCTCCGAGGAACGGCCCCCAAACTTCTC ATCTATATGAGCAATCAGCGCCCCTCAGGGGTCCCT GACCGATTCTCTGGCTCTCGTTCTGGCACCTCAGCCT CCCTGGCCATCACTGGGCTTCGGTCCGAGGATGAGG CTGATTATTATTGTGCAGTTTGGGATGACAATCTCA GAGGCTGGGTGTTCGGCGGAGGGACCGAGGTGACC GTCCTA |
| 99 | 21-6M VH AMINO ACID SEQUENCE | QVQLVQSGAEIKRPGASVKVSCKASGYIFTSFGINWVR QAPGQGLEWMGWMNSNTGDADSVQKFQGRLTMTTD PSTSTAYMELRNLRSDDTAVYYCARMNFFGSQWEVN WFDPWGQGTLITVSS |
| 100 | 21-6M VL AMINO ACID SEQUENCE | QSVVTQPPSASGTPGQRITISCSGSRSNVERNSVYWYQ QLRGTAPKLLIYMSNQRPSGVPDRFSGSRSGTSASLAIT GLRSEDEADYYCAVWDDNLRGWVFGGGTEVTVL |
| 101 | 22-14F VH NUCLEOTIDE SEQUENCE | CCAGGTGCACCTGGTGCAGTCTGGGGCTGAGATTAA GAGGCCTGGGGCCTCAGTGAAGGTCTCCTGCAAGGC GTCTGGATACACTTTCACCAGCTTTGGTATCAACTG GGTGCGACAGGCCCCTGGACAAGGGCTTGAGTGGA TGGGATGGATGAACTCCAACAGTGGTGATGCGGACT CTGCACAGAAGTTCCAGGGCAGACTCACTATGACCA CCGACACCTCCACAAGTACAGCCTACATGGAGCTGA GGAATCTGAGATCTGAGGACACGGCCGTATATTATT GCGCGAGAATGAATTTCCGTGGTTCGAAGTGGGAG GTGAACTGGTTCGACCCCTGGGGCCAGGGAACCCTG ATCACCGTCTCCTCA |
| 102 | 22-14F VL NUCLEOTIDE SEQUENCE | CAGTCTGTGGTGACTCAGCCACCCTCAGCGTCTGGG ACCCCCGGGCAGAGGGTCACCATCTCCTGTTCTGGA AGCAGGTCCAACGTCGAAAGAAATTTTGTTTACTGG TACCAGCAACTCCCAGGAACGGCCCCCAAACTTCTC ATCTATATGAACAGTCAGCGGCCCTCAGGGGTCCCT GACCGATTCTCTGGCTCTCGTTCTGGCACCTCAGCCT CCCTGGCCATCACTGGGCTTCGGTCCGAGGATGAGG CTGACTATTATTGTGCAACTTGGGATGACAATCTGA GAGGCTGGGTGTTCGGCGGAGGGACCAAGGTGACC GTCCTA |

| SEQ ID NO | DESCRIPTION | SEQUENCE |
|---|---|---|
| 103 | 22-14F VH AMINO ACID SEQUENCE | QVHLVQSGAEIKRPGASVKVSCKASGYTFTSFGINWV RQAPGQGLEWMGWMNSNSGDADSAQKFQGRLTMTT DTSTSTAYMELRNLRSEDTAVYYCARMNFRGSKWEV NWFDPWGQGTLITVSS |
| 104 | 22-14F VL AMINO ACID SEQUENCE | QSVVTQPPSASGTPGQRVTISCSGSRSNVERNFVYWYQ QLPGTAPKLLIYMNSQRPSGVPDRFSGSRSGTSASLAIT GLRSEDEADYYCATWDDNLRGWVFGGGTKVTVL |
| 105 | 24-5D VH NUCLEOTIDE SEQUENCE | CAGGTGCAGCTGGTGCAGTCTGGGGCTGAGATTAAG AGGCCTGGGGCCTCAGTGAAGGTCTCCTGCAAGGCG TCTGGATACACCTTCACCAGATTTGGTATCAACTGG GTGCGACAGGCCCCTGGACAAGGGCTTGAGTGGAT GGGATGGATGAACTCCAACACTGGTGATGCGGACTC TGCACAGAAGTTCCAGGGCAGACTCAGTATGACCAC CGACACCTCCACAAGTACAGCCTACATGGAGCTGAA GAGTCTGACATCTGACGACACGGCCGTATATTTTTG CGCGAGAATGAATTACTGGGGGTCGAAGTGGGACG TGAACTGGTTCGACCCCTGGGGCCAGGGAACCCTGA TCACCGTCTCCTCA |
| 106 | 24-5D VL NUCLEOTIDE SEQUENCE | CAGTCTGTGGTGACTCAGCCACCCTCAGCGTCTGGG ACCCCCGGGCAGAGGGTCACCATCTCCTGTTCTGGA AGAAGGACCAACGTGGAAAGAAATTCTGTCTACTG GTACCAGCAGCTCCCAGGAACGGCCCCCAAACTTCT CATCTATATGAGCAATAAGCGCCCCTCAGGGGTCCC TGACCGATTCTCCGGCTCTCGTTCTGGCACCTCTGCC TCCCTGGCCATCACTGGGCTTCGGTCCGAGGATGAG GCTGATTATTATTGTGCAGTTTGGGATGACAATCTG AGAGGCTGGGTGTTCGGCGGAGGGACCAAGGTGAC CGTCCTA |
| 107 | 24-5D VH AMINO ACID SEQUENCE | QVQLVQSGAEIKRPGASVKVSCKASGYTFTRFGINWV RQAPGQGLEWMGWMNSNTGDADSAQKFQGRLSMTT DTSTSTAYMELKSLTSDDTAVYFCARMNYWGSKWDV NWFDPWGQGTLITVSS |
| 108 | 24-5D VL AMINO ACID SEQUENCE | QSVVTQPPSASGTPGQRVTISCSGRRTNVERNSVYWY QQLPGTAPKLLIYMSNKRPSGVPDRFSGSRSGTSASLAI TGLRSEDEADYYCAVWDDNLRGWVFGGGTKVTVL |
| 109 | 15-6J CDRH1 | GFSFRHYGMH |
| 110 | 15-6J CDRH2 | VVWHDGRETHYGDSV |
| 111 | 15-6J CDRH3 | DRGSDEPIDY |
| 112 | 15-6J CDRL1 | TLRSDVTVSPWTY |
| 113 | 15-6J CDRL2 | KSDSDKYQGS |
| 114 | 15-6J CDRL3 | QTWHTTTV |
| 115 | 23-12O CDRH1 | GFSFRHYGMH |
| 116 | 23-12O CDRH2 | VVWHDGRETHYGDSV |
| 117 | 23-12O CDRH3 | DRGSDEPIDY |
| 118 | 23-12O CDRL1 | TLRSDVTVSPWTY |
| 119 | 23-12O CDRL2 | KSDSDKYQGS |
| 120 | 23-12O CDRL3 | QTWHTSTV |
| 121 | 31-2C CDRH1 | GFSFRYYGFH |
| 122 | 31-2C CDRH2 | VVWHDGRETHYGDSV |
| 123 | 31-2C CDRH3 | DRGSDEPIDY |
| 124 | 31-2C CDRL1 | TLRSGLTVSPWIY |

-continued

| SEQ ID NO | DESCRIPTION | SEQUENCE |
|---|---|---|
| 125 | 31-2C CDRL2 | KSDSENYRGS |
| 126 | 31-2C CDRL3 | QTWHTSTV |
| 127 | 15-20G CDRH1 | GFSFRYYGFH |
| 128 | 15-20G CDRH2 | VVWHDGRETHYGDSV |
| 129 | 15-20G CDRH3 | DRGSDEPIDY |
| 130 | 15-20G CDRL1 | TLRSDLTVSPWIY |
| 131 | 15-20G CDRL2 | KSDSNNYHGS |
| 132 | 15-20G CDRL3 | QTWHTTTV |
| 133 | 4-22O CDRH1 | GFPFRYYGFH |
| 134 | 4-22O CDRH2 | VVWHNGRETYYEDSV |
| 135 | 4-22O CDRH3 | DRGSDEPIDY |
| 136 | 4-22O CDRL1 | TLRSDLTVGPYWMY |
| 137 | 4-22O CDRL2 | KSDSEKYQGS |
| 138 | 4-22O CDRL3 | QTWHANTV |
| 139 | 6-20C CDRH1 | GFSFRRFGMH |
| 140 | 6-20C CDRH2 | VVWHDGRETHYGDSV |
| 141 | 6-20C CDRH3 | DPGQDEAIDY |
| 142 | 6-20C CDRL1 | TLHSGLTVGPYWIY |
| 143 | 6-20C CDRL2 | KSDSEEYRAS |
| 144 | 6-20C CDRL3 | MTWHTNKV |
| 145 | J-5N CDRH1 | GFSLRSFGMH |
| 146 | J-5N CDRH2 | VIWPRRSQIQYADSV |
| 147 | J-5N CDRH3 | DPGEDNPIDY |
| 148 | J-5N CDRL1 | TFLSGINVGPYWIY |
| 149 | J-5N CDRL2 | KSDSDKHQGS |
| 150 | J-5N CDRL3 | MIWHVSGV |
| 151 | F-8C CDRH1 | GFSLKSYGIH |
| 152 | F-8C CDRH2 | VIWPRRDTQYADSV |
| 153 | F-8C CDRH3 | DRGEDNPIDF |
| 154 | F-8C CDRL1 | TLLSGINVGPYWIY |
| 155 | F-8C CDRL2 | RSDSDEEQGS |
| 156 | F-8C CDRL3 | MIWHRTGV |
| 157 | B-21J CDRH1 | GFSFRHYGMH |
| 158 | B-21J CDRH2 | VIWHNGRDREYADSV |
| 159 | B-21J CDRH3 | DRGEDEPIDF |
| 160 | B-21J CDRL1 | TLRSGLSAGPKWIY |
| 161 | B-21J CDRL2 | KSDSEERRSS |

LISTING OF THE SEQUENCES

| SEQ ID NO | DESCRIPTION | SEQUENCE |
|---|---|---|
| 162 | B-21J CDRL3 | AIWHSNVV |
| 163 | J-8G CDRH1 | GFSFRHYGMH |
| 164 | J-8G CDRH2 | VIWHNGRDKDYADSV |
| 165 | J-8G CDRH3 | DRGEDEPIDF |
| 166 | J-8G CDRL1 | TLRSGLNVGPYWIY |
| 167 | J-8G CDRL2 | KSDSEKRRSS |
| 168 | J-8G CDRL3 | AIWHSNAV |
| 169 | 9-5L CDRH1 | GFTLKRYGIH |
| 170 | 9-5L CDRH2 | VTWHDGNIYYADSV |
| 171 | 9-5L CDRH3 | DAGQNAPIDL |
| 172 | 9-5L CDRL1 | TLPSGINVATHWIY |
| 173 | 9-5L CDRL2 | KSDSDIQHGS |
| 174 | 9-5L CDRL3 | MIWYSTAV |
| 175 | 2-20G CDRH1 | GFTFPNAWFN |
| 176 | 2-20G CDRH2 | RIKSHSDGGTADYAAPV |
| 177 | 2-20G CDRH3 | LEIYHPVDV |
| 178 | 2-20G CDRL1 | RSSHSLPRDDEYSYLN |
| 179 | 2-20G CDRL2 | RVSKRDS |
| 180 | 2-20G CDRL3 | MQGTYWPGT |
| 181 | 3-17I CDRH1 | GFTFITAWMT |
| 182 | 3-17I CDRH2 | LIKSGNDGGAIEYAAPV |
| 183 | 3-17I CDRH3 | NDVALVWGVTPPLLL |
| 184 | 3-17I CDRL1 | TLSSGHGNYPVA |
| 185 | 3-17I CDRL2 | NADGSHIKGA |
| 186 | 3-17I CDRL3 | QTWAPGW |
| 187 | F-18D CDRH1 | GFVFTTAWMN |
| 188 | F-18D CDRH2 | RIKSKNEAETTDYAAPV |
| 189 | F-18D CDRH3 | LETYYESDF |
| 190 | F-18D CDRL1 | RSSQSLAEREEDILLN |
| 191 | F-18D CDRL2 | RVSKRES |
| 192 | F-18D CDRL3 | MQRTHWPQT |
| 193 | 41-18O CDRH1 | GFTFNHDWMT |
| 194 | 41-18O CDRH2 | NIIQDGSETYYVDSV |
| 195 | 41-18O CDRH3 | GRVSMDV |
| 196 | 41-18O CDRL1 | SGSSSNIGSNTVN |
| 197 | 41-18O CDRL2 | TDNQRPS |
| 198 | 41-18O CDRL3 | AARDGSLDVW |

-continued

| SEQ ID NO | DESCRIPTION | SEQUENCE |
|---|---|---|
| 199 | 18-11C CDRH1 | GYTFTSFGIN |
| 200 | 18-11C CDRH2 | WMNSNSGDADSAQKF |
| 201 | 18-11C CDRH3 | MNFRGSKWEVNWFDP |
| 202 | 18-11C CDRL1 | SGSRSNVERNFVY |
| 203 | 18-11C CDRL2 | MNSQRPS |
| 204 | 18-11C CDRL3 | ATWDDNLRGW |
| 205 | 22-14F CDRH1 | GYTFTSFGIN |
| 206 | 22-14F CDRH2 | WMNSNSGDADSAQKF |
| 207 | 22-14F CDRH3 | MNFRGSKWEVNWFDP |
| 208 | 22-14F CDRL1 | SGSRSNVERNFVY |
| 209 | 22-14F CDRL2 | MNSQRPS |
| 210 | 22-14F CDRL3 | ATWDDNLRGW |
| 211 | 20-2D CDRH1 | GYTFTRFGIN |
| 212 | 20-2D CDRH2 | WMNSNSGNADSAQKF |
| 213 | 20-2D CDRH3 | MNYRGSKWEINWFDP |
| 214 | 20-2D CDRL1 | SGSRSNVQRNFVY |
| 215 | 20-2D CDRL2 | MNNNRPS |
| 216 | 20-2D CDRL3 | ATWDDNLRGW |
| 217 | 36-21L CDRH1 | GYTFTGFGIN |
| 218 | 36-21L CDRH2 | WMNSNTGDADSAQKF |
| 219 | 36-21L CDRH3 | MNFLGSKWEVNWFDP |
| 220 | 36-21L CDRL1 | RSSHSLPRDDEYSYLN |
| 221 | 36-21L CDRL2 | RVSKRDS |
| 222 | 36-21L CDRL3 | MQGTYWPGT |
| 223 | 36-19H CDRH1 | GYIFTNFGIN |
| 224 | 36-19H CDRH2 | WMNSKYGNADSAHKF |
| 225 | 36-19H CDRH3 | MNYRDSKWDVNWFDP |
| 226 | 36-19H CDRL1 | SGSRSNVERNFVY |
| 227 | 36-19H CDRL2 | MNNQRPS |
| 228 | 36-19H CDRL3 | AVWDDNLRGW |
| 229 | 21-6M CDRH1 | GYIFTSFGIN |
| 230 | 21-6M CDRH2 | WMNSNTGDADSVQKF |
| 231 | 21-6M CDRH3 | MNFFGSQWEVNWFDP |
| 232 | 21-6M CDRL1 | SGSRSNVERNSVY |
| 233 | 21-6M CDRL2 | MSNQRPS |
| 234 | 21-6M CDRL3 | AVWDDNLRGW |
| 235 | 24-5D CDRH1 | GYTFTRFGIN |

-continued

| LISTING OF THE SEQUENCES | | |
|---|---|---|
| SEQ ID NO | DESCRIPTION | SEQUENCE |
| 236 | 24-5D CDRH2 | WMNSNTGDADSAQKF |
| 237 | 24-5D CDRH3 | MNYWGSKWDVNWFDP |
| 238 | 24-5D CDRL1 | SGRRTNVERNSVY |
| 239 | 24-5D CDRL2 | MSNKRPS |
| 240 | 24-5D CDRL3 | AVWDDNLRGW |
| 241 | 12-14G CDRH1 | GYTFTNYGVN |
| 242 | 12-14G CDRH2 | WMNTNSGDTGYAQKF |
| 243 | 12-14G CDRH3 | AYFFDSWNKGNWFDP |
| 244 | 12-14G CDRL1 | SGGSSNLGRSYIY |
| 245 | 12-14G CDRL2 | KNSQRPS |
| 246 | 12-14G CDRL3 | AAWDDSLSGSW |
| 247 | 2-8M CDRH1 | GGYVTIKDNYWV |
| 248 | 2-8M CDRH2 | SMSYSGNAYYNPSL |
| 249 | 2-8M CDRH3 | RSAAAGGGNEWFDP |
| 250 | 2-8M CDRL1 | SGSTFNIGNNYVS |
| 251 | 2-8M CDRL2 | DNDKRPS |
| 252 | 2-8M CDRL3 | ATWDNRLDAV |
| 253 | 6-8N CDRH1 | GFAFTTAWMT |
| 254 | 6-8N CDRH2 | LIKSTNDGGSIDYAAPV |
| 255 | 6-8N CDRH3 | NDVVRLRGVTPPILL |
| 256 | 6-8N CDRL1 | TLSSGHHSYPVA |
| 257 | 6-8N CDRL2 | NGDGSHTKGDG |
| 258 | 6-8N CDRL3 | QTWATGW |
| 259 | 5-14N CDRH1 | GYIFTNFGIN |
| 260 | 5-14N CDRH2 | WMNSRTGDADSAQNF |
| 261 | 5-14N CDRH3 | MNFLGSRWEVNWFDP |
| 262 | 5-14N CDRL1 | SGSRSNVERNFFY |
| 263 | 5-14N CDRL2 | MNSQRPAG |
| 264 | 5-14N CDRL3 | ATWDDNLRGW |
| 265 | 11-19C CDRH1 | GYIFTSFGIN |
| 266 | 11-19C CDRH2 | WMNSNTGDADSLQKF |
| 267 | 11-19C CDRH3 | MNFHGSRWDVNWFDP |
| 268 | 11-19C CDRL1 | SGSGSNVERNSVY |
| 269 | 11-19C CDRL2 | MSNRPRSG |
| 270 | 11-19C CDRL3 | AVWDDSLRGW |

We claim:

1. An antibody, or an antigen-binding fragment thereof capable of targeting Globo H, SSEA-4 or SSEA-3, comprising a set of three heavy chain CDRs and three light chain CDRs having the amino acid sequences selected from:
   SEQ ID NOs: 109, 110, and 111 and SEQ ID NOs: 112, 113, and 114 (an antibody 15-6J);
   SEQ ID NOs: 115, 116, and 117 and SEQ ID NOs: 118, 119, and 120 (an antibody 23-12O);
   SEQ ID NOs: 121, 122, and 123 and SEQ ID NOs: 124, 125, and 126 (an antibody 31-2C);
   SEQ ID NOs: 127, 128, and 129 and SEQ ID NOs: 130, 131, and 132 (an antibody 15-20G);
   SEQ ID NOs: 133, 134, and 135 and SEQ ID NOs: 136, 137, and 138 (an antibody 4-22O);
   SEQ ID NOs: 151, 152, and 153 and SEQ ID NOs: 154, 155, and 156 (an antibody F-8C);
   SEQ ID NOs: 211, 212, and 213 and SEQ ID NOs: 214, 215, and 216 (an antibody 20-2D);
   SEQ ID NOs: 223, 224, and 225 and SEQ ID NOs: 226, 227, and 228 (an antibody 36-19H);
   SEQ ID NOs: 229, 230, and 231 and SEQ ID NOs: 232, 233, and 234 (an antibody 21-6M); and
   SEQ ID NOs: 235, 236, and 237 and SEQ ID NOs: 238, 239, and 240 (an antibody 24-5D).

2. An antibody, or an antigen-binding fragment thereof capable of targeting Globo H, SSEA-4 or SSEA-3 of claim 1, wherein the antibody or antigen-binding fragment is selected from:
   the antibody comprising a heavy chain variable domain having 90% to 100% sequence homology to the amino acid sequence of SEQ ID NO: 47 and a light chain variable domain having 90% to 100% homology to amino acid sequence of SEQ ID NO: 48;
   the antibody comprising a heavy chain variable domain having 90% to 100% sequence homology to the amino acid sequence of SEQ ID NO: 67 and a light chain variable domain having 90% to 100% homology to amino acid sequence of SEQ ID NO: 68;
   the antibody comprising a heavy chain variable domain having 90% to 100% sequence homology to the amino acid sequence of SEQ ID NO: 71 and a light chain variable domain having 90% to 100% homology to amino acid sequence of SEQ ID NO: 72;
   the antibody comprising a heavy chain variable domain having 90% to 100% sequence homology to the amino acid sequence of SEQ ID NO: 63 and a light chain variable domain having 90% to 100% homology to amino acid sequence of SEQ ID NO: 64;
   the antibody comprising a heavy chain variable domain having 90% to 100% sequence homology to the amino acid sequence of SEQ ID NO: 35 and a light chain variable domain having 90% to 100% homology to amino acid sequence of SEQ ID NO: 36;
   the antibody comprising a heavy chain variable domain having 90% to 100% sequence homology to the amino acid sequence of SEQ ID NO: 95 and a light chain variable domain having 90% to 100% homology to amino acid sequence of SEQ ID NO: 96;
   the antibody comprising a heavy chain variable domain having 90% to 100% sequence homology to the amino acid sequence of SEQ ID NO: 55 and a light chain variable domain having 90% to 100% homology to amino acid sequence of SEQ ID NO: 56;
   the antibody comprising a heavy chain variable domain having 90% to 100% sequence homology to the amino acid sequence of SEQ ID NO: 75 and a light chain variable domain having 90% to 100% homology to amino acid sequence of SEQ ID NO: 76;
   the antibody comprising a heavy chain variable domain having 90% to 100% sequence homology to the amino acid sequence of SEQ ID NO: 99 and a light chain variable domain having 90% to 100% homology to amino acid sequence of SEQ ID NO: 100; or
   the antibody comprising a heavy chain variable domain having 90% to 100% sequence homology to the amino acid sequence of SEQ ID NO: 107 and a light chain variable domain having 90% to 100% homology to amino acid sequence of SEQ ID NO: 108.

3. The antibody or antigen-binding fragment thereof of any one of claim 1 or 2, wherein SSEA-4 has the structure of (Neu5Acα2→3Galβ1→3GalNAcβ1→3Galα1→4Galβ1→4Glcβ1), SSEA-3 has the structure of (2Galβ1→3GalNAcβ1→3Galα1→4Galβ1→4Glcβ1), and Globo H has the structure of (Fucα1→2 Galβ1→3 GalNAcβ1→3 Galα1→4Galβ1→4.

4. The antibody, or an antigen-binding portion thereof of any one of claim 1 or 2, wherein the antibody is a human antibody.

5. The antibody of claim 4, wherein the antibody is an IgG or IgM.

6. The antibody or antigen-binding portion thereof of claim 1 or 2, wherein the antibody or antigen-binding portion thereof is selected from: (a) a whole immunoglobulin molecule; (b) an scFv; (c) a Fab fragment; (d) an F(ab')2; or (e) a disulfide linked Fv.

7. A pharmaceutical composition, comprising:
   an antibody or an antigen-binding fragment thereof of any one of claim 1 or 2; and at least one pharmaceutically acceptable carrier.

8. The pharmaceutical composition of claim 7, further comprising at least one additional therapeutic agent.

9. A method for inhibiting the proliferation of Globo series antigens expressing cancer cells, comprising the administering of an effective amount of a pharmaceutical composition according to claim 7 to a subject in need thereof, wherein the proliferation of cancer cells is inhibited.

10. The method of claim 9, wherein the subject is human.

11. A method of treating Globo series antigens expressing cancer in a subject, the method comprising administering to the subject in need thereof an effective amount of the antibody or an antigen-binding fragment thereof of any one of claim 1 or 2.

12. The method of claim 11, wherein the Globo series antigens expressing cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

13. The method of claim 11, wherein the subject is human.

14. A method for cancer diagnosis in a subject, comprising:
   a. Applying one or more antibodies of any one of claim 1 or 2 that detect expression of a panel of markers to a cell or sample obtained from the subject;
   b. Assaying the binding of the one or more antibodies to the cell or the sample; and
   c. Comparing the binding with a normal control to determine the presence of the cancer in the subject.

15. The method of claim 14, wherein the markers consisting of Globo-H, SSEA-3 or SSEA-4.

16. The method of claim 14, wherein the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

17. The method of claim 14, wherein the cell is cancer stem cell.

18. The method of claim 14, wherein the sample consists serum, blood, plasma, cells, cell medium, saliva, urine, lymph node fluid, tumor biopsy or tissue culture.

19. The method of claim 14, wherein the subject is human.

20. A method of imaging a subject comprising:
   a. Administering an effective amount of an antibody or an antigen-binding fragment thereof of any one of claim 1 or 2, wherein the antibody or an antigen-binding fragment is conjugated to an imaging agent; and
   b. Detecting the imaging agent in the subject.

21. The method of claim 20, wherein the imaging agent is a fluorophore, a dye, an MRI contrast agent or a radionuclide.

22. The method of claim 20, wherein the subject has a cancer, the method further defined as a method of detecting a cancer metastasis.

23. The method of claim 20, wherein the subject is human.

24. An antibody-drug conjugate (ADC) comprising a drug conjugated to an antibody or an antigen-binding fragment that binds Globo H, SSEA-4 or SSEA-3,
   wherein the VH is SEQ ID NO: 35 and the VL is SEQ ID NO: 36 (an antibody 4-22O),
   wherein the VH is SEQ ID NO: 47 and the VL is SEQ ID NO: 48 (an antibody 15-6J),
   wherein the VH is SEQ ID NO: 55 and the VL is SEQ ID NO: 56 (an antibody 20-2D),
   wherein the VH is SEQ ID NO: 63 and the VL is SEQ ID NO: 64 (an antibody 15-20G),
   wherein the VH is SEQ ID NO: 67 and the VL is SEQ ID NO: 68 (an antibody 23-12O),
   wherein the VH is SEQ ID NO: 71 and the VL is SEQ ID NO: 72 (an antibody 31-2C),
   wherein the VH is SEQ ID NO: 75 and the VL is SEQ ID NO: 76 (an antibody 36-19H),
   wherein the VH is SEQ ID NO: 95 and the VL is SEQ ID NO: 96 (an antibody F-8C),
   wherein the VH is SEQ ID NO: 99 and the VL is SEQ ID NO: 100 (an antibody 21-6M), or
   wherein the VH is SEQ ID NO: 107 and the VL is SEQ ID NO: 108 (an antibody 24-5D); and
   wherein the drug is covalently conjugated to the antibody or the antigen-binding fragment by a linker.

25. The ADC of claim 24, wherein the linker comprising a p-nitrophenyl linker, a 4-(4-N-maleimidomethyl) cyclohexane-1-carboxyl hydrazide (MMCCH) linker, a maleimidocaproyl (MC) linker or a maleimidomethyl cyclohexane-1-carboxylate (MCC) linker.

26. The ADC of claim 24, wherein the drug is a chemical compound or a biological agent.

27. The ADC of claim 24, wherein the drug is an anti-proliferative agent.

28. The ADC of claim 27, wherein the anti-proliferative agent is selected from cyclophosphamide, opiate, granulocyte colony-stimulating factor (GCSF), estrogen inhibitors (tamoxifen), aromatase inhibitors, pituitary downregulators, tamoxifen selective estrogen-receptor modulator rolaxifene, estrogen receptor down-regulator, anticoagulant, enzyme (rasburicase), Hematopoietic growth factor, anti-neoplastic Agent (antimetabolites, miscellaneous cytotoxic agents, vinca alkaloid, Epipodophyllotoxins, Alkylating agents, Taxanes, Antitumor antibiotics, Camptothecins, Nitrosoureas), HER1/EGFR tyrosine kinase inhibitor, VEGF protein inhibitor, HER-2/ErbB2 inhibitor, Interferon, Interleukin, Monoclonal antibody, or Glucocorticoid steroid.

29. The ADC of claim 27, wherein the anti-proliferative agent is selected from erlotinib; docetaxel; gemcitabine; cisplatin; carboplatin; paclitaxel; trastuzumab; temozolomide; tamoxifen; doxorubicin; oxaliplatin; bortezomib; sutent; letrozole; imatinib mesylate; MEK inhibitor; fulvestrant; leucovorin (folinic acid); rapamycin; lapatinib; lonafarnib; sorafenib; gefitinib; irinotecan; tipifarnib; Cremophor-free paclitaxel; paclitaxel; vandetanib; chloranmbucil; temsirolimus; pazopanib; canfosfamide; thiotepa; cyclosphosphamide; 5 fluorouracil (5-FU); vinorelbine; novantrone; teniposide; edatrexate; daunomycin; aminopterin; capecitabine; ibandronate; topoisomerase inhibitor RFS 2000; -difluoromethylornithine (DMFO); tamoxifen; raloxifene; droloxifene, 4-hydroxytamoxifen; trioxifene; keoxifene; onapristone; toremifine citrate; 4(5)-imidazoles; aminoglutethimide; megestrol acetate; exemestane; formestanie; fadrozole; vorozole; letrozole; anastrozole; flutamide; nilutamide; bicalutamide; leuprolide; goserelin; troxacitabine (α-1,3-dioxolane nucleoside cytosine analog); lipid kinase inhibitor; oblimersen; aldesleukin; abarelix; bevacizumab; alemtuzumab; bevacizumab; cetuximab; panitumumab; rituximab; pertuzumab; trastuzumab; tositumomab; gemtuzumab; or ozogamicin.

30. A method of treating Globo series antigens expressing cancer in a subject, the method comprising administering to the subject in need thereof an effective amount of the ADC of claim 24.

31. The method of claim 30, wherein the Globo series antigens expressing cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

32. The method of claim 30, wherein the subject is human.

* * * * *